US009139809B2

(12) United States Patent
Porcelli et al.

(10) Patent No.: US 9,139,809 B2
(45) Date of Patent: Sep. 22, 2015

(54) BACTERIAL VACCINES WITH CELL WALL-ASSOCIATED CERAMIDE-LIKE GLYCOLIPIDS AND USES THEREOF

(75) Inventors: Steven A. Porcelli, Bronx, NY (US); Manjunatha M. Venkataswamy, Bronx, NY (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 357 days.

(21) Appl. No.: 12/684,685

(22) Filed: Jan. 8, 2010

(65) Prior Publication Data

US 2010/0183549 A1 Jul. 22, 2010

Related U.S. Application Data

(60) Provisional application No. 61/143,389, filed on Jan. 8, 2009.

(51) Int. Cl.
*A61K 39/02* (2006.01)
*C12N 1/20* (2006.01)
*A61K 39/04* (2006.01)
*A61K 39/00* (2006.01)

(52) U.S. Cl.
CPC . *C12N 1/20* (2013.01); *A61K 39/04* (2013.01); *A61K 2039/522* (2013.01); *A61K 2039/55511* (2013.01)

(58) Field of Classification Search
None
See application file for complete search history.

(56) References Cited

U.S. PATENT DOCUMENTS

| | | | |
|---|---|---|---|
| 4,690,915 A | 9/1987 | Rosenberg | |
| 5,081,029 A | 1/1992 | Zarling et al. | |
| 5,194,425 A | 3/1993 | Sharma et al. | |
| 5,635,363 A | 6/1997 | Altman et al. | |
| 5,679,347 A | 10/1997 | Porcelli et al. | |
| 5,780,441 A | 7/1998 | Higa et al. | |
| 5,849,716 A | 12/1998 | Akimoto et al. | |
| 5,853,737 A | 12/1998 | Modlin et al. | |
| 5,936,076 A | 8/1999 | Higa et al. | |
| 6,015,884 A | 1/2000 | Schneck et al. | |
| 6,162,609 A | 12/2000 | Hafter et al. | |
| 6,238,676 B1 | 5/2001 | Porcelli et al. | |
| 6,248,564 B1 | 6/2001 | Walter et al. | |
| 6,531,453 B1 | 3/2003 | Taniguchi et al. | |
| 6,548,067 B1 | 4/2003 | Seeman et al. | |
| 6,682,741 B1 | 1/2004 | Ribaudo et al. | |
| 6,747,010 B2 | 6/2004 | Taniguchi et al. | |
| 6,881,828 B2 | 4/2005 | Edwards et al. | |
| 7,273,852 B2 | 9/2007 | Tsuji et al. | |
| 7,666,656 B2 * | 2/2010 | Sun et al. | 435/253.1 |
| 7,772,380 B2 | 8/2010 | Porcelli | |
| 8,022,043 B2 | 9/2011 | Porcelli | |
| 2002/0051783 A1 | 5/2002 | Savage | |
| 2002/0071842 A1 | 6/2002 | Gumperz et al. | |
| 2002/0155447 A1 | 10/2002 | Zauderer et al. | |
| 2003/0157135 A1 | 8/2003 | Tsuji et al. | |
| 2003/0166277 A1 | 9/2003 | Zauderer et al. | |
| 2004/0091488 A1 | 5/2004 | Seeman et al. | |
| 2004/0127429 A1 | 7/2004 | Tsuji | |
| 2004/0210037 A1 | 10/2004 | Zauderer et al. | |
| 2005/0042218 A1 | 2/2005 | Zauderer | |
| 2005/0112141 A1 | 5/2005 | Terman | |
| 2005/0192248 A1 | 9/2005 | Tsuji et al. | |
| 2006/0019246 A1 | 1/2006 | Tsuji et al. | |
| 2006/0052316 A1 | 3/2006 | Porcelli | |
| 2006/0074235 A1 | 4/2006 | Annoura et al. | |
| 2006/0116331 A1 | 6/2006 | Jiang et al. | |
| 2006/0148723 A1 | 7/2006 | Yamamura et al. | |
| 2006/0211856 A1 | 9/2006 | Tsuji et al. | |
| 2006/0269540 A1 | 11/2006 | Robert et al. | |
| 2007/0238673 A1 | 10/2007 | Porcelli | |
| 2008/0254045 A1 | 10/2008 | Donda et al. | |
| 2013/0164325 A1 | 6/2013 | Porcelli et al. | |

FOREIGN PATENT DOCUMENTS

| | | |
|---|---|---|
| AU | B-39005/89 | 2/1990 |
| EP | 0 133 988 A2 | 3/1985 |
| EP | 0 352 761 B1 | 10/1995 |
| GB | 2 339 782 A | 2/2000 |
| WO | WO 93/10220 | 5/1993 |
| WO | WO 94/25610 | 11/1994 |
| WO | WO 96/26962 | 9/1996 |
| WO | WO 97/35991 | 10/1997 |
| WO | WO 98/07441 | 2/1998 |
| WO | WO98/23627 | 6/1998 |
| WO | WO 99/11775 | 3/1999 |
| WO | WO 99/13095 | 3/1999 |
| WO | WO 99/21572 | 5/1999 |
| WO | WO 99/31241 | 6/1999 |
| WO | WO 99/64464 | 12/1999 |

(Continued)

OTHER PUBLICATIONS

Tomioka Haruaki, Current pharmaceutical Design, 10(26):3297-312, 2004.*
Florence et al (Expert Reviews in Molecular Medicine, 10(e20)1-27, 2008.*
Minamino et al (Microbiology, 149:2071-2081, 2003).*
Mattner et al (Nature, 434(7032):525-529, 2005).*
Fischer et al (PNAS, 101(29):10685-10690, 2004).*
Andersen, P., et al., "Tuberculosis vaccines—an update," *Nature Reviews Microbiology*, 5: 484-486 (2007).
Balasubramanian, V., et al., "Mycobacterial infection in guinea pigs," *Immunobiology*, 191(4-5):395-401 (1994).
Barclay, W., et al., "Aerosol-Induced Tuberculosis in Subhuman Primates and the Course of the Disease After Intravenous BCG Vaccination," *Infect. Immun.* 2(5):574-582 (1970).
Behar, S., et al., "CD1-restricted T cells in host defense to infectious diseases," *Curr. Top. Microbiol. Immunol.* 314: 215-250 (2007).

(Continued)

*Primary Examiner* — Patricia A Duffy
(74) *Attorney, Agent, or Firm* — Alston & Bird LLP

(57) ABSTRACT

The invention is directed compositions and methods related to bacterial cells physically associated with ceramide-like glycolipids. The invention allows for delivery of ceramide-like glycolipid adjuvants directly to the same cells that become infected with a bacterial vaccine. The compositions and methods of the present invention are useful for the prevention and treatment of diseases.

40 Claims, 11 Drawing Sheets

(56) References Cited

FOREIGN PATENT DOCUMENTS

| WO | WO 99/64597 | | 12/1999 |
|---|---|---|---|
| WO | WO 00/00156 | | 1/2000 |
| WO | WO 01/44296 | A1 | 6/2001 |
| WO | WO 01/71005 | A2 | 9/2001 |
| WO | WO 01/72995 | A2 | 10/2001 |
| WO | WO 01/90198 | A1 | 11/2001 |
| WO | 03/009812 | * | 2/2003 |
| WO | WO2004/028475 | | 4/2004 |
| WO | WO 2004/029206 | A2 | 4/2004 |
| WO | WO2004/072091 | | 8/2004 |
| WO | WO 2005/000348 | A2 | 1/2005 |
| WO | WO2006/026389 | A2 | 3/2006 |
| WO | WO2007/007946 | | 1/2007 |
| WO | WO 2008/103392 | A2 | 8/2008 |
| WO | WO2008/133801 | A1 | 11/2008 |
| WO | WO2008/140598 | A2 | 11/2008 |
| WO | WO2012/006342 | A2 | 1/2012 |

OTHER PUBLICATIONS

Behar, S., et al., "Susceptibility of mice deficient in CD1D or TAP1 to infection with *Mycobacterium tuberculosis*," *J. Exp. Med.*, 189: 1973-1980 (1999).
Bendelac, A., "Mouse NK+T cells," *Current Opinion in Immunology*, 7:367-374 (1995).
Bendelac, A., et al., "CD1 Recognition by Mouse NK1+ T lymphocytes," *Science*, 268:863-865 (1995).
Bendelac, A., et al., "Mouse CD-1-Specific NK1 T Cells: Development, Specificity, and Function," *Annual Review Immunol.*, 15:535-562 (1997).
Benlagha, K., et al., "In Vivo identification of Glycolipid Antigen-specific T Cells Using Fluorescent CD1d Tetramers," *J. Exp. Med.*, 191(11):1895-1903 (2000).
Bhat, S., et al., "Galactosyl ceramide or a derivative is an essential component of the neural receptor for human immunodeficiency virus type 1 envelope glycoprotein gp120," *Proc. Natl. Acad. Sci.*, 88:7131-7134 (1991).
Bhat, S., et al., "Galactosyl ceramide or a derivative is an essential component neural receptor for human immunodeficiency virus type 1 envelope glycoprotein gp120," *Proc. Natl. Acad. Sci.*, 88:7131-7134 (1991).
Burdin, N., et al., "Immunization with α-galactosylceramide polarizes CD-1-reactive NK T cells toward Th2 cytokine synthesis," *Eur. J. Immunol.*, 29:2014-2025 (1999).
Bynoe, M., et al., "Characterization of anti-DNA B cells that escape negative selection," *Eur. J. Immunol.*, 29:1304-1313 (1999).
Bynoe, M., et al., "Estrogen up-regulates Bcl-2 and blocks tolerance induction of naïve B cells," *Proc. Natl. Acad. Sci.*, 97:6:2703-2708 (2000).
Chackerian, A., et al., "Activation of NKT cells protects mice from tuberculosis," *Infection and Immunity*, 70: 6302-6309 (2002).
Crowe, N., et al., "Glycolipid Antigen Drives Rapid Expansion and Sustained Cytokine Production by NK T Cells," *J. Immunol.*, 171:4020-4027 (2003).
Davodeau, F., et al., "Close Phenotypic and Functional Similarities Between Human and Murin αβ T Cells Expressing Invariant TCR α-Chains," *J. Immunol.*, 158:5603-5611 (1997).
Dondji, B., et al., "Intradermal NKT cell activation during DNA priming heterologous prime-boost vaccination enhances T cell responses and protection against *Leishmania*," *Eur. J. Immunol.*, 38: 706-719 (2008).
Emoto, M., et al., "Induction of IFN-γ-producing CD4+ natural killer T cells *Mycobacterium bovis bacillus* Calmette Guérin," *Eur. J. Immunol.*, 29: 650-659 (1999).
Enomoto, N., et al., "Immunization with dendritic cells loaded with α-galactosylceramide at priming phase, but not at boosting phase, enhances cytotoxic T lymphocyte activity against infection by intracellular bacteria," *FEMS Immunol. Med. Microbiol.*, 51: 350-362 (2007).

Erbel G., et al., "Rapid Death and Regeneration of NKT Cells in Anti-CD3ε- or IL-12-Treated Mice: A Major Role for Bone Marrow in NKT Cell Homeostasis," *Immunity*, 9:345-353 (1998).
Exley, M., et al., "Requirements for CD1d Recognition by Human Invariant Vα24+DC4-CD8-T Cells," *J. Exp. Med.*, 186:109-120 (1997).
Flynn, J, et al., "Major histocompatibility complex class I-restricted T cells are required for resistance to *Mycobacterium tuberculosis* infection," *Proc. Natl. Acad. Sci.*, 89: 12013-12017 (1992).
Freidag, B, et al., "CpG oligodeoxynucleotides and interleukin-12 improve the efficacy of *Mycobacterium bovis* BCG vaccination in mice challenged with *M. tuberculosis*," *Infect. Immun.*, 68: 2948-2953 (2000).
Fujii, S, et al., "Glycolipid α-C-galactosylceramide is a distinct inducer of dendritic cell function during innate and adaptive immune responses of mice," *Proc. Nat. Acad. Sci.*, 103:11252-11257 (2006).
Fujii, S., et al., "Activation of natural killer T cells by α-galactosylceramide rapidly induces the full maturation of dendritic cells in vivo and thereby acts as an adjuvant for combined CD4 and CD8 T cell immunity to a coadministered protein," *J. Exp. Med.*, 198: 267-279 (2003).
Fujii, S., et al., "Innate Vα14(+) natural killer T cells mature dendritic cells, leading to strong adaptive immunity," *Immunol. Rev.*, 220: 183-198 (2007).
Gaynor, B., et al., "Peptide inhibition of glomerular deposition of an anti-DNA antibody," *Proc. Natl. Acad. Sci.*, 94:1955-1960 (1997).
Godfrey, D., et al., "NKT cells: facts, functions and fallacies," *Immunol. Today*, 21(11):573-583 (2000).
Gonzalez-Aseguinolaza, G., "Natural killer T cell ligand α-galactosylceramide enhances protective immunity induced by malaria vaccines," *J. Exp. Med.*, 195: 617-624 (2002).
Gonzalez-Aseguinolaza, G., et al., "α-Galactosylceramide-activated Vα14 natural killer T cells mediate protection against murine malaria," *Proc. Natl. Acad. Sci.*, 97: 8461-8466 (2000).
Grode, L., et al., "Increased vaccine efficacy against tuberculosis of recombinant *Mycobacterium bovis* bacille Calmette-Guerin mutants that secrete listeriolysin," *Journal of Clinical Investigation*, 115: 2472-2479 (2005).
Hahn, B., "Antibodies to DNA," *New England Journal of Medicine*, 338:19:1359-1368 (1998).
Hammond, K., et al., αβ-T Cell Receptor (TCR)+DC4-CD8-(NKT) Thymocytes Prevent Insulin-dependent Diabetes Mellitus in Nonobese Diabetic (NOD)/Lt Mice by the Influence of Interleukin (IL)-4 and/or IL-10, *J. Exp. Med.*, 187(7):1047-1056 (1998).
Hayakawa, Y., et al., Critical contribution of IFN-γ and NK cells, but not perforin-mediated cytotoxicity, to anti-metastatic effect of α-galactosylceramide. *Eur. J. Immunol.*, 31: 1720-1727 (2001).
Hermans, I., et al., "NKT cells enhance CD4+ and CD8+ T cell responses to soluble antigen in vivo through direct interaction with dendritic cells," *J. Immunol.*, 171: 5140-5147 (2003).
Hinchey, J., et al., "Enhanced priming of adaptive immunity by a proapoptotic mutant of *Mycobacterium tuberculosis*," *Journal of Clinical Investigation*, 117: 2279-2288, (2007).
Hoft, D., "Tuberculosis vaccine development: goals, immunological design, and evaluation," *Lancet*, 372:164-175, (2008).
Hong, S, et al., "The natural killer T-cell ligand α-galactosylcermide prevents autoimmune diabetes in non-obese diabetic mice," *Nature Medicine*, 7(9):1052-1056 (2001).
Horwitz, M., et al., "Recombinant bacillus calmette-guerin (BCG) vaccines expressing the *Mycobacterium tuberculosis* 30-kDa major secretory protein induce greater protective immunity against tuberculosis than conventional BCG vaccines in a highly susceptible animal model," *Proc. Natl. Acad. Sci.*, 97: 13853-13858 (2000).
Huang, Y., et al., "Enhancement of HIV DNA vaccine immunogenicity by the NKT cell ligand, α-galactosylceramide," *Vaccine*, 26: 1807-1816 (2008).
Iborra, S., et al., "Vaccination with the *Leishmania major* ribosomal proteins plus CpG oligodeoxynucleotides induces protection against experimental cutaneous leishmaniasis in mice," *Microbes. Infect.*, 10:1133-1141 (2008).

(56) References Cited

OTHER PUBLICATIONS

Iijima, H., et al., "Structure-Activity Relationship and Conformational Analysis of Monoglycosylceramides on the Syngeneic Mixed Leukocyte Reaction," *Bioorganic & Medicine Chemistry*, 6:1905-1910 (1998).
Inoue, H. et al., "α-Galactosylcermide (AGL-517) treatment protects mice from lethal irradiation," *Experimental Hematology*, 25:935-944 (1997).
International Search Report for International Application No. PCT/US08/04546, United States and Trademark Office, U.S.A., mailed on Jul. 30, 2008.
Ishikawa, H., et al., "CD4(+) V(α)14 NKT cells play a crutial role in an early stage of protective immunity against infection with *Leishmania major*," *Int. Immunol.*, 12: 1267-1274 (2000).
Joyce, S., et al., "Natural Ligand of Mouse CD1d1: Cellular Glycosylphosphatidylinositol," *Science*, 279:1541-1544 (1998).
Kawano, T., et al., "CD1d-Restricted and TCR-Mediated Activation of Vα 14 NKT Cells by Glycosylceramides," *Science*, 278:1626-1629 (1997).
Kitamura, H., et al., "The natural killer T (NKT) cell ligand α-galactosylceramide demonstrates its immunopotentiating effect by inducing interleukin (IL)-12 production by dendritic cells and IL-12 receptor expression on NKT cells," *J. Exp. Med.*, 189: 1121-1128 (1999).
Kobayashi, E., et al., "Enhancing effects of agelasphon-11 on natural killer cell activities of normal and tumor-bearing mice," *Biol. Pharm Bull.*, 19:3:335-486 (1996).
Kobayashi, E., et al., "Enhancing Effects of α-, β-Monoglycosylcermides on Natural Killer Cell Activity," *Bioorganic & Medicinal Chemistry* 4:615-619 (1996).
Koboyashi, E., et al., "KRN7000, A Novel Immunomodulator, and Its Antitumor Activities," *Oncology Research*, 7(10):529-534 (1995).
Kojo, S., et al., "Dysfunction of T Cell Receptor AV24AJ18+, BV11 + Double-Negative Regulatory Natural Killer T Cells in Autoimmune Diseases," *Arthritis & Rheumatism*, 44(5):1127-1138 (2001).
Koseki, H., et al., "Dominant expression of a distinctive V14+ T-cell antigen receptor α chain in mice," *Proc. Natl. Acad.* 88:7518-7522 (1991).
Kotzin, B., et al. "Systemic Lupus Erythematosus," *Cell*, 85:303-306 (1996).
Kronenberg, M., "Toward an understanding on NKT cell biology: progress and paradoxes," *Annu. Rev. Immunol.*, 23: 877-900 (2005).
Kronenberg, M., et al., "The unconventional lifestyle on NKT cells," *Nat. Rev. Immunol.*, 2: 557-568 (2002).
Kuo, P., et al., "Bcl-2 leads to expression of anti-DNA B cells but no nephritis: a model for a clinical subset," *Eur. J. Immunol.*, 29:3168-3178 (1999).
Laloux, V., et al., "NK T Cell-Induced Protection Against Diabetes in Vα14-Jα281 Transgenic Nonobese Diabetic Mice Is Associated with a TH2 Shift Circumscribed Regionally to the Islets and Functionally to Islet Autoantigen," *Journal of Immunol.*, 66:3749-3756 (2001).
Lutz, M., et al., "An advanced culture method for generating large quantities of highly pure dendritic cells from mouse bone marrow," *J. Immunol. Methods* 223: 77-92 (1999).
Matsuda, J., et al., "Tracking the Response of Natural Killer T Cells to a Glycolipid Antigen Using CD1d Tetramers," *J. Exp. Med.*, 192(5):741-753 (2000).
Matsumoto et al., "Recombinant *Mycobacterium bovis* Bacillus Calmette-Guérin Secreting Merozoite Surface Protein 1 (MSP1) Induces Protection against Rodent Malaria Parasite Infection Depending on MSP1-stimulated Interferon γ and Parasite-specific Antibodies," *J. Exp. Med.*, 188 (5):845-854 (1998).
Mieza, M., et al., "Selective Reduction of Vα14+ NK T Cells Associated with Disease Development in Autoimmune-Prone Mice," *Journal of Immunol.*, 156:4035-4040 (1996).
Miyamoto, K. et al., "A synthetic glycolipid prevents autoimmune encephala myelitis by inducing $T_H2$ bias of natural killer T cells," *Nature*, 413:531-534 (2000).
Mogues, T., et al., "The relative importance of T cell subsets in immunity and immunopathology of airborne *Mycobacterium tuberculosis* infection in mice," *J. Exp. Med.*, 193: 271-280 (2001).
Moody, D., et al., "The molecular basis of CD1-medicated presentation of lipid antigens," *Immunol. Rev.*, 172:285-296 (1999).
Morita, M., et al., "Structure Relationship of α-Galactosylceramides against B-16-Bearing," *J. Med. Chem.*, 38:2176-2187 (1995).
Motoki, K., et al., "Immunostimulatory and a antitumor activities of monoglycosylceramides having various sugar moieties," *Biological & Pharmaceutical Bulletin* 18(11)1487-1491 (1995).
Motoki, M., et al., Effects of α-galactosylceramides on bone marrow cells in vitro and hematopoiesis in vivo, *Biol.& Pharm. Bull.*, 19(7):952-955 (1996).
Naidenko, O., et al., "Binding and antigen Presentation of Ceramide-containing Glycolipids by Soluble Mouse and Human CD1d Molecules," *J. Exp. Med.*, 190(8):1069-1079 (1999).
Nakagawa, R., et al., "Antitumor activity of α-galactosycleramide, KRN7000, in mice with EL-4 hepatic metastasis and its cytokine production," *Oncology Research*, 10:561-568 (1998).
Nakagawa, R., et al., "Antitumor activity of α-galactosylceramide, KRN7000, in mice with the melanoma B16 hepatic metastasis and immunohistological study of tumor infiltrating cells," *Oncology Research,* 12:51-58 (2000).
Nishimura, T., et al., "The interface between innate and acquired immunity: glycolipid antigen presentation by CD1d-expressing dendritic cells to NKT cells induces the differentiation of antigen-specific cytotoxic T lymphocytes," *Int. Immunol.*, 12: 987-994 (2000).
Office Action mailed Apr. 17, 2009, in U.S. Appl. No. 11/211,653, Porcelli, filed Aug. 26, 2005.
Office Action mailed Jan. 29, 2009, in U.S. Appl. No. 11/211,653, Porcelli, filed Aug. 26, 2005.
Office Action mailed Jun. 4, 2008, in U.S. Appl. No. 11/211,653, Porcelli, filed Aug. 26, 2005.
Office Action mailed Nov. 9, 2009, in U.S. Appl. No. 11/211,653, Porcelli, filed Aug. 26, 2005.
Office Action mailed Oct. 4, 2007, in U.S. Appl. No. 11/211,653, Porcelli, filed Aug. 26, 2005.
Oishi, Y., et al., "Selective reduction and recovery of invariant Vα24JαQ T cell receptor T cells in correlation with disease activity in patients with systemic lupus erythematosus," *Journal of Rheumatology*, 28(2):275-283 (2001).
Pisetsky, D.S., "Systemic lupus erythematosus. Diagnosis and treatment," *The Medical Clinics of North America: Advances in Rheumatology*, 81(1):113-128 (1997).
Porcelli, S., "The CD1 family: a third lineage of antigen-presenting molecules." *Advances in Immunology*, 59:1-98 (1995).
Porcelli, S., et al., "Analysis of T Cell Antigen Receptor (TCR) Expression by Human Peripheral Blood CD4-8 α/β T Cells Demonstrates Preferential Use of Several Vβ Genes and an Invariant TCR α Chain," *J. Exp. Med.*, 178:1-16 (1993).
Porcelli, S., et al., "The CD1 family of lipid antigen-presenting molecules," *Review Immunology Today*, 19(8):362-368 (1998).
Porcelli, S., et al., "The CD1 System: Antigen-Presenting Molecules for T Cell Recognition of Lipids and Glycolipids," *Annu. Rev. Immunol.*, 17:297-329 (1999).
Putterman, C., et al., "Molecular Analysis of the Autoantibody Response in Peptide-Induced Autoimmunity," *The Journal of Immunology* 164:2542-2549 (2000).
Putterman. C., et al., "Immunization with a Peptide Surrogate for Double-stranded DNA (dsDNA) Induces Autoantibody Production and Renal Immunoglobulin Deposition," *J. Exp. Med.*, 1:29-38 (1998).
Ranson, T., et al., "Invariant Vα14+ NKT cells participate in the early response to enteric *Listeria monocytogenes* infection," *J. Immunol.*, 175: 1137-1144 (2005).
Rao et al., "Trans-cyclopropanation of mycolic acids on trehalose dimycolate suppresses *Mycobacterium tuberculosis*-induced inflammation and virulence," *J. Clin. Invest.*, 116(6):1660-1667 (2006).
Rao, V., et al., "*Mycobacterium tuberculosis* controls host innate immune activation through cyclopropane modification of glycolipid effector molecule," *J. Exp. Med.*, 201(4):535-43 (2005).

(56) References Cited

OTHER PUBLICATIONS

Schmieg, J., "Superior protection against malaria and melanoma metastases by a C-glycoside analogue of the natural killer T cell ligand α-galactosylceramide," *J. Exp. Med.*, 198: 1631-1641 (2003).

Sharif, S., et al., "Activation of natural killer T cells by α-galactosyclceramide treatment prevents the onset and recurrence of autoimmune Type 1 diabetes," *Nature Medicine*, 7(9):1057-1062 (2001).

Sharif, S., et al., "Regulation of autoimmune disease by natural killer T cells," *Journal of Mol. Med.*, 80:290-300 (2002).

Sidobre, S., et al., "The Vα14 NKT Cell TCR Exhibits High-Affinity Binding to a Glycolipid/CD1d Complex," *J. Immunol.*, 169:1340-1348 (2002).

Sieling, P., et al., Human Double-Negative T Cells in Systematic Lupus Erythematosus Provide Help for IgG and are Restricted by CD1c, *J. Immunol.*, 165:5338-5344 (2000).

Silk, J., et al., "Utilizing the adjuvant properties of CD1d-dependent NK T cells in T cell-mediated immunotherapy," *J. Clin. Invest.*, 114: 1800-1811 (2004).

Smyth, M., et al., Sequential production of interferon-γ by NK1.1(+) T cells and natural killer cells is essential for the antimetastatic effect of α-galactosylceramide. *Blood*, 99: 1259-1266 (2002).

Smyth. M., et al., "NKT cells and tumor immunity—a double-edged sword," *Nature Immunology*, 1(6):459-460 (2000).

Spada. F., et al., "CD1d-restricted Recognition of Synthetic Glycolipid Antigens by Human Natural Killer T Cells," *J. Exp. Med.*, 188(8):1529-1534 (1998).

Spatz, L., et al., "Light Chain Usage in Anti-double-stranded DNA B Cell Subsets: Role in Cell Fate Determination," *J. Exp. Med.*, 185(7):1317-1326 (1997).

Sumida, T., et al., "Selective Reduction of T Cells Bearing Invariant Vα24JαQ Antigen Receptor in Patients with Systemic Sclerosis," *J. Exp. Med.*, 182:1163-1168 (1995).

Takeda, K., et al., "The Development of Autoimmunity in C57BL/6 lpr ice Correlates with the Disappearance of Natural Killer Type 1-positive Cells: Evidence for Their Suppressive Action on Bone Marrow Stem Cell Proliferation, B Cell Immunoglobulin Secretion, and Autoimmune Symptoms," *Journal Exp. Medicine* 177:155-164 (1993).

Taraban, V., et al., "Invariant NKT cells promote CD8+ cytotoxic T cell responses by inducing CD70 expression on dendritic cells," *J. Immunol.*, 180: 4615-4620 (2008).

Tsuji, M., "Glycolipids and phospholipids as natural CD1d-binding NKT cell ligands," *Cell Mol. Life Sci.*, 63: 1889-1898 (2006).

Uchimura, A., et al., "Immunostimulatory Activities of Mono- or Diglycosylated α-Galactosyceramides," *Bioorg. Med. Chem.*, 5(7):1447-1452 (1997).

Uchimura, A., et al., "Immunostimulatory Activities of Monoglycosylated α-D-Pyranosylceramides," *Bioorg. Med. Chem.*, 5(12):2245-2249 (1997).

Wang, B., et al., "CD-1 restricted NK T Cells Protect Nonobese Diabetic Mice from Developing Diabetes," *J. Exp. Med.*, 194(3):313-319 (2001).

Whitmire, J., et al., "Direct interferon-γ signaling dramatically enhances CD4+ and CD8+ T cell memory," *J. Immunol.*, 179: 1190-1197 (2007).

Wilson, S., et al., "Extreme Th1 bias of invariant Vα24JαQ T cells in type 1 diabetes," *Nature*, 391:177-181 (1998).

Yamaguchi, Y., et al., "Enhancing Effects of (2S,3S,4R)-1-O-(α-D-galactopyranosyl)-2-(Nhexacosanoylamino)- 1,3,4-octadecanetriol (KRN7000) on antigen-presenting cells and antimetastatic activity of KRN7000-pretreated antigen-presenting cells and antimetastatic activity of KRN7000-pretreated antigen presenting cells," *Oncology Research*, 8(10/11):399-407 (1996).

Yoshimoto, T., et al., "Role of NK. 1+Cells in a $T_H2$ Response and in Immunoglobulin E Production," *Science*, 270(5243):1845-1847 (1995).

Yoshimoto, T., et al., "CD4$^{pos}$, NK1.1$^{pos}$ T Cells Promptly Produce Interleukin 4 in Response to In Vivo Challenge with Anti-CD3," *J. Exp. Med.*, 179:1285-1295 (1994).

Yoshimoto, T., et al., "Defective IgE production by SJL mice is linked to the absence of CD4+, NK1.1+T cells that promptly produce interleukin 4," *Proc. Natl. Acad. Sci.*, 92:11931-11934 (1995).

Young, D., et al., "Confronting the scientific obstacles to global control of tuberculosis," *J. Clin. Inv.*, 118: 1255-1265, (2008).

Yu, K., et al., "Modulation of CD1d-restricted NKT cell responses by using N-acyl variants of α-galactosylceramides," *Proc. Natl. Acad. Sci.*, 102:3383-3388 (2005).

Zeng, D., et al., "Cutting Edge: A Role for CD1 in the Pathogenesis of Lupus in NZB/NZW Mice," *J. Immunol.*, 164:5000-5004 (2000).

Zeng, Z.-H., et al., "Crystal Structure of Mouse CD1: An MHC-Like Fold with a Large Hydrophobic Binding Groove," *Science*, 277:339-345 (1997).

Carnaud, C., et al., "Cutting Edge: Cross-Talk Between Cells of the Innate Immune System: NKT Cells Rapidly Activate NK Cells," *J Immunol*, 1999, vol. 163(9), pp. 4647-4650.

Chen, H., et al., "Cultured NK1.1+CD4+T Cells Produce Large Amounts of IL-4 and IFN-γ Upon Activation by Anti-CD3 or CD1," *The Journal of Immunology*, 1997, vol. 159(5), pp. 2240-2249.

Eberl, G., et al., "Selective induction of NK cell proliferation and cytotoxicity by activated NKT cells," *Eur. J. Immunol.*, 2000, vol. 30(4), pp. 985-992.

Galli, G., et al., "Invariant NKT cells sustain specific B cell responses and memory," *PNAS*, 2007, vol. 104(10), pp. 3984-3989.

Gumperz, J., et al., "Functionally Distinct Subsets of CD1d-restricted Natural Killer T Cells Revealed by CD1d Tetramer Staining," *J. Exp. Med.*, 2002, vol. 195(5), pp. 625-636.

Hermans, I., et al., "Dendritic Cell Function Can Be Modulated through Cooperative Actions of TLR Ligands and Invariant NKT Cells," *The Journal of Immunology*, 2007, vol. 178(5), pp. 2721-2729.

Kakimi, K., et al., "Natural Killer T Cell Activation Inhibits Hepatitis B Virus Replication In Vivo," *J. Exp. Med.*, 2000, vol. 192(7), pp. 921-930.

Karadimitris, A., et al., "Human CD1d-glycolipid tetramers generated by in vitro oxidative refolding chromatography," *PNAS*, 2001, vol. 98(6), pp. 3294-3298.

Kawakami, K., et al., "Activation of Vα14+Natural Killer T Cells by α-Galactosylceramide Results in Development of Th1 Response and Local Host Resistance in Mice Infected with *Cryptococcus neoformans*," *Infect. Immun.*, 2001, vol. 69(1), pp. 213-220.

Lee, Peter T., et al., "Distinct Functional Lineages of Human Vα24 Natural Killer T Cells," *J. Exp. Med.*, 2002, vol. 195(5), pp. 637-641.

Stober, D., et al., "NKT Cells Provide Help for Dendritic Cell-Dependent Priming of MHC Class I-Restricted CD8+ T Cells In Vivo," *J. Immunol.*, 2003, vol. 170(5), pp. 2540-2548.

Livingston, et al., "Improved Survival in Stage III Melanoma Patients With GM2 Antibodies: A Randomized Trial of Adjuvant Vaccination With GM2 Ganglioside," *Journal of Clinical Oncology*, 1994, vol. 12(5), pp. 1036-1044.

Brossay, et al., "Cutting Edge: Structural Requirements for Galactosylceramide Recognition by CD1-Restricted NK T Cells," *Journal of Immunology*, 1998, vol. 161(10), pp. 5124-5128.

Chang, et al., "The Synthesis and Biological Characterization of a Ceramide Library," *J. Am. Chem. Soc.*, 2002, vol. 124(9), pp. 1856-1857.

Cook, et al., "Alternatively activated dendritic cells regulate CD4+T-cell polarization in vitro and in vivo," *PNAS*, 2012, vol. 109(25), pp. 9977-9982.

Nagle, et al., "New glycosphingolipids from the marine sponge *Halichondria panicea*," *Journal of Natural Products*, 1992, vol. 55(7), pp. 1013-1017.

Park, et al., "Fine specificity of natural killer T cells against GD3 ganglioside and identification of GM3 as an inhibitory natural killer T-cell ligand," *Immunology*, 2008, vol. 123, pp. 145-155.

Venkataswamy, et al., "Incorporation of NKT cell activating glycolipids enhances immunogenicity and vaccine efficacy of *Mycobacterium bovis* BCG," *J. Immunol.*, 2009, vol. 183(3), pp. 1644-1656.

Wu, et al., "Cross-presentation of Disialoganglioside GD3 to Natural Killer T Cells," *J. Exp. Med.*, 2003, vol. 198 (1), pp. 173-181.

Cayabyab, M.J., et al., "Recombinant *Mycobacterium bovis* BCG Prime-Recombinant Adenovirus Boost Vaccination in Rhesus Mon-

(56) References Cited

OTHER PUBLICATIONS keys Elicits Robust Polyfunctional Simian Immunodeficiency Virus-Specific T-Cell Responses," *Journal of Virology*, 2009, vol. 83, No. 11, pp. 5505-5513.
Abastado, J-P., et al., "Dimerization of Soluble Major Histocomptability Complex-Peptide Complexes Is Sufficient for Activation of T Cell Hybridoma and Induction of Unresponsiveness," *J. Exp. Med.*, 1995, vol. 182, pp. 439-447.
Abdel-Wahab, Z., et al., "Human Dendritic Cells, Pulsed with either Melanoma Tumor Cell Lysates or the gp100 Peptide$_{(280-288)}$, Induce Pairs of T-Cell Cultures with Similar Phenotype and Lytic Activity," *Cellular Immunol.*, 1998, vol. 186, pp. 63-74.
Alexander, J., et al., "Recognition of a Novel Naturally Processed, A2 Restricted, HCV-NS4 Epitope Triggers IFN-gamma Release in Absence of Detectable Cytopathicity," *Human Immunol.*, 1998, vol. 59, pp. 776-782.
Alexander, M., et al., "Generation of tumor-specific cytolytic T lymphocytes from peripheral blood of cervical cancer patients by in vitro stimulation with a synthetic human papillomavirus type 16 E7 epitope," *Am. J. Obstet. Gynecol.*, 1996, vol. 175, pp. 15861593.
Altman, J. D., et al., "Phenotypic Analysis of Antigen-Specific T Lymphocytes," *Science*, 1996, vol. 274, pp. 94-96.
Balk, S. P., et al., "Isolation and characterization of a cDNA and gene coding for a fourth CD1 molecule," *Proc. Natl. Acad. Sci. USA*, 1989, vol. 86, pp. 252-256.
Battegay, M., et al., "Patients with Chronic Hepatitis C Have Circulating Cytotoxic T Cells Which Recognize Hepatitis C Virus-Encoded Peptides Binding to HLA-A2.1 Molecules," *J. Virology*, 1995, vol. 69, No. 4, pp. 2462-2470.
Beaudoin, L., et al., "NKT Cells Inhibit the Onset of Diabetes by Impairing the Development of Pathogenic T Cells Specific for Pancreatic B Cells," *Immunity*, 2002, vol. 17, pp. 725-736.
Bedzyk, W., et al., "Immunological and Structural Characterization of a High Affinity Anti-flourescein Single-chain Antibody," *The Journal of Biological Chemistry*, 1990, vol. 265(30), pp. 18615-18620.
Bendle. G., et al., "A Study of T Cell Tolerance to the Tumor-Associated Antigen MDM2: Cytokines Can Restore Antigen Responsiveness, but Not High Avidity T Cell Function," *PLos One*, Apr. 2007, vol. 353(4), pp. 1-9.
Bertoletti, A., et al., "Molecular Features of the Hepatitis B Virus Nucleocapsid T-Cell Epitope 18-27: Interaction With HLA and T Cell Receptor," *Hepatology*, 1997, vol. 26, pp. 1027-1034.
Bocchia, M., et al., "Specific Binding of Leukemia Oncogene Fusion Protein Peptides to HLA Class I Molecules," *Blood*, 1995, vol. 85, No. 10, pp. 2680-2684.
Bocchia, M., et al., "Specific Human Cellular Immunity to bcr-abl Oncogene-Derived Peptides," *Blood*, 1996, vol. 87, No. 9, pp. 3587-3592.
Boitel, B., et al., "Strong Similarities in Antigen Fine Specificity Among DRB1*1302-Restricted Tetanus Toxin tt830-843-Specific TCRs in Spite of Highly Heterogeneous CDR3," *J. Immunol.*, 1995, vol. 154, pp. 3245-3255.
Boniface, J. J., et al., "Initiation of Signal Transduction through the T Cell Receptor Requires the Multivalent Engagement of Peptide/Mhc Ligands," *Immunity*, 1998, vol. 9, pp. 459-466.
Bonish, B., et al., "Overexpression of CD1d by Keratinocytes in Psoriasis and CD1d-Dependent IFN-γ Production by NK-T Cells," *Immunol.*, 2000, vol. 165, pp. 4076-4085.
Brinckerhoff, L. H., et al., "Terminal Modifications Inhibit Proteolytic Degradation of an Immunogenic Mart-1$_{27-35}$Peptide: Implications for Peptide Vaccines," *Int. J. Cancer*, 1999, vol. 83, pp. 326-334.
Brusic, V., et al., "Prediction of MHC class II-binding peptides using an evolutionary algorithm and artificial neural network," *Bioinformatics*, 1998, vol. 14, No. 2, pp. 121-130.
Burrows, G. G., et al., "two-Domain Class II Mlecules Form Stable Complexes with Myelin Basic Protein 69-89 Peptide That Detect and Inhibit Rat Encephalitogenc T Cells and Treat Experimental Autoimmune Encephalomyelitis," *j Immunol*, 1998, vol. 161, pp. 5987-5996.

Casares, S., et al., "Antigen-specific Signaling by a Soluble, Dimeric Peptide/Major Histocompatibility Complex Class II/Fc Chimera Leading to T Helper Cell Type 2 Differentiation," *J. Exp. Med.*, 1999, vol. 190, No. 4, pp. 543-553.
Castelli, C., et al., "Novel HLA-Cw8-Restricted T Cell Epitopes Derived from Tyrosinase-Related Protein-2 and gp100 Melanoma Antigens," *J. Immunol.*, 1999, vol. 162, pp. 1739-1748.
Celts, E., et al., "Identification of Potential CTL Epitopes of Tumor-Associated Antigen MAGE-1 for Five Common HLA-A Alleles," *Mol. Immunol.*, 1994, vol. 31, No. 18, pp. 1423-1430.
Chaux, P., et al., "Identification of MAGE-3 Epitopes Presented by HLA-DR Molecules to CD4$^+$T Lymphocytes," *J. Exp. Med.*, 1999, vol. 189, No. 5, pp. 767-777.
Chikamatsu, K., et al., "Generation of Anti-p53 Cytotoxic T Lymphocytes from Human Peripheral Blood Using Autologous Dendritic Cells," *Clin. Cancer Res.*, 1999, vol. 5, pp. 1281-1288.
Cochran, J. R., et al., "The Relationship of MHC-Peptide Binding and T Cell Activation Probed Using Chemically Defined MHC Class II Oligomers," *Immunity*, 2000, vol. 12, pp. 241-250.
Cormier, J. N., et al., "Heterogeneous Expression of Melanoma-Associated Antigens and HLA-A2 in Metastatic Melanoma in vivo," *Int. J. Cancer*, 1998, vol. 75, pp. 517-524.
Cui, J., et al., "Requirement for V$_\alpha$14 NKT Cells in IL-12-Mediated Rejection of Tumors," *Science*, 1997, vol. 278, pp. 1623-1626.
Dal Porto, J., et al., "A soluble divalent class I major histocompatibility complex molecule inhibits alloreactive T cells at nanomolar concentrations," *Proc. Natl. Acad. Sci. USA*, 1993, vol. 90, pp. 6671-6675.
Daniel, S., et al., "Relationship Between Peptide Selectives of Human Transporters Associated with Antigen Processing and HLA Class I Molecules," *J. Immunol.*, 1998, vol. 161, pp. 617-624.
De Backer, O., et al., "Characterization of the *GAGE* Genes That Are Expressed in Various Human Cancers and in Normal Testis," *Cancer Res.*, 1999, vol. 59, pp. 3157-3165.
De St. Groth, B. F., et al., "T cell activation: in vivo veritas," *Immunology and Cell Biology*, 2004, vol. 82, pp. 260-268.
Diepolder, H. M., et al., "Immunodominant CD4$^+$T-Cell Epitope within Nonstructural Protein 3 in Acute Hepatitis C Virus Infection," *J. Virol.*, 1997, vol. 71, No. 8, pp. 6011-6019.
Donda, A., et al., "In vivo targeting of an anti-tumor antibody coupled to antigenic MHC class I complexes induces specific growth inhibition and regression of established syngeneic tumor grafts," *Cancer Immunity*, 2003, vol. 3, p. 11.
Doolan, D. L., et al., "Degenerate Cytotoxic T Cell Epitopes from P. falciparum Restricted by Multiple HLA-A and HLA-B Supertype Alleles," *Immunity*, 1997, vol. 7, pp. 97-112.
Dutronc, Y. And Porcelli, S. A., "The CD1 family and T cell recognition of lipid antigens," *Tissue Antigens*, 2002, vol. 60, pp. 337-353.
Esser, S., et al., "Vascular endothelial growth factor induces VE-cadherin tyrosine phosphorylation in endothelial cells," *J. Cell Science*, 1998, vol. 111, pp. 1853-1865.
Fayen, J., et al., "Class I MHC Alpha 3 Domain Can Function as an Independent Structural Unit to Bind CD8a," *Mol. Immunol.* 1995, vol. 32, No. 4, pp. 267-275.
Fleischhauer, K., et al., "Functional Heterogeneity of HLA-A*02 Subtypes Revealed by Presentation of a MAGE-3-Encoded Peptide to Cytotoxic T Cell Clones," *J. Immunol.*, 1997, vol. 159, pp. 2513-2521.
Fujii, S., et al., "Prolonged IFN-Y-producing NKT response induced with α-galactosylceramide-loaded DCs," *Nature Immunology*, 2002, vol. 3, pp. 867-874.
Glick, M., et al., "Novel CD8$^+$T Cell Antagonist Based on β$_2$-Microglobulin," *The Journal of Biological Chemistry*, 202, vol. 277, No. 23, pp. 20840-20846.
Gotch, F., et al., "Cytotoxic T lymphocytes recognize a fragment of influenza virus matrix protein in association with HLA-A2," *Nature*, 1987, vol. 326, pp. 881-882.
Greten, T. F., et al., "Direct visualization of antigen-specific T cells: HTLV-1 Tax11-19-specific CD8$^+$T cells are activated in peripheral blood and accumulate in cerebrospinal fluid from HAM/TSP patients," *Proc. Natl. Acad. Sci. USA*, 1998, vol. 95, pp. 7568-7573.

(56) References Cited

OTHER PUBLICATIONS

Hamad, A. R. A., et al., "Potent T Cell Activation with Dimeric Peptide-Major Histocompatibility Complex Class II Ligand: The Role of CD4 Coreceptor," *J. Exp. Med.*, 1998, vol. 188, No. 9, pp. 1633-1640.
Harbury, P. B., et al., "A Switch Between Two-, Three-, and Four-Stranded Coiled Coils in GCN4 Leucine Zipper Mutants," *Science*, 1993, vol. 262, pp. 1401-1407.
Harvill, E. T., et al., "In Vivo Properties of an IgG3-IL-2 Fusion Protein," *J. Immunol.*, 1996, vol. 157, pp. 3165-3170.
Heathcote, J., et al., "A Pilot Study of the CY-1899 T-Cell Vaccine in Subjects Chronically Infected With Hepatitis B Virus," *Hepatology*, 1999, vol. 30, pp. 531-536.
Hebert, A. M., et al., "Kinetics and Thermodynamics of $\beta$2-Microglobulin Binding to the $\alpha$3 Domain of Major Histocompatibility Complex Class I Heavy Chain," *Biochemistry*, 2001, vol., 40, pp. 5233-5242.
Hemmi, H., et al., "Small anti-viral compounds activate immune cells via the TLR7 MyD88-dependent signaling pathway," *Nature Immunol.*, 2002, vol. 3, No. 2, pp. 196-200.
Hochman, J. H., et al., "Specific Associations of Fluorescent $\beta$2-Microglobulin with Cell Surfaces; The Affinity of Different H-2 and HLA Antigens for $\beta$-2-Microglobulin," *The Journal of Immunology*, 1998, vol. 140, pp. 2322-2329.
Hoffmann, P., et al., "Large-scale in vitro expansion of polyclonal human CD4$^+$CD25$^{high}$regulatory T Cells," *Blood*, 2004, vol. 104, No. 3, pp. 895-903.
Höllsberg, P., et al., "Differential activation of proliferation and cytotoxicity in human T-cell lymphotropic virus type I Tax-specific CD8 T cells by an altered peptide ligand," *Proc. Natl. Acad. Sci. USA*, 1995, vol. 92, pp. 4036-4040.
Illés, Z., et al., "Differential Expression of NK T Cell V$\alpha$24J$\alpha$ Q Invariant TCR Chain in the Lesions of Multiple Sclerosis and Chronic Inflammatory Demyelinating Polyneuropathy," *J. Immunol.*, 2000, vol. 164, pp. 4375-4381.
Im, J. S., et al., "Direct Measurement of Antigen Binding Properties of CD1 Proteins Using Florescent Lipid Probes," *The Journal of Biological Chemistry*, 2004, vol. 279, pp. 299-310.
Jahng, A. W., et al., "Activation of Natural Killer T Cells Potentiates or Prevents Experimental Autoimmune Encephalomyelitis," *J. Exp. Med.*, 2001, vol. 194, No. 12, pp. 1789-1799.
Kang, S., et al., "Saposins facilitate CD1d-restricted presentation of an exogenous lipid antigen to T cells," *Nature Immunology*, 2004, vol. 5, No. 2, pp. 175-181.
Kawashima, I., et al., "Identification of gp100-Derived, Melanoma-Specific Cytotoxic T-Lymphocyte Epitopes Restricted by HLA-A3 Supertype Molecules by Primary in Vitro Immunization with Peptide-Pulsed Dendritic Cells," *Int. J. Cancer*, 1998, vol. 78, pp. 518-524.
Kawashima, I., et al., "Identification of HLA-A3-restricted Cytotoxic T Lymphocyte Epitopes from Carcinoembryonic Antigen and HER-2/ neu by Primary in Vitro Immunization with Peptide-pulsed Dendritic Cells," *Cancer Res.*, 1999, vol. 59, pp. 431-435.
Kim, J., et al., "Determinants of T Cell Reactivity to the *Mycobacterium leprae*GroES Homologue," *J. Immunol.*, 1997, vol. 159, pp. 335-343.
Kita, H., et al., "Quantitation and Phenotypic Analysis of Natural Killer T Cells in Primary Biliary Cirrhosis Using a Human CD1d Tetramer," *Gastroenterology*, 2002, vol. 123, pp. 1031-1043.
Kojo, S., et al., "Alternative Splicing Forms of the Human CD1D Gene in Mononuclear Cells," *Biochem. Biophys. Res. Comm.*, 2000, vol. 276, pp. 107-111.
Kojo, S., et al., "Low Expression Levels of Soluble CD1d Gene on Patients with Rheumatoid Arthritis," *J. Rheumatol.*, 2003, vol. 30, pp. 2524-2528.
Kono, K., et al., "Identification of HER2/neu-Derived Peptide Epitopes Recognized by Gastric Cancer-Specific Cytotoxic T Lymphocytes," *Int J Cancer*, 1998, vol. 78, pp. 202-208.
Kundu, S. K., et al., "Role of Preimmunization Virus Sequences in Cellular Immunity in HIV-Infected Patients during HIV Type 1 MN Recombinant gp160 Immunization," *Aids Research and Human Retroviruses*, 1998, vol. 14, No. 18, pp. 1669-1678.
Lachman, L. B., et al., "Cytokine-Containing Liposomes as Adjuvants for Subunit Vaccines," Vaccine Design: The Subunit and Adjuvant Approach. (1995). New York, NY: Plenum Press, eds. Michael F. Powell & Mark J. Newman, pp. 659-671.
Lee, A., et al., "Novel synthesis of $\alpha$-galactosyl-ceramides and confirmation of their powerful NKT cell agonist activity," *Carbohydrate Res.*, 2006, vol. 341, pp. 2785-2798.
Livingston, B. D., et al., "The Hepatitis B Virus-Specific CTL Responses Induced in Humans by Lipopeptide Vaccination Are Comparable to Those Elicited by Acute Viral Infection," *J. Immunol.*, 1997, vol. 159, pp. 1383-1392.
Mallevaey, T., et al., "Invariant and Noninvariant Natural Killer T Cells Exert Opposite Regulatory Functions on the Immune Response during Murine Schistosomiasis," *Infection and Immunity*, 2007, vol. 75, No. 5, pp. 2171-2180.
Mancini, S., et al., "Melanoma Cells Present a MAGE-3 Epitope to CD4+ Cytotoxic T Cells in Association with Histocompatibility Leukocyte Antigen DR11," *J. Exp. Med.*, 1999, vol. 189, No. 5, pp. 871-876.
Morrison, S. L., et al., "Production and Characterization of Genetically Engineered Antibody Molecules," *Clin. Chem.*, 1988, vol. 34, No. 9, pp. 1668-1675.
Mottez, E., et al., "Cells Expressing a Major Histocompatibility Complex Class I Molecule with a Single Covalently Bound Peptide Are Highly Immunogenic," *J. Exp. Med.*, 1995, vol. 181, pp. 493-502.
Nagarajan, A. N., and Kronenberg, M., "Invariant NKT Cells Amplify the Innate Immune Response to Lipopolysaccharide," *The Journal of Immunology*, 2007, pp. 2706-2713.
Naumov, Y. N., et al., "Activation of CD1d-restricted T cells protects NOD mice from developing diabetes by regulating dendritic cell subsets," *PNAS*, 2001, vol. 98, No. 24, pp. 13838-13843.
NCBI Entrez, GenBank Report, Accession No. P01885 (Entry Date 1993), 3 pages.
NCBI Entrez, GenBank Report, Accession No. P23043 (Entry Date 1993), 3 pages.
NCBI Entrez, GenBank Report, Accession No. NP 001757 (Entry Date 1999), 4 pages.
NCBI Entrez, GenBank Report, Accession No. NP 004039 (Entry Date 1999), 3 pages.
NCBI Entrez, GenBank Report, Accession No. NP 031665 (Entry Date 2000), 3 pages.
NCBI Entrez, GenBank Report, Accession No. NP 033865 (Entry Date 2000), 3 pages.
NCBI Entrez, GenBank Report, Accession No. NP 036644 (Entry Date 2000), 3 pages.
NCBI Entrez, GenBank Report, Accession No. NP 058775 (Entry Date 2000), 2 pages.
NCBI Entrez, GenBank Report, Accession No. Q29422 (Entry Date 2001), 3 pages.
NCBI Entrez, GenBank Report, Accession No. 062848 (Entry Date 2001), 3 pages.
NCBI Entrez, GenBank Report, Accession No. NP 999143 (Entry Date 2004), 2 pages.
NCBI Entrez, GenBank Report, Accession No. NP 001009066 (Entry Date 2005), 2 pages.
NCBI Entrez, GenBank Report, Accession No. NP 001009284 (Entry Date 2005), 2 pages.
NCBI Entrez, GenBank Report, Accession No. NP 001065272 (Entry Date 2006), 2 pages.
Nukaya, I., et al., "Identification of HLA-A24 Epitope Peptides of Carcinoembryonic Antigen Which Induce Tumor-Reactive Cytotoxic T Lymphocyte," *Int. J. Cancer*, 1999, vol. 80, pp. 92-97.
Ogg, G. S., et al., "Sensitization of tumour cells to lysis by virus-specific CTL using antibody-targeted MHC class I/peptide complexes," *British J. Cancer*, 2000, vol. 82, No. 5, pp. 1058-1062.
Pack, P., et al., "Tetravalent Miniantibodies with High Avidity Assembling in *Escherichia coli*," *J. Mol. Biol.*, 1995, vol. 246, pp. 28-34.

(56) References Cited

OTHER PUBLICATIONS

Parekh, V. V., et al., "Glycolipid antigen induces long-term natural killer T cell anergy in mice," the Journal of Clinical Investigation, 2005, vol. 115, pp. 2572-2583.

Parekh, V. V., et al., "The in Vivo Response of invariant Natural Killer T Cells to Glycolipid Antigens," 2007, *Int Rev Immunol*, vol. 26, pp. 31-48.

Parhman, P., et al., "Carbohydrate Moiety of HLA Antigens," *The Journal of Biological Chemistry*, 1977, vol. 252, No. 21, pp. 7555-7567.

Parker, K. C. And Strominger, J. L., "Subunit Interactions of Class I Histocompatibility Antigens," *Biochem.*, 1985, vol. 24, pp. 5543-5550.

Parkhurst, M. R., et al., "Identification of a Shared HLA-A*0201-restricted T-Cell Epitope from the Melanoma Antigen Tyrosinase-related Protein 2 (TRP2)," Cancer Res., 1998, vol. 58, pp. 4895-4901.

Pavlinkova, G., et al., "Pharmacokinetics and biodistribution of a light-chain-shuffled CC49 single-chain Fv antibody construct," *Cancer Immunol Immunther*, 2000, vol. 49, pp. 267-275.

Peiper, M., et al., "Pancreatic Cancer Associated Ascites-Derived CTL Recognize a Nine-Amino-Acid Peptide GP2 Derived from HER2/neu," *Anticancer Res.*, 1999, vol. 19, pp. 2471-2476.

Penichet, M. L., et al., "An Antibody-Avidin Fusion Protein Specific for the Transferrin Receptor Serves as a Delivery Vehicle for Effective Brain Targeting: Initial Applications in Anti-HIV Antisense Drug Delivery to the Brain," *J. Immunol.*, 1999, vol. 163, pp. 4421-4426.

Peterson, P. A., et al., "$\beta_2$-Microglobulin and the Major Histocompatibility Complex," 1977, Adv. Cancer Res. vol. 24, pp. 115-163.

Porubsky, S., et al., "Normal development and function of invariant natural killer T cells in mice with isoglobotrihexosylceramide (iGb3) deficiency," *PNAS*, 2007, vol. 104, No. 14, pp. 5977-5982.

Raniakrishna, V., et al., "Generation and Phenotypic Characterization of New Human Ovarian Cancer Cell Lines With the Identification of Antigens Potentially Recognizable by HLA-Restricted Cytotoxic T Cells," *Int. J. Cancer*, 1997, vol. 73, pp. 143-150.

Reinhardt, C. And Melms, A., "Elevated frequencies of natural killer T lymphocytes in myasthenia gravis," *Neurology*, 1999, vol. 52, pp. 1485-1487.

Ressing, M. E., et al., "Human CTL Epitopes Encoded by Human Papillomavirus Type 16 E6 and E7 Identified Through in Vivo and in Vitro Immunogenicity Studies of HLA-A*0201-Binding Peptides," *J. Immunol.*, 1995, vol. 154, pp. 5934-5943.

Rivoltini, L., et al., "A Superagonist Variant of Peptide MART1/Melan A$_{27-35}$Elicits Anti-Melanoma CD8$^+$T Cells with Enhanced Functional Characteristics: Implication for More Effective Immunotherapy," *Cancer Res.*, 1999, vol. 59, pp. 301-306.

Robert, B., et al., "Antibody-conjugated MHC class I tetramers can target tumor cells for specific lysis by T lymphocytes," *Eur. J. Immunol.*, 2000, vol. 30, pp. 3165-3170.

Robert, B., et al., "Redirecting anti-viral CTL against cancer cells by surface targeting of monomeric MHC class I-viral peptide conjugated to antibody fragments," *Cancer Immunity*, 2001, vol. 1. p. 2.

Rongcun, Y., et al., "Identification of New HER2/neu-Derived Peptide Epitopes That Can Elicit Specific CTL Against Autologous and Allogeneic Carcinomas and Melanomas," *J. Immunol.*, 1999, vol. 163, pp. 1037-1044.

Rötzschke, O., et al., "Superactivation of an immune response triggered by oligomerized T cell epitopes," *Proc. Natl. Acad. Sci. USA*, 1997, vol. 94, pp. 14642-14647.

Rötzschke, O., et al., "Conformational variants of class II MHC/peptide complexes induced by N- and C-terminal extensions of minimal peptide epitopes," *Proc. Natl. Acad. Sci. USA*, 1999, vol. 96, pp. 7445-7450.

Salazar-Onfray, F., et al., "Synthetic Peptides Derived from the Melanocyte-stimulating Hormone Receptor MC1R Can Stimulate HLA-A2-restricted Cytotoxic T Lymphocytes that Recognize Naturally Processed Peptides on Human Melanoma Cells," *Cancer Res.*, 1997, vol. 57, pp. 4348-4355.

Salter, R. D., et al., "A binding site for the T-cell co-receptor CD8 on the $\alpha_3$domain of HLA-A2," *Nature*, 1990, vol. 345, pp. 41-46.

Saubermann, L. J., et al., "Activation of Natural Killer T Cells by $\alpha$-Galactosylceramide in the Presence of Cd1d Provides Protection Against Colitis in Mice," *Gastroenterology*, 2000, vol. 119, pp. 119-128.

Schmitt, L., et al., "Catalysis of peptide dissociation from class II MHC-peptide complexes," *Proc. Natl. Acad. Sci. USA*, 1999, vol. 96, pp. 6581-6586.

Schnell, S., et al., "Retrovirally Transduced Mouse Dendritic Cells Require CD4$^+$T Cell Help to Elicit Antitumor Immunity: Implications for the Clinical Use of Dendritic Cells," *J. Immunol.*, 2000, vol. 164, pp. 1243-1250.

Schwartz, M., and Kipnis, J., "Multiple Sclerosis as a By-Product of the Failure to Sustain Protective Autoimmunity: A Paradigm Shift," *The Neuroscientist*, 2002, vol. 8, No. 5, pp. 405-413.

Sege, K., et al., "Role of $\beta_2$-Microglobulin in the Intacellular Processing of HLA Antigens," *Biochemistry*, 1981, vol. 20, pp. 4523-4530.

Shi, K., et al., "Lymphoid Chemokine B Cell-Attracting Chemokine-1 (CXCL13) Is Expressed in Germinal Center of Ectopic Lymphoid Follicles Within the Synovium of Chronic Arthritis Patients," *J. Immunol.*, 2001, vol. 166, pp. 650-655.

Sidney, J., et al., "Practical, biochemical and evolutionary implications of the discovery of HLA class I supermotifs," *Immunol. Today*, 1996, vol. 17, No. 6, pp. 261-266.

Sidney, J., et al., "Majority of Peptides Binding HLA-A*0201 With High Affinity Crossreact With Other A2-Supertype Molecules," *Human Immunol.*, 2001, vol. 62, pp. 1200-1216.

Singh, A. K., et al., "Natural Killer T Cell Activation Protects Mice Against Experimental Autoimmune Encephalomyelitis," *J. Exp. Med.*, 2001, vol. 194, No. 12, pp. 1801-1811.

Singh, A. K., et al., "The natural killer T cell ligand $\alpha$-galactosylceramide prevents or promotes pristane-induced lupus in mice," *NIH Public Access, Author Manuscript, Eur J. Immunol.*, 2005, vol. 35(4), pp. 1143-1154.

Smyth, M. J., et al., "Sequential production of interferon-$\gamma$ by NK1.1$^+$T cells and natural killer cells is essential for the antimetastatic effect of $\alpha$-galactosylceramide," *Blood*, 2002, vol. 99, pp. 1259-1266.

Smyth, M., et al., "Sequential activation of NKT cells and NK cells provides effective innate immunotherapy of cancer," *The Journal of Experimental Medicine*, 2005, vol. 201, No. 12, pp. 1973-1985.

Springer, T. A. And Strominger, J. L., "Detergent-soluble HLA antigens contain a hydrophilic region at the Cooh-terminus and a penultimate hydrophobic region," *Proc. Natl. Acad. Sci. USA*, 1976, vol. 73, No. 7, pp. 2481-2485.

Steller, Michael A., et al., "Cell-mediated Immunological Responses in Cervical and Vaginal Cancer Patients Immunized with a Lipidated Epitope of Human Papillomavirus Type 16 E7," *Clinical Cancer Research*, 1998, vol. 4, 2103-2109.

Stirnemann, K., et al., "Sustained activation and tumor targeting of NKT cells using a CD1d-anti-HER2-scFv fusion protein induce antitumot effects in mice, " *J. Clin. Invest.*, 2008, vol. 118, No. 3, pp. 994-1005.

Stronge, V.S., et al., "A closer look at CD1d molecules: new horizons in studying NKT cells," *TREND: In Immunology*, 2007, vol. 28, No. 10, 455-462.

Sumida, T., et al., "Selective Reduction of T Cells Bearing Invariant V$\alpha$24J$\alpha$Q Antigen Receptor in Patients with Systemic Sclerosis," *J. Exp. Med.*, 1995, vol. 182, pp. 1163-1168.

Tahir, S. M. A., et al., "Loss of IFN, Production of Invariant NK T Cells in Advanced Cancer," *The Journal of Immunology*, 2001, 167:4046-4050.

Takahashi, T., et al., "707-AP Peptide Recognized by Human Antibody Induces Human Leukocyte Antigen A2-restricted Cytotoxic T Lymphocyte Killing of Melanoma," *Clin. Cancer Res.*, 1997, vol. 3, pp. 1363-1370.

Takahashi, T., et al., "Cytotoxic T lymphocytes that recognize decameric peptide sequences of retinoblastoma binding protein 1 (RBP-1) associated with human breast cancer," *British J. Cancer*, 1999, vol. 81, No. 2, pp. 342-349.

Takeda, K., et al., "Relative contribution of NK and NKT cells to the anti-metastatic activities of IL-12," *Int. Immunol.*, 2000, vol. 12, No. 6, pp. 909-914.

(56) References Cited

OTHER PUBLICATIONS

Taniguchi, M., et al., "The NKT cell system: bridging innate and acquired immunity," *Nature Immunology*, 2003, vol. 4, No. 32, 1164-5.

Tanzarella, S., et al., "Identification of a Promiscuous T-Cell Epitope Encoded by Multiple Members of the *MAGE*Family," *Cancer Res.*, 1999, vol. 59, pp. 2668-2674.

Timmerman, J. M., et al., "Dendritic Cell Vaccines for Cancer Immunotherapy," *Annu. Rev. Med.*, 1999, vol. 50, pp. 507-529.

Tisch, R., and McDevitt, H.O., "Antigen-specific immunotherapy: Is it a real possibility to combat T-cell-mediated autoimmunity?" *Proc. Natl. Acad. Sci. USA*, 1994, vol. 91, pp. 437-438.

Turkewitz, A. P., et al., "Large-Scale Purificaton of Murine I-$A^k$ and I-$E^k$ Antigens and Characteristics of Purified Proteins," *Molecular Immunol.*, 1983, vol. 20, No. 11, pp. 1139-1147.

Turner, M. J., et al., "Purification of Papain-solubilized Histocompatibility Antigens from a Cultured Human Lymphoblastoid Line, RPMI 4265*," *J. Biol. Chem.*, 1975, vol. 250, No. 12, pp. 4512-4519.

Valmori, D., et al., "Analysis of MAGE-3-specific Cytolytic T Lymphocytes in Human Leukocyte Antigen-A2 Melanoma Patients," *Cancer Res.*, 1997, vol. 57, pp. 735-741.

Valmori, D., et al., "Diversity of the Fine Specificity Displayed by HLA-A*0201-Restricted CTL Specific for the Immunodominant Melan-A/MART-1 Antigenic Peptide," *J. Immunol.*, 1998, vol. 161, pp. 6956-6962.

Valmori, D., et al., "Analysis of the Cytolytic T Lymphocyte Response of Melanoma Patients to the Naturally HLA-A*0201-associated Tyrosinase Peptide 368-376," *Cancer Res.*, 1999, vol. 59, pp. 4050-4055.

Van Der Vliet, H. J. J., et al., "Circulating V$\alpha$24$^+$V$\beta$11$^+$NKT Cell Numbers Are Decreased in a Wide Variety of Diseases That Are Characterized by Autoreactive Tissue Damage," *Clin. Immunol.*, 2001, vol. 100, No. 2, pp. 144-148.

Van Kaer, L.V., "NKT cells: T lymphocytes with innate effector functions," *Current Opinion in Immunology*, 2007, vol. 19, pp. 354-364.

Wang, B., et al., "CD1-restricted NK T Cells Protect Nonobese Diabetic Mice from Developing Diabetes," *J. Exp. Med.*, 2001, vol. 194, No. 3, pp. 313-319.

Wang, R-F., et al., "Recognition of an Antigenic Peptide Derived from Tyrosinase-Related Protein-2 by CTL in the Context of HLA-A31 and -A33," *J. Immunol.*, 1998, vol. 160, pp. 890-897.

Whitman, M. C., et al., "The isolated major histocompatibility complex class I $\alpha$3 domain binds $\beta$2m and CD8$\alpha\alpha$ dimers," *Molecular Immunology*, 2000, vol. 37, pp. 141-149.

Wilson, M. T., et al., "Immunotherapy with ligands of natural killer T cells," *TRENDS in Molecular Med.*, 2002, vol. 8, No. 5, pp. 225-231.

Wizel, B., et al., "HLA-A2 Restricted Cytotoxic T Lymphocyte Responses to Multiple *Plasmodium falciparum*Sporozoite Surface Protein 2 Epitopes in Sporozoite-Immunized Volunteers," *J. Immunol.*, 1995, vol. 155, pp. 766-775.

Wizel, B., et al., "Human Infection with *Trypanosoma cruzi*Induces Parasite Antigen- Specific Cytotoxic T Lymphocyte Responses," *J. Clin. Invest.*, 1998, vol. 102, pp. 1062-1071.

Yu, K. O. A., et al., "Production and characterization of monoclonal antibodies against complexes of the NKT cell ligand $\alpha$-galactosylceramide bound to mouse CD1d," *J. Immunological Methods.*, 2007, vol. 323, pp. 11-23.

Zarour, H. M., et al., "Melan-A/MART-$1_{51-73}$represents an immunogenic HLA-DR4-restricted epitope recognized by melanoma-reactive CD4$^+$T cells," *PNAS*, 2000, vol. 97, No. 1, pp. 400-405.

Zarutskie, J. A., et al., "A Conformational Change in the Human Major Histocompatibility Complex Protein HLA-DR1 Induced by Peptide Binding," *Biochemistry*, 1999, vol. 38, pp. 5878-5887.

Zemon, H., "An artificial solution for adoptive immunotherapy," *TRENDS in Biotechnology*, 2003, vol. 21, No. 10, pp. 418-420.

Zhang, H., et al., "Targeting of functional antibody-CD59 fusion proteins to a cell surface," *The Journal of Clinical Investigation*, 1999, vol. 103, No. 1, pp. 55-61.

Zhu, X., et al., "A recombinant single-chain human class II MHC molecule (HLA-DR1) as a covalently linked heterotrimer of a chain, $\beta$ chain, and antigenic peptide, with immunogenicity in vitro and reduced affinity for bacterial superantigens," *European Journal of Immunology*, 1997, vol. 27, pp. 1933-1941.

Parekh, V. V., et al., "Quantitative and Qualitative Differences in the in Vivo Response of NKT Cells to Distinct Alpha- and Beta-Anomeric Glycolipids," *The Journal of Immunology*, 2004, pp. 3693-3706, vol. 173(6).

Shi, F-D., et al., "Germ line deletion of the CD1 locus exacerbates diabetes in the NOD mouse," *Proceedings of the National Academy of Sciences of the United States of America*, 2001, pp. 6777-6782, vol. 98(12).

* cited by examiner

BACTERIAL VACCINES WITH CELL WALL-ASSOCIATED CERAMIDE-LIKE GLYCOLIPIDS AND USES THEREOF

STATEMENT AS TO FEDERALLY-SPONSORED RESEARCH

This invention was made with government support under grant No. AI063537 awarded by National Institutes of Health (NIH). The government has certain rights in the invention.

REFERENCE TO SEQUENCE LISTING SUBMITTED ELECTRONICALLY

The content of the electronically submitted sequence listing ("sequencelisting.ascii.txt", 1,245 bytes, created on Jan. 7, 2010) filed with the application is incorporated herein by reference in its entirety.

BACKGROUND OF THE INVENTION

1. Field of the Invention

The invention generally relates to the field of immunology.

2. Background Art

Mycobacterium are known to cause serious diseases in mammals, e.g., tuberculosis, Hansen's disease, leprosy, pulmonary disease resembling tuberculosis, lymphadenitis, skin disease, or disseminated disease. A third of the world's population is infected with Mycobacterium tuberculosis, and 2 million people die from tuberculosis (TB) every year even though the bacille Calmette Guérin (BCG) vaccine has been available for more than 75 years. Hoft D F, Lancet 372: 164-175 (2008). Tuberculosis is currently the second highest cause of death from an infectious disease worldwide, after HIV/AIDS. Young D B et al., Journal of Clinical Investigation 118: 1255-1265 (2008).

Several studies suggest that both MHC class I- and II-restricted T cells are required for effective control of M. tuberculosis infection. Mogues T et al., J Exp Med 193: 271-280 (2001) and Flynn J L et al., Proc Natl Acad Sci USA 89: 12013-12017 (1992). However, mice that are deficient in the lipid-antigen presenting molecule, CD1d, are not more susceptible than wild-type mice to M. tuberculosis infection, indicating that CD1d-restricted NKT cells are not absolutely required for protective immunity. Behar S M et al., J Exp Med 189: 1973-1980 (1999). Natural killer T (NKT) cells represent a subset of T lymphocytes expressing both T-cell receptor and NK-cell receptor, and play a role in bridging innate immunity to adaptive immunity. Kronenberg M and Gapin L, Nat Rev Immunol 2: 557-568 (2002). Upon activation, NKT cells can have a pronounced impact on early and delayed immunity to various pathogens, including L. monocytogenes, M. tuberculosis and Leishmania major. Kronenberg (2002); Behar S M and Porcelli S A, Curr Top Microbiol Immunol 314: 215-250 (2007); Emoto M et al., Eur J Imtnunol 29: 650-659 (1999); Ishikawa H et al., Int Immunol 12: 1267-1274 (2000); and Ranson T et al., J Immunol 175: 1137-1144 (2005). NKT cell activation has been reported to lead to enhanced CD4 and CD8 T cell responses, and to induce dendritic cell maturation. Nishimura T et al., Int Immunol 12: 987-994 (2000) and Silk J D et al., J Clin Invest 114: 1800-1811 (2004).

Unlike conventional T cells that recognize MHC-bound peptides, NKT cells are specific for lipid antigens presented by the MHC class I-like protein CD1d. Several glycolipid antigens, including self-derived and bacterial-derived glycolipids, which can be presented by CD1d to activate NKT cells, have been identified to date. Tsuji M Cell Mol Life Sci 63: 1889-1898 (2006). NKT cells that have T-cell receptors with invariant Vα14-Jα18 rearrangements (iNKT cells) possess reactivity to a glycosphingolipid, α-galactosylceramide (αGalCer), when presented by CD1d. Kronenberg M and Gapin L, Nat Rev Immunol 2: 557-568 (2002); Kronenberg M, Annu Rev Immunol 23: 877-900 (2005). Recent studies have shown that vaccines against Plasmodia, Leishmania donovanii, Listeria monocytogenes and HIV could be improved by activating iNKT cells through co-administration of αGalCer as an adjuvant. Gonzalez-Aseguinolaza G et al., J Exp Mal 195: 617-624 (2002); Dondji B et al., European Journal of Immunology 38: 706-719 (2008); Huang Y X et al., Vaccine 26: 1807-1816 (2008); and Enomoto N et al., FEMS Immunol Med Microbiol 51: 350-362 (2007).

As a therapeutic, αGalCer has been shown to reduce malarial parasite load in mice and prolong the survival of M. tuberculosis infected mice. Gonzalez-Aseguinolaza G et al., Proc Natl Acad Sci USA 97: 8461-8466 (2000); Chackerian A et al., Infection and Immunity 70: 6302-6309 (2002). Thus, although CD1d-restricted T cells are not absolutely required for optimum immunity, their specific activation enhances host resistance to infectious diseases.

A single injection of αGalCer in mice induces a cytokine storm in the serum resulting in secretion of IFNγ, IL-12 and IL-4. Fujii S et al., Immunol Rev 220: 183-198 (2007). Stimulation of CD1d-restricted iNKT cells by αGalCer also leads to rapid activation of NK cells, dendritic cells, B cells, and conventional T cells. Nishimura T et al., Int Immunol 12: 987-994 (2000); Kitamura H et al., J Exp Med 189: 1121-1128 (1999); Fujii S et al., J Exp Med 198: 267-279 (2003). iNKT cells produce large amounts of IFNγ and the production requires direct contact between iNKT cells and DCs through CD40-CD40 ligand interactions. Nishimura T et al., Int Immunol 12: 987-994 (2000). IFNγ produced by iNKT cells has been shown to have a critical role in the antimetastatic effect of αGalCer in murine tumor models. Hayakawa Y et al., Eur J Immunol 31: 1720-1727 (2001); Smyth M J et al., Blood 99: 1259-1266 (2002). Thus, it has been proposed that activation of iNKT cells can modulate adaptive immune responses by influencing the early cytokine environment.

Recently, a C-glycoside analogue of αGalCer known as the α-C-GalCer has been established as a predominant Th1 skewing compound which has a superior anti-tumor and anti-malarial activity as compared to αGalCer in mice. This compound also induces higher levels of Th1 cytokines IL-12 and IFNγ in mice. Schmieg J et al., Journal of Experimental Medicine 198: 1631-1641 (2003). It has been established that these two cytokines, IL-12 and IFNγ, are essential for control of TB in mice and humans. Freidag B L et al., Infect Immun 68: 2948-2953 (2000).

Very few studies exist on the use of adjuvants with BCG vaccine in the mouse model against tuberculosis. One such study reported an enhanced protection against M. tuberculosis challenge when CpG ODN was used along with BCG vaccination. Freidag B L et al., Infect Immun 68: 2948-2953 (2000). Most of the earlier studies on the adjuvant effect of αGalCer with vaccines against various infectious diseases have utilized separate co-administration of αGalCer with the respective vaccine in order to harness its adjuvant activity. Gonzalez-Aseguinolaza G et al. (2002); Dondji B et al. (2008); Huang Y X et al. (2008); and Enomoto N et al. (2007). Thus, there remains a need for effective compositions and vaccines for enhancing immune responses to bacterial, e.g., mycobacterial, antigens.

SUMMARY OF THE INVENTION

The present invention is directed to a modified bacterium comprising a bacterial cell and a ceramide-like glycolipid, wherein the ceramide-like glycolipid is physically associated with the bacterial cell. In a further embodiment, the ceramide-like glycolipid comprises a glycosylceramide or an α-galactosylceramide or analogs thereof.

In one embodiment, the glycosylceramide or analog thereof comprises Formula I:

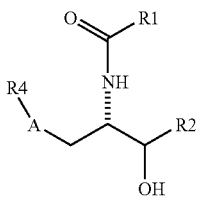

(Formula I)

wherein R1 is a linear or branched $C_1$-$C_{27}$ alkane or $C_2$-$C_{27}$ alkene; or R1 is —C(OH)—R3 wherein R3 is a linear or branched $C_1$-$C_{26}$ alkane or $C_2$-$C_{26}$ alkene; or R1 is a $C_6$-$C_{27}$ alkane or alkene wherein (i) the $C_6$-$C_{27}$ alkane or alkene is substituted with a $C_5$-$C_{15}$ cycloalkane, $C_5$-$C_{15}$ cycloalkene, heterocycle, or aromatic ring or (ii) the $C_6$-$C_{27}$ alkane or alkene includes, within the $C_6$-$C_{27}$ alkyl or alkenyl chain, a $C_5$-$C_{15}$ cycloalkane, $C_5$-$C_{15}$ cycloalkene, heterocycle, or aromatic ring;

R2 is one of the following (a)-(e):
(a) —$CH_2(CH_2)_xCH_3$,
(b) —$CH(OH)(CH_2)_xCH_3$,
(c) —$CH(OH)(CH_2)_xCH(CH_3)_2$,
(d) —CH═$CH(CH_2)_xCH_3$,
(e) —$CH(OH)(CH_2)_xCH(CH_3)CH_2CH_3$,
wherein X is an integer ranging from 4-17;

R4 is an α-linked or a β-linked monosaccharide, or when R1 is a linear or branched $C_1$-$C_{27}$ alkane, R4 is:

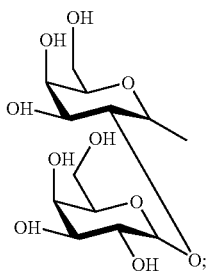

and A is O or —$CH_2$.

In one embodiment, the α-galactosylceramide or analog thereof comprises Formula II:

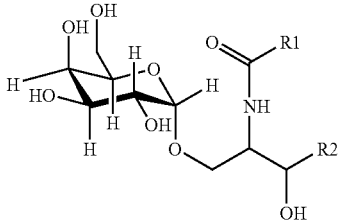

(Formula II)

wherein
R1 is a linear or branched $C_1$-$C_{27}$ alkane or $C_2$-$C_{27}$ alkene; or R1 is —C(OH)—R3 wherein R3 is linear or branched $C_1$-$C_{26}$ alkane or $C_2$-$C_{26}$ alkene; and R2 is one of the following (a)-(e):
(a) —$CH_2(CH_2)_xCH_3$,
(b) —$CH(OH)(CH_2)_xCH_3$,
(c) —$CH(OH)(CH_2)_xCH(CH_3)_2$,
(d) —CH═$CH(CH_2)_xCH_3$,
(e) —$CH(OH)(CH_2)_xCH(CH_3)CH_2CH_3$,
wherein X is an integer ranging from 4-17.

In one embodiment, the α-galactosylceramide or analog thereof comprises Formula III:

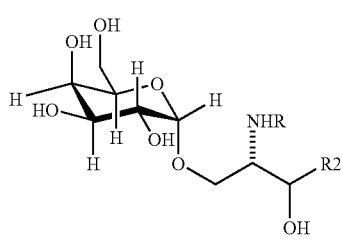

(Formula III)

wherein R is H or —C(O)R1, wherein R1 is a linear or branched $C_1$-$C_{27}$ alkane or $C_7$-$C_{27}$ alkene; or R1 is —C(OH)—R3 wherein R3 is a linear or branched $C_1$-$C_{26}$ alkane or $C_2$-$C_{26}$ alkene; or R1 is a $C_6$-$C_{27}$ alkane or alkene wherein (i) the $C_6$-$C_{27}$ alkane or alkene is substituted with a $C_5$-$C_{15}$ cycloalkane, $C_5$-$C_{15}$ cycloalkene, heterocycle, or aromatic ring or (ii) the $C_6$-$C_{27}$ alkane or alkene includes, within the $C_6$-$C_{27}$ alkyl or alkenyl chain, a $C_5$-$C_{15}$ cycloalkane, $C_5$-$C_{15}$ cycloalkene, heterocycle, or aromatic ring; or R1 is —$(CH_2)_n$R5, wherein n is an integer ranging from 0-5, and R5 is —$C(O)OC_2H_5$, an optionally substituted $C_5$-$C_{15}$ cycloalkane, an optionally substituted aromatic ring, or an aralkyl, and R2 is one of the following (a)-(e):
(a) —$CH_2(CH_2)_xCH_3$,
(b) —$CH(OH)(CH_2)_xCH_3$,
(c) —$CH(OH)(CH_2)_xCH(CH_3)_2$,
(d) —CH═$CH(CH_2)_xCH_3$,
(e) —$CH(OH)(CH_2)_xCH(CH_3)CH_2CH_3$,
wherein X is an integer ranging from 4-17.

In one embodiment, a ceramide-like glycolipid is incorporated into the cell wall of a bacterial cell. In a further embodiment, the bacterial cell is selected from the group consisting of a mycobacterial cell, a *Listeria* cell, a *Salmonella* cell, a *Yersinia* cell, a *Francisella* cell, and a *Legionella* cell. In another embodiment, the bacterial cell is live, killed, or attenuated.

In one embodiment, the modified bacterium enhances antigen-specific CD8 T cell responses against an antigen. In a further embodiment, the antigen is a mycobacterial antigen.

In one embodiment, the modified bacterium expresses a heterologous antigen. In a further embodiment, the heterologous antigen is a viral antigen, a bacterial antigen, a fungal antigen, a parasitic antigen, or a tumor specific antigen. In another embodiment, the heterologous antigen is an immunogenic peptide.

In one embodiment, the bacterial cell is a recombinant bacterial cell.

The present invention is also directed to a composition comprising a modified bacterium and a pharmaceutical carrier. In one embodiment, the pharmaceutical carrier is selected from the group consisting of saline, buffered saline, dextrose, water, glycerol, and combinations thereof. In another embodiment, the composition further comprises an adjuvant. In another embodiment, the composition is a vaccine composition.

The present invention is also directed to methods of treating or preventing a disease in an animal, comprising administering to an animal in need of treatment or prevention a modified bacterium. In one embodiment, the modified bacterium is administered in an amount sufficient to alter the progression of the disease. In another embodiment, the modified bacterium is administered in an amount sufficient to induce an immune response in the animal against the disease.

In one embodiment, an immune response is enhanced or modified relative to an immune response produced by a bacterial cell not associated with a ceramide-like glycolipid. In one embodiment, the disease is selected from the group consisting of a viral disease, a bacterial disease, a fungal disease, a parasitic disease, and a proliferative disease. In a further embodiment, the disease is selected from the group consisting of tuberculosis, pulmonary disease resembling tuberculosis, lymphadenitis, skin disease, disseminated disease, bubonic plague, pneumonic plague, tularemia, Legionairre's disease, anthrax, typhoid fever, paratyphoid fever, foodborne illness, listeriosis, malaria, Human Immunodeficiency Virus (HIV), Simian Immunodeficiency Virus (SIV), Human Papilloma Virus (HPV), Respiratory Syncitial Virus (RSV), influenza, hepatitis (HAV, HBV, and HCV), and cancer.

The present invention is also directed to a method of inducing an immune response against an antigen in an animal, comprising administering to the animal a modified bacterium. In one embodiment, the modified bacterium is administered in an amount sufficient to enhance an antigen-specific CD8 T-cell response or enhance the activity of Natural Killer T (NKT) cells in the animal. In another embodiment, the immune response comprises an antibody response. In another embodiment, the immune response comprises a CD8 T-cell response. In another embodiment, the immune response comprises a CD8 T-cell response and an antibody response.

The present invention is also directed to a method of modulating a CD8 T-cell response to BCG in an animal comprising administering to the animal an effective amount of a modified bacterium.

In one embodiment, the modified bacterium is administered by a route selected from the group consisting of intramuscularly, intravenously, intratracheally, intranasally, transdermally, intradermally, subcutaneously, intraocularly, vaginally, rectally, intraperitoneally, intraintestinally, by inhalation, or by a combination of two or more of said routes.

The present invention is also directed to a kit comprising a modified bacterium. In one embodiment, the modified bacterium is lyophilized. In a further embodiment, the kit comprises a means for administering the modified bacterium.

The present invention is also directed to method of making a ceramide-like glycolipid/mycobacterial complex comprising (a) culturing a mycobacterial cell in culture medium and (b) adding a ceramide-like glycolipid to the culture medium under conditions where said ceramide-like glycolipid incorporates to the cell wall of said mycobacterial cell.

In one embodiment, the invention is directed to a method of producing a vaccine against an antigen comprising: (a) isolating a ceramide-like glycolipid/mycobacterial complex and (b) adding a pharmaceutical carrier to the isolated complex of (a).

These and other aspects of the invention are described in further detail below.

DETAILED DESCRIPTION OF THE INVENTION

Figure 1:
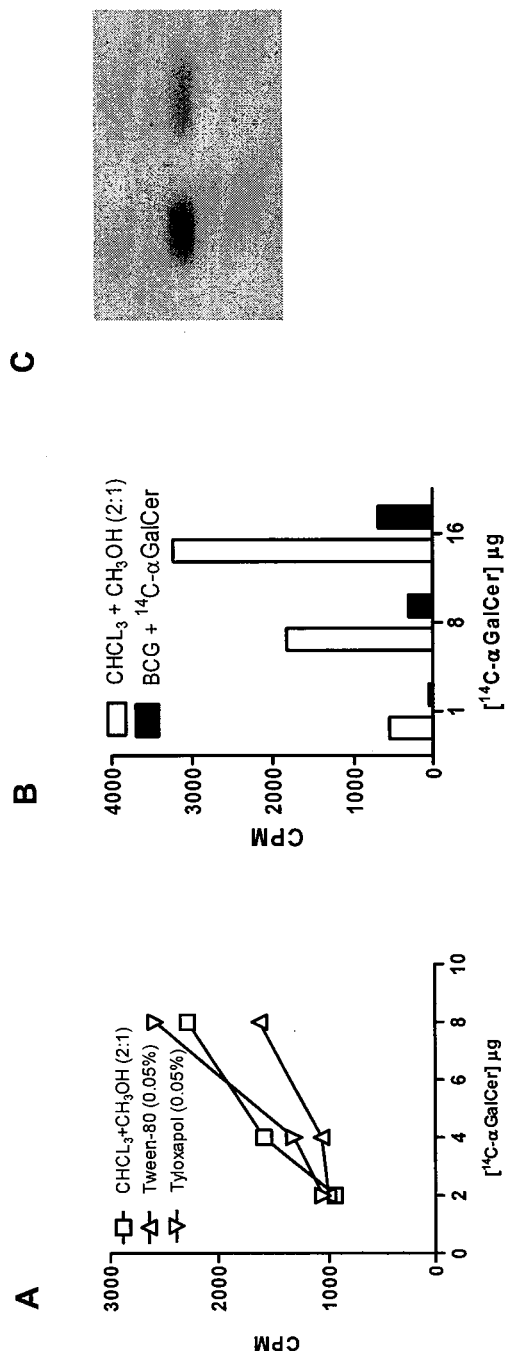
FIG. 1: Stable incorporation of αGalCer into the *M. bovis* BCG cell wall. (A) Graph showing the solubility of $^{14}$C-αGalCer in $CHCl_3+CH_3OH$ (2:1), Phosphate buffered saline (PBS)+0.05% Tween 80, or 0.05% Tyloxapol. (B) Graph showing incorporation of $^{14}$C-αGalCer into *M. bovis* BCG grown in presence of different concentrations of $^{14}$C-αGalCer in protein-free Middlebrooks 7H9 medium with 0.05% Tyloxapol. (C) Thin-layer chromatography bands of cell wall lipid extracted from *M. bovis* BCG grown in presence of $^{14}$C-αGalCer in protein-free Middlebrooks 7H9 medium with 0.05% Tyloxapol, Lane 1: $^{14}$C-αGalCer dissolved directly in Chloroform-methanol 2:1. Lane 2: $^{14}$C-αGalCer extracted from *M. bovis* BCG.

The present invention provides compositions, isolated cells, vaccines, and methods which are useful for enhancing, i.e., eliciting, stimulating or increasing, an immune response. Described herein is a modified bacterium comprising a ceramide-like glycolipid physically physically associated with a bacterial cell, e.g., ceramide-like glycolipids stably incorporated into a bacterial cell wall, e.g., a mycobacterial cell wall. Ceramide-like glycolipid/bacterial complexes of the present invention can enhance an immune response by affecting the activity of CD1d-restricted natural killer T ("NKT") cells. In certain embodiments, the compositions, e.g., vaccine compositions, of the invention include an α-galactosylceramide or analog thereof incorporated into the cell wall of *M. bovis* bacille Calmette-Guerin (BCG). Ceramide-like glycolipid/bacterial complexes as described herein are useful for stimulating desirable immune responses, for example, immune responses against mycobacterial antigens. The immune response can be useful for preventing, treating or ameliorating diseases caused by bacterial pathogens, e.g., mycobacteria, e.g., *Mycobacterium tuberculosis*, which causes TB in humans.

Advantages of the invention also include that delivery of ceramide-like glycolipid adjuvants directly to the same cells that become infected with a bacteria, e.g., a live attenuated bacteria, allows the focusing of the adjuvant in a way that permits much smaller doses to be used. Thereby reducing local and systemic toxicity and lowering production costs. In addition, physically linking, e.g., direct incorporation, has practical advantages, particularly for vaccines that target populations in the third world where there are delivery and storage issues. Bacteria physically associated, e.g., directly incorporated, with ceramide-like glycolipids which are lyophilized and then reconstituted should allow for adjuvant activity to be recovered intact. Thus, the lyophilized vaccine could be rehydrated and suspended in the field for administration.

DEFINITIONS

It is to be noted that the term "a" or "an" entity refers to one or more of that entity; for example, "a vector" is understood to represent one or more vectors. As such, the terms "a" (or "an"), "one or more," and "at least one" can be used interchangeably herein.

As discussed in more detail below, the present invention includes a glycolipid, typically a ceramide-like glycolipid, e.g., an α-galactosylceramide, also referred to herein as α-GalCer, or an analog thereof, such as α-C-GalCer, physically associated with a bacterial cell, e.g., incorporated into a bacterial cell wall, e.g., a mycobacterial cell wall. In certain embodiments, the ceramide-like glycolipid is physically associated through non-covalent interactions. "Ceramide-like glycolipids," as referred to herein include glycolipids with α-linked galactose or glucose. Examples of ceramide-like glycolipids are described herein and also can be found, e.g., in Porcelli, U.S. Patent Appl. Publ. No. 2006/0052316, Tsuji, U.S. Patent Appl. Publ. No. 2006/0211856, Jiang, U.S. Patent Appl. Publ. No. 2006/0116331, Hirokazu et al., U.S. Patent Appl. Publ. No. 2006/0074235, Tsuji et al., U.S. Patent Appl. Publ. No. 2005/0192248, Tsuji, U.S. Patent Application No. 2004/0127429, and Tsuji et al., U.S. Patent Application No. 2003/0157135, all of which are incorporated by reference herein in their entireties.

Vaccines

The term "vaccine" refers to a composition, which when administered to an animal is useful in stimulating an immune response, e.g., against an infection, e.g., a mycobacterial infection. The invention relates to a vaccine composition comprising bacterial cells, e.g., mycobacterial cells, wherein said cells can be killed, live and/or attenuated, for example, BCG, which is a live attenuated bacterial vaccine. Bacterial vaccines, e.g., live bacterial vaccines, killed bacterial vaccines, or attenuated bacterial vaccines are known in the art or can be produced by methods well known to a person of ordinary skill in the art using routine experimentation. A bacterial vaccine of the invention can also include recombinant bacteria, e.g., a recombinant mycobacteria.

In certain embodiments, a bacterial cell and a ceramide-like glycolipid are co-administered. In one embodiment, a bacterial cell is modified, e.g., "glycolipid modified" to physically link a glycolipid to the bacterial cell, e.g., a ceramide-like glycolipid is incorporated into the cell wall of a bacterial cell, e.g., a mycobacterial cell.

In another embodiment, glycolipid modified bacterial cells of the invention can be used as carriers for the delivery of heterologous antigens, e.g., immunogenic polypeptides. For example, a glycolipid modified bacterial cell, e.g., a recombinant bacterial cell having a ceramide-like glycolipid incorporated into its cell wall can be used as a carrier for the delivery of antigens from another pathogen (e.g., bacterial (e.g., *Salmonella, Listeria, Bacillus anthraicis*, and *Shigella* antigens), fungal, parasitic (e.g., a malarial antigen from *Plasmodium*), or viral antigens (e.g., a viral antigen from HIV, SIV, HPV, RSV, influenza or hepatitis (HAV, HBV, and HCV)) or tumor specific antigens.

In one embodiment, modified bacteria of the invention include modified mycobacterial cells, e.g., *M. bovis* bacille Calmette-Guérin (BCG) cells to which α-GalCer has been stably non-covalently incorporated. BCG is a live attenuated bacterial vaccine. Albert Calmette and Camille Guérin of the Pasteur Institute attenuated *mycobacterium* related to *Mycobacterium bovis*, which is closely related to *M. tuberculosis*, to produce *Mycobacterium bovis* bacillus Calmette-Guérin (BCG) by growing it in culture medium for 13 years, and monitoring its decrease in virulence in animals through this period. BCG has become one of the most widely used of all vaccines, being both inexpensive and safe. However, the BCG vaccine has had limited effect against the epidemic of TB in the developing world. Doherty T and Anderson P, *Clinical Microbio Reviews* 18(4):687-702 (2005). In another embodiment, the mycobacterial cells are *M. smegmatis* cells, which is another nonpathogenic strain of mycobacteria that can be administered to mammals without causing disease.

In addition to modified mycobacterial cells, other modified bacteria of the invention include, without limitation glycolipid modified bacteria derived from *Bacillus* species (e.g., *Bacillus anthracis* causing anthrax), *Salmonella* species (e.g., causing typhoid fever, paratyphoid fever, foodborne illness), *Staphylococcus* species, *Streptococcus* species, *Listeria* species (e.g., causing listeriosis), *Shigella* species, *Yersinia* species (e.g., causing bubonic and pneumonic plague), *Francisella* species (e.g., causing tularemia), and *Legionella* species (e.g., causing Legionnaire's disease).

The term "antigen" and the related term "antigenic" as used herein refer to a substance that binds specifically to an antibody or to a T-cell receptor.

The term "immunogen" and the related term "immunogenic" as used herein refer to the ability to induce an immune response, including an antibody and/or a cellular immune response in an animal, for example a mammal. It is likely that an immunogen will also be antigenic, but an "antigen," because of its size or conformation, may not necessarily be an "immunogen." An "immunogenic composition" induces an immune response in a subject, e.g., antibodies that specifically recognize one or more antigens, contained within that "immunogenic composition."

The term "immune response" is meant to include an activity of cells of the immune system in response to an antigen or immunogen. Such activities include, but are not limited to production of antibodies, cytotoxicity, lymphocyte proliferation, release of cytokines, inflammation, phagocytosis, antigen presentation, and the like. An immune response which is highly specific to a given antigen or immunogen, e.g., production of specific antibodies or production of specific T lymphocytes is referred to herein as an "adaptive immune response." An immune response which is not specific to a given antigen, e.g., release of cytokines by NK and NKT cells, is referred to herein an "innate immune response." Examples of immune responses include an antibody response or a cellular, e.g., cytotoxic T-cell, response.

The terms "protective immune response" or "therapeutic immune response" refer to an immune response to an immunogen which in some way prevents or at least partially arrests disease symptoms, side effects or progression. By "protective" is meant that the immune response is induced in a subject animal which has not contracted a disease, where the immune response alleviates, reduces, moderates or, in some cases fully prevents disease symptoms if the animal later contracts or is suceptible to that disease, e.g., exposure to *M. tuberculosis*. By "therapeutic" is meant that the immune response is induced in a subject animal which has the disease, e.g., a human with tuberculosis, where the immune response alleviates, reduces, moderates, or in some cases fully eliminates disease symptoms.

The term "modulating an immune response" is meant to refer to any way in which a given immune response is increased, decreased, or changed by a composition or treatment relative to the immune response without that composition or treatment. For example, use of an adjuvant to increase an immune response to an antigen is considered modulation of that immune response. Decrease in an immune response, e.g., prevention of autoimmunity, is also a modulation. In addition, changing an immune response, e.g., from a primary TH2 response to a primary TH1 response, is a modulation of an immune response. The present invention provides methods of modulating an immune response by administering to an animal a composition which comprises a modified bacterium, e.g., a bacterial cell with a ceramide-like glycolipid incorporated into its cell wall, e.g., a mycobacterial cell wall.

The term "adjuvant" refers to a material having the ability to (1) alter or increase the immune response to a particular antigen or (2) increase or aid an effect of a pharmacological agent. In certain embodiments, a ceramide-like glycolipid functions as an adjuvant upon simultaneous administration with a bacterial cell, e.g., a BCG, e.g., when the ceramide-like glycolipid is incorporated into the BCG cell wall. In another embodiment, a second adjuvant is included. Other suitable adjuvants include, but are not limited to, LPS derivatives (e.g., monophosphoryl lipid A (MPL)), TLR9 agonists (e.g., CPG ODNS), TLR7/8 agonists (e.g., imiquimod), cytokines and growth factors; bacterial components (e.g., endotoxins, in particular superantigens, exotoxins and cell wall components); aluminum-based salts; calcium-based salts; silica; polynucleotides; toxoids; serum proteins, viruses and virally-derived materials, poisons, venoms, imidazoquiniline compounds, poloxamers, and cationic lipids.

A great variety of materials have been shown to have adjuvant activity through a variety of mechanisms. Any compound which can increase the expression, antigenicity or immunogenicity of an immunogen is a potential adjuvant. Other potential adjuvants of the invention include, but are not limited to: glycolipids; chemokines; compounds that induces the production of cytokines and chemokines; interferons; inert carriers, such as alum, bentonite, latex, and acrylic particles; pluronic block polymers, such as TiterMax® (block copolymer CRL-8941, squalene (a metabolizable oil) and a microparticulate silica stabilizer); depot formers, such as Freunds adjuvant; surface active materials, such as saponin, lysolecithin, retinal, Quil A, liposomes, and pluronic polymer formulations; macrophage stimulators, such as bacterial lipopolysaccharide; alternate pathway complement activators, such as insulin, zymosan, endotoxin, and levamisole; non-ionic surfactants; poly(oxyethylene)-poly(oxypropylene) tri-block copolymers; mLT; MF59™; SAF; RIBI™ adjuvant system; trehalose dimycolate (TDM); cell wall skeleton (CWS); DETOX™; QS21; STIMULON™; complete Freund's adjuvant; incomplete Freund's adjuvant; macrophage colony stimulating factor (M-CSF); tumor necrosis factor (TNF); 3-O-deacylated MPL; CpG oligonucleotides; polyoxyethylene ethers, polyoxyethylene esters, and combinations of more than one adjuvant.

In certain embodiments, the adjuvant is a cytokine. A composition of the present invention can comprise one or more cytokines, chemokines, or compounds that induce the production of cytokines and chemokines. Examples include, but are not limited to granulocyte macrophage colony stimulating factor (GM-CSF), granulocyte colony stimulating factor (G-CSF), macrophage colony stimulating factor (M-CSF), colony stimulating factor (CSF), erythropoietin (EPO), interleukin 2 (IL-2), interleukin-3 (IL-3), interleukin 4 (IL-4), interleukin 5 (IL-5), interleukin 6 (IL-6), interleukin 7 (IL-7), interleukin 8 (IL-8), interleukin 10 (IL-10), interleukin 12 (IL-12), interleukin 15 (IL-15), interleukin 18 (IL-18), interferon alpha (IFN$\alpha$), interferon beta (IFN$\beta$), interferon gamma (IFN$\gamma$), interferon omega (IFN$\omega$), interferon tau (IFN$\tau$), interferon gamma inducing factor I (IGIF), transforming growth factor beta (TGF-$\beta$), RANTES (regulated upon activation, normal T-cell expressed and presumably secreted), macrophage inflammatory proteins (e.g., MIP-1 alpha and MIP-1 beta), *Leishmania* elongation initiating factor (LEIF), and Flt-3 ligand.

In certain embodiments, compositions of the invention further comprise another component, e.g., a polypeptide with immunological activity. For example, the protein with immunological activity is a costimulatory molecule, such as a toll-like receptor ("TLR"), B7.1 or B7.2. "B7" is used herein to generically refer to either B7.1 or B7.2. A costimulatory molecule, e.g., the extracellular domain of B7-1 (CD80) or B7-2 (CD86) that interacts with CD28 on T- and NK-cells can be administered as an amino terminal fusion to $\beta$2-microglobulin incorporated into the structure of a soluble CD1d complex for use in the present invention. See, e.g., WO 9964597, published 16 Dec. 1999. In certain embodiments, incorporation of a costimulatory molecule, e.g., a B7 signaling molecule, with the compositions of the invention allows more effective and prolonged activation of NKT cells by a ceramide-like glycolipid/bacterial complex of the invention.

In other embodiments, the compositions of the invention further comprise additional adjuvant components, e.g., any of the adjuvants described above, such as, LPS derivatives (e.g., MPL), TLR9 agonists (e.g., CPG ODNS), TLR7/8 agonists (e.g., imiquimod), cytokines and growth factors; bacterial components (e.g., endotoxins, in particular superantigens, exotoxins and cell wall components); aluminum-based salts; calcium-based salts; silica; polynucleotides; toxoids; serum proteins, viruses and virally-derived materials, poisons, venoms, imidazoquiniline compounds, poloxamers, cationic lipids, and Toll-like receptor (TLR) agonists. Examples of TLR agonist adjuvants which can be effective, include, but are not limited to: N-acetylmuramyl-L-alanine-D-isoglutamine (MDP), lipopolysaccharides (LPS), genetically modified and/or degraded LPS, alum, glucan, colony stimulating factors (e.g., EPO, GM-CSF, G-CSF, M-CSF, PEGylated G-CSF, SCF, IL-3, IL6, PIXY 321), interferons (e.g., $\gamma$-interferon, $\alpha$-interferon), interleukins (e.g. IL-1, IL-2, IL-3, IL-4, IL-5, IL-6, IL-10, IL-12, IL-15, IL-18), saponins (e.g., QS21), monophosphoryl lipid A (MPL), 3 De-O-acylated monophosphoryl lipid A (3D-MPL), unmethylated CpG sequences, 1-methyl tryptophan, arginase inhibitors, cyclophosphamide, antibodies that block immunosuppressive functions (e.g., anti-CTLA4 antibodies), lipids (such as palmitic acid residues), tripalmitoyl-S-glycerylcystein lyserylserine ($P_3$ CSS), and Freund's adjuvant. Alternatively or additionally, compositions of the present invention my further comprise a lymphokine or cytokine that modulates immune cell activation such as transforming growth factor (TGF, e.g., TGF$\alpha$ and IGF$\beta$); $\alpha$ interferons (e.g. IFN$\alpha$); $\beta$ interferons (e.g. IFN$\beta$); $\gamma$ interferons (e.g. IFN$\gamma$) or lymphocyte function-associated protein, such as LFA-1 or LFA-3; or an intercellular adhesion molecule, such as ICAM-1 or ICAM-2.

Compositions of the invention can further comprise an immunogenic polypeptide. In certain embodiments, glycolipid modified recombinant bacterial cells of the invention can be used as carriers for the delivery of heterologous antigens or immunogens. Heterologous antigens or immunogens can include, but are not limited to, immunogenic polypeptides. In one embodiment, the immunogenic polypeptide can be expressed by a glycolipid modified recombinant bacterial cell of the invention, e.g., immunogenic polypeptides of heterogous pathogens expressed by recombinant mycobacterial cells with a ceramide-like glycolipid incorporated into the mycobacterial cell wall.

An "immunogenic polypeptide" is meant to encompass antigenic or immunogenic polypeptides, e.g., poly-amino acid materials having epitopes or combinations of epitopes. As used herein, an immunogenic polypeptide is a polypeptide which, when introduced into a vertebrate, reacts with the immune system molecules of the vertebrate, i.e., is antigenic, and/or induces an immune response in the vertebrate, i.e., is immunogenic. It is likely that an immunogenic polypeptide will also be antigenic, but an antigenic polypeptide, because of its size or conformation, may not necessarily be immunogenic. Examples of antigenic and immunogenic polypeptides include, but are not limited to, polypeptides from infectious agents such as bacteria, viruses, parasites, or fungi, allergens such as those from pet dander, plants, dust, and other environmental sources, as well as certain self-polypeptides, for example, tumor-associated antigens.

Antigenic and immunogenic polypeptides of the invention can be used to prevent or treat, e.g., cure, ameliorate, lessen the severity of or prevent or reduce contagion of viral, bacterial, fungal, and parasitic infectious diseases, as well as to treat allergies and proliferative diseases such as cancer.

In addition, antigenic and immunogenic polypeptides of the invention can be used to prevent or treat, e.g., cure, ameliorate, or lessen the severity of cancer including, but not limited to, cancers of oral cavity and pharynx (e.g., tongue, mouth, pharynx), digestive system (e.g., esophagus, stomach, small intestine, colon, rectum, anus, anal canal, anorectum, liver, gallbladder, pancreas), respiratory system (e.g., larynx, lung), bones, joints, soft tissues (including heart), skin, melanoma, breast, reproductive organs (e.g., cervix, endometirum, ovary, vulva, vagina, prostate, testis, penis), urinary system (e.g., urinary bladder, kidney, ureter, and other urinary organs), eye, brain, endocrine system (e.g., thyroid and other endocrine), lymphoma (e.g., hodgkin's disease, non-hodgkin's lymphoma), multiple myeloma, leukemia (e.g., acute lymphocytic leukemia, chronic lymphocytic leukemia, acute myeloid leukemia, chronic myeloid leukemia).

Examples of viral antigenic and immunogenic polypeptides include, but are not limited to, adenovirus polypeptides, alphavirus polypeptides, calicivirus polypeptides, e.g., a calicivirus capsid antigen, coronavirus polypeptides, distemper virus polypeptides, Ebola virus polypeptides, enterovirus polypeptides, flavivirus polypeptides, hepatitis virus (AE) polypeptides, e.g., a hepatitis B core or surface antigen, herpesvirus polypeptides, e.g., a herpes simplex virus or varicella zoster virus glycoprotein, immunodeficiency virus polypeptides, e.g., the human immunodeficiency virus envelope or protease, infectious peritonitis virus polypeptides, influenza virus polypeptides, e.g., an influenza A hemagglutinin, neuraminidase, or nucleoprotein, leukemia virus polypeptides, Marburg virus polypeptides, orthomyxovirus polypeptides, papilloma virus polypeptides, parainfluenza virus polypeptides, e.g., the hemagglutinin/neuraminidase, paramyxovirus polypeptides, parvovirus polypeptides, pestivirus polypeptides, picorna virus polypeptides, e.g., a poliovirus capsid polypeptide, pox virus polypeptides, e.g., a vaccinia virus polypeptide, rabies virus polypeptides, e.g., a rabies virus glycoprotein G, reovirus polypeptides, retrovirus polypeptides, and rotavirus polypeptides.

Examples of bacterial antigenic and immunogenic polypeptides include, but are not limited to, *Actinomyces* polypeptides, *Bacillus* polypeptides, e.g., immunogenic polypeptides from *Bacillus anthracis*, *Bacteroides* polypeptides, *Bordetella* polypeptides, *Bartonella* polypeptides, *Borrelia* polypeptides, e.g., *B. burgdorferi* OspA, *Brucella* polypeptides, *Campylobacter* polypeptides, *Capnocytophaga* polypeptides, *Chlamydia* polypeptides, *Clostridium* polypeptides, *Corynebacterium* polypeptides, *Coxiella* polypeptides, *Dermatophilus* polypeptides, *Enterococcus* polypeptides, *Ehrlichia* polypeptides, *Escherichia* polypeptides, *Francisella* polypeptides, *Fusobacterium* polypeptides, *Haemobartonella* polypeptides, *Haemophilus* polypeptides, e.g., *H. influenzae* type b outer membrane protein, *Helicobacter* polypeptides, *Klebsiella* polypeptides, L form bacteria polypeptides, *Leptospira* polypeptides, *Listeria* polypeptides, *Mycobacteria* polypeptides, *Mycoplasma* polypeptides, *Neisseria* polypeptides, *Neorickettsia* polypeptides, *Nocardia* polypeptides, *Pasteurella* polypeptides, *Peptococcus* polypeptides, *Peptostreptococcus* polypeptides, *Pneumococcus* polypeptides, *Proteus* polypeptides, *Pseudomonas* polypeptides, *Rickettsia* polypeptides, *Rochalimaea* polypeptides, *Salmonella* polypeptides, *Shigella* polypeptides, *Staphylococcus* polypeptides, *Streptococcus* polypeptides, e.g., *S. pyogenes* M proteins, *Treponema* polypeptides, and *Yersinia* polypeptides, e.g., *Y. pestis* F1 and V antigens.

Examples of parasitic antigenic and immunogenic polypeptides include, but are not limited to *Balantidium coli* polypeptides, *Entamoeba histolytica* polypeptides, *Fasciola hepatica* polypeptides, *Giardia lamblia* polypeptides, *Leishmania* polypeptides, and *Plasmodium* polypeptides (e.g., *Plasmodium falciparum* polypeptides).

Examples of fungal antigenic and immunogenic polypeptides include, but are not limited to, *Aspergillus* polypeptides, *Candida* polypeptides, *Coccidiodes immitis* or *C. posadasii* polypeptides, *Cryptococcus* polypeptides, *Histoplasma* polypeptides, *Pneumocystis* polypeptides, and *Paracoccidiodes* polypeptides.

Examples of tumor-associated antigenic and immunogenic polypeptides include, but are not limited to, tumor-specific immunoglobulin variable regions, GM2, Tn, sTn, Thompson-Friedenreich antigen (TF), Globo H, Le(y), MUC1, MUC2, MUC3, MUC4, MUC5AC, MUC5B, MUC7, carcinoembryonic antigens, beta chain of human chorionic gonadotropin (hCG beta), C35, HER2/neu, CD20, PSMA, EGFRvIII, KSA, PSA, PSCA, GP100, MAGE 1, MAGE 2, TRP 1, TRP 2, tyrosinase, MART-1, PAP, CEA, BAGE, MAGE, RAGE, and related proteins.

Compositions of the invention can further comprise other therapeutic agents. Examples of therapeutic agents include, but are not limited to, antimetabolites, alkylating agents, anthracyclines, antibiotics, and anti-mitotic agents. Antimetabolites include methotrexate, 6-mercaptopurine, 6-thioguanine, cytarabine, 5-fluorouracil decarbazine. Alkylating agents include mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin. Anthracyclines include daunorubicin (formerly daunomycin) and doxorubicin (also referred to herein as adriamycin). Additional examples include mitozantrone and bisantrene. Antibiotics include dactinomycin (formerly actinomycin), bleomycin, mithramycin, and anthramycin (AMC). Antimitotic agents include vincristine and vinblastine (which are commonly referred to as vinca alkaloids). Other cytotoxic agents include procarbazine, hydroxyurea, asparaginase, corticosteroids, mytotane (O,P'-(DDD)), interferons. Further examples of cytotoxic agents include, but are not limited to, ricin, doxorubicin, taxol, cytochalasin B, gramicidin D, ethidium bromide, etoposide, tenoposide, colchicin, dihydroxy anthracin dione, 1-dehydrotestosterone, and glucocorticoid. Analogs and homologs of such therapeutic agents are encompassed by the present invention.

Bacterial Cell

The modified bacterium of the invention can be derived from a native form of the bacterial cell or can be a recombinant bacterial cell. In one embodiment, any bacterial cell described herein can also be unmodified and formulated with a separate ceramide-like glycolipid antigen. In another embodiment, a ceramide-like glycolipid of the invention is physically associated with a bacterial cell, e.g., incorporated into a bacterial cell wall, and used as an adjuvant to enhance an immune response, e.g., to a bacteria.

Bacteria can be described as Gram-positive or Gram-negative. Beveridge T J, *Biotech Histochein* 76(3): 111-118 (2001); Gram H C, *Fortschritte der Medizin* 2: 185-189 (1884). Gram-positive bacteria are those that are stained dark blue or violet by Gram staining. Gram-positive bacteria are generally characterized by having as part of their cell wall structure peptidoglycan as well as polysaccharides and/or teichoic acids. The peptidoglycans, which are sometimes also called murein, are heteropolymers of glycan strands, which are cross-linked through short peptides. Gram-negative bacteria are generally surrounded by two membranes. The outer membrane contains lipopolysaccharides (LPS) and porins, and functions as a permeability barrier. *Mycobacteria* produce a thick mycolate-rich outer covering, which functions as an efficient barrier. *Mycobacteria* stain acid-fast and are phylogenetically related to the Gram-positive bacteria.

Bacterial or fungal agents that can cause disease or symptoms and that can be treated, prevented, and/or diagnosed by a modified bacterium, or composition, or vaccine composition of the present invention can include, but are not limited to the following Gram-negative and Gram-positive bacteria and bacterial families and fungi: *Acinetobacter*, Actinomycetes (e.g., *Corynebacterium, Mycobacterium, Norcardia*), *Cryptococcus neoformans, Aspergillus*, Bacillaceae (e.g., *Bacillus, anthracis*), Bacteroidaceae, *Blastomyces, Bordetella, Brucella, Candidia, Campylobacter, Clostridium, Coccidioides, Corynebacterium, Cryptococcus, Dermatophytes*, Enterobacteriaceae (*E. coli* (e.g., Enterotoxigenic *E. coli* and Enterohemorrhagic *E. coli*) *Klebsiella, Salmonella* (e.g., *Salmonella typhi*, and *Salmonella paratyphi*), *Serratia, Shigella, Yersinia*, etc.), *Erysipelothrix, Francisella, Helicobacter*, Legionellaceae, Spirochaetaceae (e.g., *Borrelia* (e.g., *Borrelia burgdorferi*)), Leptospiraceae, *Listeria, Mycoplasmatales, Mycobacterium leprae*, Vibrionaceae (e.g., *Vibrio cholerae*), Neisseriaceae (e.g., *Neisseria meningitidis, Neisseria gonorrhoeae*), *Actinobacillus, Haemophilus* (e.g., *Haemophilus influenza* type B), *Pasteurella, Pseudomonas*, Rickettsiaceae, Chlamydiaceae, *Treponema pallidum*, Staphylococcaceae (e.g., *Staphylococcus aureus*, and Streptococcaceae (e.g., *Streptococcus pneumoniae* and Group B *Streptococcus*).

These bacterial or fungal families can cause the following diseases or symptoms, including, but not limited to: bacteremia, endocarditis, eye infections (conjunctivitis, tuberculosis, uveitis), gingivitis, opportunistic infections (e.g., AIDS related infections), paronychia, prosthesis-related infections, Reiter's Disease, respiratory tract infections, such as Whooping Cough or Empyema, sepsis, Lyme Disease, Cat-Scratch Disease, Dysentery, Paratyphoid Fever, food poisoning, Typhoid, pneumonia, Gonorrhea, meningitis (e.g., mengitis types A and B), Chlamydia, Syphilis, Diphtheria, Leprosy, Paratuberculosis, Tuberculosis (TB), Hansen's disease, Pulmonary disease resembling tuberculosis, Lymphadenitis, Skin disease, or Disseminated disease, Lupus, Botulism, gangrene, tetanus, impetigo, Rheumatic Fever, Scarlet Fever, sexually transmitted diseases, skin diseases (e.g., cellulitis, dermatocycoses), toxemia, urinary tract infections, and wound infections.

A modified bacterium, composition, or vaccine composition of the invention can be used to treat, prevent, and/or diagnose any of these symptoms or diseases. In specific embodiments, compositions of the invention are used to treat: tuberculosis, pulmonary disease resembling tuberculosis, lymphadenitis, skin disease, disseminated disease, bubonic plague, pneumonic plague, tularemia, Legionairre's disease, anthrax, typhoid fever, paratyphoid fever, foodborne illness, listeriosis, malaria, HIV, SIV, HPV, influenza, hepatitis (HAV, HBV, and HCV), and cancer.

Mycobacteria

The genus *Mycobacterium* includes pathogens known to cause serious diseases in mammals, including, for example, tuberculosis and leprosy. *Mycobacterium* (also referred to as mycobacteria) do not contain endospores or capsules, and are usually considered Gram-positive. In addition to the usual fatty acids found in membrane lipids, mycobacteria have a wide variety of very long-chain saturated ($C_{18}$-$C_{32}$) and monounsaturated (up to $C_{26}$) n-fatty acids. The occurrence of α-alkyl β-hydroxy very long-chain fatty acids, i.e., mycolic acids, is a hallmark of mycobacteria and related species. Mycobacterial mycolic acids are large ($C_{70}$-$C_{90}$) with a large α-branch ($C_{20}$-$C_{25}$). The main chain contains one or two double bonds, cyclopropane rings, epoxy groups, methoxy groups, keto groups or methyl branches. Such acids are major components of the cell wall, occurring mostly esterified in clusters of four on the terminal hexa-arabinofuranosyl units of the major cell-wall polysaccharides called arabinogalactans. They are also found esterified to the 6 and 6' positions of trehalose to form 'cord factor'. Small amounts of mycolate are also found esterified to glycerol or sugars such as trehalose, glucose and fructose depending on the sugars present in the culture medium. *Mycobacteria* also contain a wide variety of methyl-branched fatty acids. These include 10-methyl $C_{18}$ fatty acid (tuberculostearic acid found esterified in phosphatidyl inositide mannosides), 2,4-dimethyl $C_{14}$ acid and mono-, di- and trimethyl-branched $C_{14}$ to $C_{25}$ fatty acids found in trehalose-containing lipooligosaccharides, trimethyl unsaturated $C_{27}$ acid (phthienoic acid), tetra-methyl-branched $C_{28}$-$C_{32}$ faccy acids (mycocerosic acids) and shorter homologues found in phenolic glycolipids and phthiocerol esters, and multiple methyl-branched phthio-ceranic acids such as hepamethyl-branched $C_{37}$ acid and oxygenated multiple methyl-branched acids such as 17-hydroxy-2,4,6,8,10,12,14,16-octamethyl $C_{40}$ acid found in sulpholipids. In addition, mycocerosic acids and other branched acids are esterified to phthicerol and phenolphthicerol and their derivates. Kolattukudy et al., *Mol. Microbio.* 24(2):263-270 (1997). Evidence implicates specific cell envelope lipids in Mtb pathogenesis. Rao, et al., *J. Exp. Med.*, 201(4):535-543 (2005).

*Mycobacterium* species include, but are not limited to: *M. abscessus; M. africanum; M. agri; M. aichiense; M. alvei; M. arupense; M. asiaticum; M. aubagnense; M. aurum; M austroafricanum; Mycobacterium avium* complex (MAC); *M. avium; M. avium* paratuberculosis, which has been implicated in Crohn's disease in humans and johne's disease in sheep; *M. avium silvaticum; M. avium "hominissuis"; M. colombiense; M. boeitickei; M. bohemicum; M. bolletii; M. botniense; M. bovis; M. branderi; M. brisbanense; M. brumae; M. canariasense; M. caprae; M. celatum; M. chelonae; M. chimaera; M. chitae; M. chlorophenolicum; M. chubuense; M. conceptionense; M. confluentis; M. conspicuum; M. cookii; M. cosmeticum; M. diernhoferi; M. doricum; M. duvalii; M. elephantis; M. fallax; M. farcinogenes; M. flavescens; M. florentinum; M. fluoroanthenivorans; M. fortuitum; M. fortuitum* subsp. *acetamidolyticum; M. frederiksbergense; M. gadium; M. gastri; M. genavense; M. gilvum; M. goodii; M. gordonae; M. haemophilum; M. hassiacum; M. heckeshornense; M. heidelbergense; M. hiberniae; M. hodleri; M. holsaticum; M. houstonense; M. immunogenum; M. interjectum; M. intermedium; M. intracellulare; M. kansasii; M. komossense; M. kubicae; M. kumamotonense; M. lacus; M. lentiflavum; M. leprae*, which causes leprosy; *M. lepraemurium; M. madagascariense; M. mageritense; M.*

*malmoense; M. marinum; M. massiliense; M. microti; M. monacense; M. montefiorense; M. moriokaense; M. mucogenicum; M. murale; M. nebraskense; M. neoaurum; M. neworleansense; M. nonchromogenicum; M. novocastrense; M. ohuense; M. palustre; M. parafortuitum; M. parascrofulaceum; M. parmense; M. peregrinum; M. phlei; M phocaicum; M. pinnipedii; M. porcinum; M. poriferae; M. pseudoshottsii; M. pulveris; M. psychrotolerans; M. pyrenivorans; M. rhodesiae; M. saskatchewanense; M. scrofidaceum; M. senegalense; M. seoulense; M. septicum; M. shimoidei; M. shottsii; M. simiae; M. smegmatis; M. sphagni; M. szulgai; M. terrae; M. thermoresistibile; M. tokaiense; M. triplex; M. triviale; Mycobacterium tuberculosis* complex (MTBC), members are causative agents of human and animal tuberculosis (*M. tuberculosis*, the major cause of human tuberculosis; *M. bovis; M. bovis* BCG; *M. africanum; M. canetti; M. caprae; M. pinnipedii*); *M. tusciae; M. ulcerans*, which causes the "Buruli", or "Bairnsdale, ulcer"; *M. vaccae; M. vanbaalenii; M. wolinskyi;* and *M. xenopi*.

Mycobacteria can be classified into several groups for purpose of diagnosis and treatment, for example: *M. tuberculosis* complex (MTB) which can cause tuberculosis: *M. tuberculosis, M. africanum, M. bovis, M. bovis* BCG, *M. caprae, M. microti, M. pinnipedii,* the dassie *bacillus,* and *M. canettii* (proposed name) (Somoskovi, et al., *J. Clinical Microbio* 45(2):595-599 (2007)); *M. leprae* which causes Hansen's disease or leprosy; nontuberculous mycobacteria (NTM) are all the other mycobacteria which can cause pulmonary disease resembling tuberculosis, lymphadenitis, skin disease, or disseminated disease. MTB members show a high degree of genetic homogeneity. Somoskovi (2007). The mycobacteria of the invention can include recombinant mycobacteria. For example, recombinant mycobacterial cells, e.g., recombinant BCG cells, e.g., rBCG30 cells.

Recombinant Bacteria

A modified bacterium of the invention can also include a recombinant bacterial cell, e.g., a recombinant mycobacterial cell. A non-limiting example of a recombinant bacterial cell is rBCG30, which is derived from a vaccine strain of BCG and has been genetically modified to overexpress the immunodominant antigen Ag85B. See Doherty and Anderson, *Clinical Microbio Reviews* 18(4): 687-702 (2005). Other examples of recombinant bacterial cells suitable for producing glycolipid modified bacterium of the invention include, but are not limited to BCG-HIV; BCG-SIV; BCG-HCV; rBCG/IL-2, and recombinant *M. smegmatis* expressing HIV peptides (See e.g., Aldovini and Young, *Nature* 351: 479-482 (1994); Yasutomi et al., *J. of Immunol.* 150(7):3101-3107 (1993); Uno-Furuta et al., *Vaccine* 21(23): 3149-3156 (2003); Matsumoto et al., *J. Exp. Med.* 188(5): 845-854 (1998); Yamada et al., *J. of Urology* 164(2): 526-531 (2000); Cayabyab et al., *J. of Virology* 80(4): 1645-1652 (2006); Stover et al., *Nature* 351: 456-460 (1991); and Bloom et al., U.S. Pat. No. 5,504,005).

In one embodiment, the modified bacterium comprises a recombinant bacterial cell engineered to express a polypeptide encoded by non-native polynucleotides, e.g., BCG-HIV, wherein the recombinant bacterial cell is physically associated with a ceramide-like glycolipid. The invention further relates to a composition or vaccine composition comprising a modified bacterium of the invention, wherein the bacterial cell is native or recombinant.

The invention further relates to a recombinant (genetically engineered) modified bacterium, e.g., a ceramide-like glycolipid/mycobacterial complex, which expresses DNA encoding a heterologous polypeptide. The DNA can be incorporated into the bacterial genome or exist extrachromosomally using standard genetic engineering techniques. Recombinant bacteria of the invention can be engineered using vectors for the introduction of DNA of interest, e.g., DNA encoding heterologous antigens or immunogens, into bacteria, e.g., mycobacteria.

As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Certain vectors are capable of autonomous replication in a host cell into which they are introduced (e.g., bacterial vectors having a bacterial origin of replication). The vectors of the present invention are capable of directing the expression of genes encoding polypeptides, e.g., immunogenic polypeptides, to which they are operatively linked. Such vectors are referred to herein as "expression vectors". In general, expression vectors of utility in recombinant DNA techniques are often in the form of plasmids.

Expression vectors comprising nucleic acids encoding polypeptides can be useful in the present invention, e.g., for expression of immunogenic polypeptides, from recombinant bacteria, e.g., glycolipid modified recombinant mycobacteria. The choice of vector and expression control sequences to which such nucleic acids are operably linked depends on the functional properties desired, e.g., protein expression, and the host cell to be transformed.

Expression control elements useful for regulating the expression of an operably linked coding sequence are known in the art. Examples include, but are not limited to, inducible promoters, constitutive promoters, secretion signals, and other regulatory elements. When an inducible promoter is used, it can be controlled, e.g., by a change in nutrient status of host cell medium or a change in temperature. Polynucleotide and nucleic acid coding regions of the present invention can be associated with additional coding regions which encode secretory or signal peptides, which direct the secretion of a polypeptide encoded by a polynucleotide of the present invention.

In one embodiment, bacterial expression of a polynucleotide of interest occurs extrachromosomally, e.g., from a plasmid (e.g., episomally). For example, a gene of Interest is cloned into a plasmid and introduced into a cultured mycobacterial cell, e.g., BCG or *M. smegmatis*, where the gene of interest encodes a polypeptide of interest, e.g., an immunogenic polypeptide. Plasmid vectors containing replicon and control sequences which are derived from species compatible with the host cell, e.g., mycobacterial host cells, are used. The vector can carry a replication site, as well as marking sequences which are capable of providing phenotypic selection in transformed cells.

A vector of the invention can include, but is not limited to a prokaryotic replicon, i.e., a DNA sequence having the ability to direct autonomous replication and maintenance of the recombinant DNA molecule extra-chromosomally in a bacterial host cell. Such replicons are well known in the art. In addition, vectors that include a prokaryotic replicon may also include a gene whose expression confers a detectable marker such as a drug resistance. Non-limiting examples of bacterial drug-resistance genes are those that confer resistance to ampicillin or tetracycline.

Vectors that include a prokaryotic replicon can also include a prokaryotic or bacteriophage promoter for directing expression of the coding gene sequences in a bacterial host cell. Promoter sequences compatible with bacterial hosts typically are provided in plasmid vectors containing convenient restriction sites for insertion of a DNA segment to be expressed. Examples of promoters which can be used for expression in prokaryotic host cells, e.g., mycobacterial host cells, include, but are not limited to heat shock promoters, stress protein promoters, pMTB30 promoters, B-lactamase (penicillinase) promoters, lactose promoters, promoters expressing kanamycin resistance, promoters expressing chloramphenicol resistance, and cI promoters (see also Sambrook et al.). Various prokaryotic cloning vectors can be used in the invention. Examples of such plasmid vectors include, but are not limited to pUC8, pUC9, pBR322 and pBR329 (BioRad® Laboratories), pPL, pEMBL and pKK223 (Pharmacia) (see also Sambrook et al.).

Vector DNA can be introduced into prokaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al. (MOLECULAR CLONING: A LABORATORY MANUAL. 2nd ed., Cold Spring Harbor Laboratory, Cold Spring Harbor Laboratory Press, Cold Spring Harbor, N.Y., 1989), and other laboratory manuals. Transformation of host cells, e.g., bacterial cells such as mycobacterial cells or glycolipid modified mycobacterial cells, can be accomplished by conventional methods suited to the vector and host cell employed. For transformation of prokaryotic host cells, e.g., mycobacterial cells, electroporation and salt treatment methods can be employed (Cohen et al., *Proc. Natl. Acad. Sci. USA* 69:2110-14 (1972)), as well as other techniques known in the art.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" can be used instead of or interchangeably with any of these terms. The term "polypeptide" is also intended to refer to the products of post-expression modifications of the polypeptide. A polypeptide can be derived from a natural biological source or produced by recombinant technology, but is not necessarily translated from a designated nucleic acid sequence. It can be generated in any manner, including by chemical synthesis.

A polypeptide of the invention can be of a size of about 3 or more, 5 or more, 10 or more, 20 or more, 25 or more, 50 or more, 75 or more, 100 or more, 200 or more, 500 or more, 1,000 or more, or 2,000 or more amino acids.

By an "isolated polypeptide" or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells or as a component of a recombinant bacterial vaccine are considered isolated for purposed of the invention, as are native or recombinant polypeptides which have been separated, fractionated, or partially or substantially purified by any suitable technique.

Also included as polypeptides of the present invention are fragments, derivatives, analogs, or variants of the foregoing polypeptides, and any combination thereof. The terms "fragment," "variant," "derivative" and "analog" when referring to polypeptides of the present invention include any polypeptides that retain at least some of the biological, antigenic, or immunogenic properties of the corresponding native polypeptide.

The term "polynucleotide" is intended to encompass a singular nucleic acid as well as plural nucleic acids, and refers to an isolated nucleic acid molecule or construct, e.g., messenger RNA (mRNA), virally-derived RNA, or plasmid DNA (pDNA). A polynucleotide can comprise a conventional phosphodiester bond or a non-conventional bond (e.g., an amide bond, such as found in peptide nucleic acids (PNA)). The term "nucleic acid" refers to any one or more nucleic acid segments, e.g., DNA or RNA fragments, present in a polynucleotide. RNA of the present invention can be single stranded or double stranded.

By "isolated" nucleic acid or polynucleotide is intended a nucleic acid molecule, DNA or RNA, which has been removed from its native environment. For example, a recombinant polynucleotide encoding a therapeutic polypeptide contained in a vector is considered isolated for the purposes of the present invention. Further examples of an isolated polynucleotide include recombinant polynucleotides maintained in heterologous host cells, e.g., recombinant bacterial cells, or purified (partially or substantially) polynucleotides in solution. Isolated RNA molecules include in vivo or in vitro RNA transcripts of the present invention, as well as positive and negative strand forms, and double-stranded forms, of pestivirus vectors disclosed herein. Isolated polynucleotides or nucleic acids according to the present invention further include such molecules produced synthetically. In addition, a polynucleotide or a nucleic acid can be or can include a regulatory element such as a promoter, ribosome binding site, or a transcription terminator.

As used herein, a "heterologous polynucleotide" or a "heterologous nucleic acid" or a "heterologous gene" or a "heterologous sequence" or an "exogenous DNA segment" refers to a polynucleotide, nucleic acid or DNA segment that originates from a source foreign to the particular host cell, or, if from the same source, is modified from its original form. A heterologous gene in a host cell includes a gene that is endogenous to the particular host cell, but has been modified. Thus, the terms refer to a DNA segment which is foreign or heterologous to the cell, or homologous to the cell but in a position within the host cell nucleic acid in which the element is not ordinarily found.

As used herein, a "coding region" is a portion of nucleic acid which consists of codons translated into amino acids. Although a "stop codon" (TAG, TGA, or TAA) is not translated into an amino acid, it can be considered to be part of a coding region, if present, but any flanking sequences, for example promoters, ribosome binding sites, transcriptional terminators, introns, 5' and 3' non-translated regions, and the like, are not part of a coding region. Two or more coding regions of the present invention can be present in a single polynucleotide construct, e.g., on a single vector, or in separate polynucleotide constructs, e.g., on separate (different) vectors. Furthermore, any vector can contain a single coding region, or can comprise two or more coding regions. In addition, a vector, polynucleotide, or nucleic acid of the invention can encode two or more heterologous coding regions, either fused or unfused. Heterologous coding regions include without limitation specialized elements or motifs, such as a secretory signal peptide or a heterologous functional domain.

In certain embodiments, the polynucleotide or nucleic acid is DNA. In the case of DNA, a polynucleotide comprising a nucleic acid, which encodes a polypeptide normally can include a promoter and/or other transcription or translation control elements operably associated with one or more coding regions. An operable association is when a coding region for a gene product, e.g., a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter can be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription.

By "a reference amino acid sequence" is meant the specified sequence without the introduction of any amino acid substitutions. As one of ordinary skill in the art would understand, if there are no substitutions, the "isolated polypeptide" of the invention comprises an amino acid sequence which is identical to the reference amino acid sequence.

Polypeptides described herein can have various alterations such as substitutions, insertions or deletions. Exemplary amino acids that can be substituted in the polypeptide include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Corresponding fragments of polypeptides at least 70%, 75%, 80%, 85%, 90%, or 95% identical to the polypeptides and reference polypeptides described herein are also contemplated.

As known in the art, "sequence identity" between two polypeptides is determined by comparing the amino acid sequence of one polypeptide to the sequence of a second polypeptide. When discussed herein, whether any particular polypeptide is at least about 70%, 75%, 80%, 85%, 90% or 95% identical to another polypeptide can be determined using methods and computer programs/software known in the art such as, but not limited to, the BESTFIT program (Wisconsin Sequence Analysis Package, Version 8 for Unix, Genetics Computer Group, University Research Park, 575 Science Drive, Madison, Wis. 53711). BESTFIT uses the local homology algorithm of Smith and Waterman, Advances in Applied Mathematics 2:482-489 (1981), to find the best segment of homology between two sequences. When using BESTFIT or any other sequence alignment program to determine whether a particular sequence is, for example, 95% identical to a reference sequence according to the present invention, the parameters are set, of course, such that the percentage of identity is calculated over the full length of the reference polypeptide sequence and that gaps in homology of up to 5% of the total number of amino acids in the reference sequence are allowed.

Ceramide-Like Glycolipid Antigens

Ceramide-like glycolipid antigens useful within the present invention include without limitation those ceramide-like glycolipids which are capable of modulating an immune response in an animal when presented with a bacterial cell, e.g., by incorporation of the ceramide-like glycolipid into the cell wall of a bacterial cell. The antigens may be derived from foreign antigens or from autoantigens. Further, the ceramide-like glycolipid antigens can be synthetic. Suitable antigens are disclosed, e.g., in Porcelli, U.S. Patent Appl. Publ. No. 2006/0052316, Tsuji, U.S. Patent Appl. Publ. No. 2006/0211856, Jiang, U.S. Patent Appl. Publ. No. 2006/0116331, Hirokazu et al., U.S. Patent Appl. Publ. No. 2006/0074235, Tsuji et al., U.S. Patent Appl. Publ. No. 2005/0192248, Tsuji, U.S. Patent Application No. 2004/0127429, and Tsuji et al., U.S. Patent Application No. 2003/0157135, which are incorporated herein by reference. In certain embodiments, the ceramide-like glycolipid is α-GalCer or an analog thereof. In other embodiments, the ceramide-like glycolipid is a α-C-GalCer or an analog thereof.

The term "optionally substituted" as used herein means either unsubstituted or substituted with one or more substituents including halogen (F, Cl, Br, I), alkyl, substituted alkyl, aryl, substituted aryl, or alkoxy.

The term "alkyl", as used herein by itself or part of another group refers to a straight-chain or branched saturated aliphatic hydrocarbon typically having from one to eighteen carbons or the number of carbons designated. In one such embodiment, the alkyl is methyl. Non-limiting exemplary alkyl groups include ethyl, n-propyl, isopropyl, and the like.

The term "substituted alkyl" as used herein refers to an alkyl as defined above having one or more halogen (F, Cl, Br, I) substitutes.

The term "heterocycle" as used herein means a 3- to 10-membered monocyclic or bicyclic heterocyclic ring which is either saturated, unsaturated non-aromatic, or aromatic containing up to 4 heteroatoms. Each heteroatom is independently selected from nitrogen, which can be quaternized; oxygen; and sulfur, including sulfoxide and sulfone. The heterocycle can be attached via a nitrogen, sulfur, or carbon atom. Representative heterocycles include pyridyl, furyl, thiophenyl, pyrrolyl, oxazolyl, imidazolyl, thiazolyl, thiadiazolyl, isoxazolyl, pyrazolyl, isothiazolyl, pyridazinyl, pyrimidinyl, pyrazinyl, triazinyl, morpholinyl, pyrrolidinonyl, pyrrolidinyl, piperidinyl, piperazinyl, hydantoinyl, valerolactamyl, oxiranyl, oxetanyl, tetrahydrofuranyl, tetrahydropyranyl, tetrahydropyrindinyl, tetrahydropyrimidinyl, tetrahydrothiophenyl, tetrahydrothiopyranyl, quinolinyl, -isoquinolinyl, -chromonyl, -coumarinyl, -indolyl, -indolizinyl, -benzo[b]furanyl, -benzo[b]thiophenyl, -indazolyl, -purinyl, -4H-quinolizinyl, -isoquinolyl, -quinolyl, -phthalazinyl, -naphthyridinyl, -carbazolyl, and the like. The term heterocycle also includes heteroaryls.

The term "aryl" as used herein by itself or part of another group refers to monocyclic and bicyclic aromatic ring systems typically having from six to fourteen carbon atoms (i.e., $C_6$-$C_{14}$ aryl) such as phenyl, 1-naphthyl, and the like.

The term "substituted aryl" as used herein refers to an aryl as defined above having one or more substitutes including halogen (F, Cl, Br, I) or alkoxy.

The term "aralkyl" as used herein by itself or part of another group refers to an alkyl as defined above having one or more aryl substituents. Non-limiting exemplary aralkyl groups include benzyl, phenylethyl, diphenylmethyl, and the like.

The term "alkoxy" as used herein by itself or part of another group refers to an alkyl attached to a terminal oxygen atom. Non-limiting exemplary alkoxy groups include methoxy, ethoxy and the like.

The term "alkane" as used herein means a straight chain or branched non-cyclic saturated hydrocarbon. Representative straight chain alkane include -methyl, -ethyl, -n-propyl, -n-butyl, -n-pentyl, -n-hexyl, -n-heptyl, -n-octyl, -n-nonyl and -n-decyl. Representative branched alkane include -isopropyl, -sec-butyl, -isobutyl, -tert-butyl, -isopentyl, -neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-methylhexyl, 2-methylhexyl, 3-methylhexyl, 4-methylhexyl, 5-methylhexyl, 1,2-dimethylpentyl, 1,3-dimethylpentyl, 1,2-dimethylhexyl, 1,3-dimethylhexyl, 3,3-dimethylhexyl, 1,2-dimethylheptyl, 1,3-dimethylheptyl, and 3,3-dimethylheptyl.

The term "alkene" as used herein means a straight chain or branched non-cyclic hydrocarbon having at least one carbon-carbon double bond. Representative straight chain and branched alkene include -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, -1-hexenyl, -2-hexenyl, -3-hexenyl, -1-heptenyl, -2-heptenyl, -3-heptenyl, -1-octenyl, -2-octenyl, -3-octenyl, -1-nonenyl, -2-nonenyl, -3-nonenyl, -1-decenyl, -2-decenyl, -3-decenyl and the like.

The term "cylcoalkane" as used herein means a saturated cyclic hydrocarbon having from 3 to 15 carbon atoms. Representative cycloalkanes are cyclopropyl, cyclopentyl and the like.

The term "alkylcycloalkene" as used herein by itself or part of another group refers to an alkyl as defined above attached a cylcoalkane as defined above.

The term "cylcoalkene" as used herein means means a mono-cyclic non-aromatic hydrocarbon having at least one carbon-carbon double bond in the cyclic system and from 5 to 15 carbon atoms. Representative cycloalkenes include -cyclopentenyl, -cyclopentadienyl, -cyclohexenyl, -cyclohexadienyl, -cycloheptenyl, -cycloheptadienyl, -cycloheptatrienyl, -cyclooctenyl, -cyclooctadienyl, cyclooctatrienyl, -cyclooctatetraenyl, -cyclononenyl -cyclononadienyl, -cyclodecenyl, -cyclodecadienyl and the like. The term "cycloalkene" also include bicycloalkenes and tricycloalkenes. The term "bicycloalkene" as used herein means a bicyclic hydrocarbon ring system having at least one carbon-carbon double bond in one of the rings and from 8 to 15 carbon atoms. Representative bicycloalkenes include, but are not limited to, -indenyl, -pentalenyl, -naphthalenyl, -azulenyl, -heptalenyl, -1,2,7,8-tetrahydronaphthalenyl, and the like. The term "tricycloalkene" as used herein, means a tri-cyclic hydrocarbon ring system having at least one carbon-carbon double bond in one of the rings and from 8 to 15 carbon atoms. Representative tricycloalkenes include, but are not limited to, -anthracenyl, -phenanthrenyl, -phenalenyl, and the like.

The term "aromatic ring" as used herein means a 5 to 14 membered aromatic carbocyclic ring, including both mono, bicyclic, and tricyclic ring systems. Representative aromatic rings are phenyl, napthyl, anthryl and phenanthryl.

The phrase "oxo" as used herein, means a double bond to oxygen. i.e., C=O.

The term "monosaccharide" as used herein means any of the simple sugars that serve as building blocks for carbohydrates. Examples of monosaccharides include glucose, fucose, galactose, and mannose.

Other ceramide-like glycolipids for use in the present invention include, but are not limited to the ceramide-like glycolipid antigens in Table 1.

TABLE 1

| Compound | CHO group | Structure |
|---|---|---|
| DB04-1 (KRN7000) | α-D-Gal | 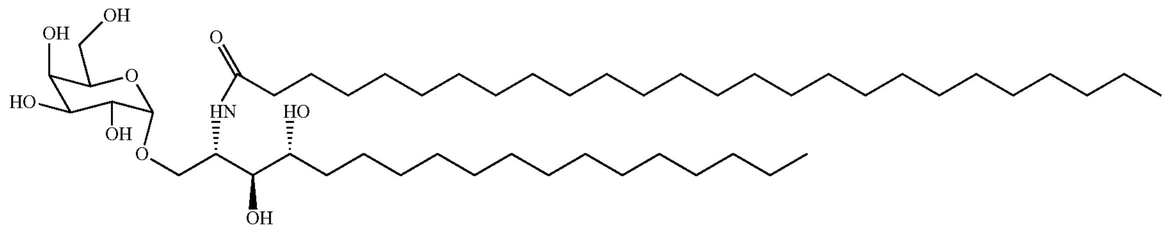 [SMILES: CCCCCCCCCCCCCCCCCCCCCCCCCC(=O)N[C@@H](COC1OC(CO)C(O)C(O)C1O)[C@H](O)[C@H](O)CCCCCCCCCCCCCC] |
| DB01-1 | α-D-Gal | 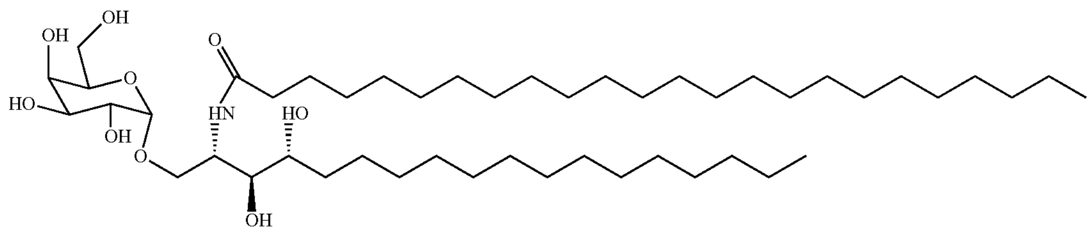 [SMILES: CCCCCCCCCCCCCCCCCCCCCCCC(=O)N[C@@H](COC1OC(CO)C(O)C(O)C1O)[C@H](O)[C@H](O)CCCCCCCCCCCCCC] |
| DB02-1 | α-D-Glu | 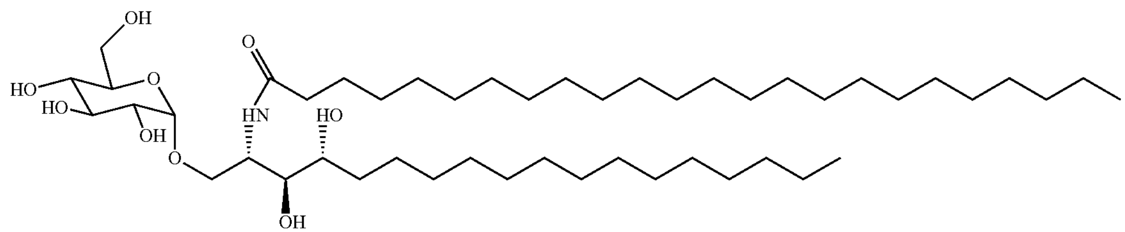 [SMILES: CCCCCCCCCCCCCCCCCCCCCCCC(=O)N[C@@H](COC1OC(CO)C(O)C(O)C1O)[C@H](O)[C@H](O)CCCCCCCCCCCCCC] |
| DB02-2 | α-D-Man | 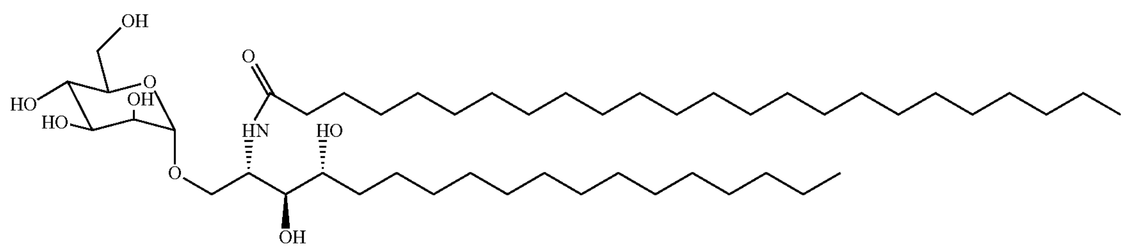 [SMILES: CCCCCCCCCCCCCCCCCCCCCCCC(=O)N[C@@H](COC1OC(CO)C(O)C(O)C1O)[C@H](O)[C@H](O)CCCCCCCCCCCCCC] |

TABLE 1-continued

| Compound | CHO group | Structure |
|---|---|---|
| DB03-2 | α-D-Gal | 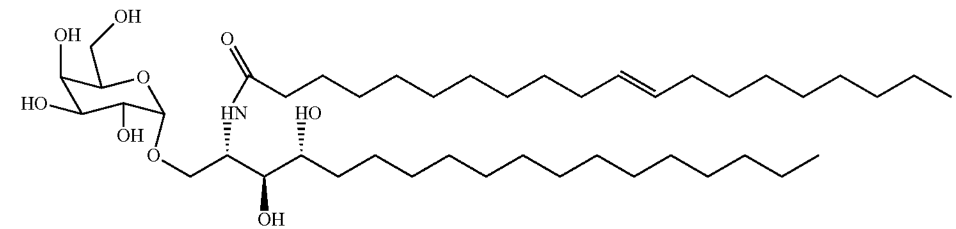 [SMILES: CCCCCCCC/C=C/CCCCCCCCCC(=O)N[C@@H](COC1OC(CO)C(O)C(O)C1O)[C@H](O)[C@H](O)CCCCCCCCCCCCCC] |
| DB03-3 | α-D-Gal | 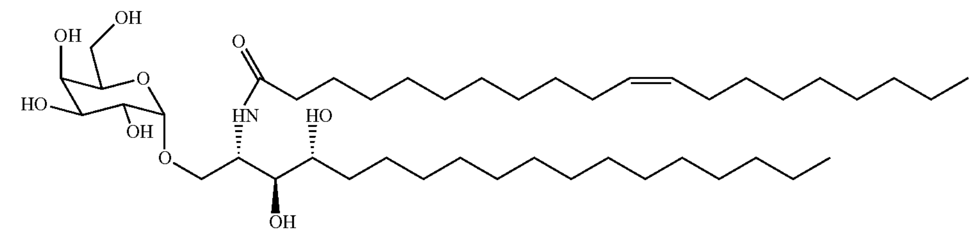 [SMILES: CCCCCCCC/C=C\CCCCCCCCCC(=O)N[C@@H](COC1OC(CO)C(O)C(O)C1O)[C@H](O)[C@H](O)CCCCCCCCCCCCCC] |
| DB03-4 | α-D-Gal | 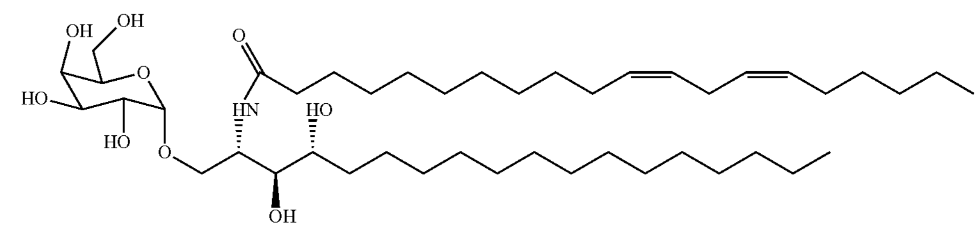 [SMILES: CCCCC/C=C\C/C=C\CCCCCCCCCC(=O)N[C@@H](COC1OC(CO)C(O)C(O)C1O)[C@H](O)[C@H](O)CCCCCCCCCCCCCC] |
| DB03-5 | α-D-Gal | 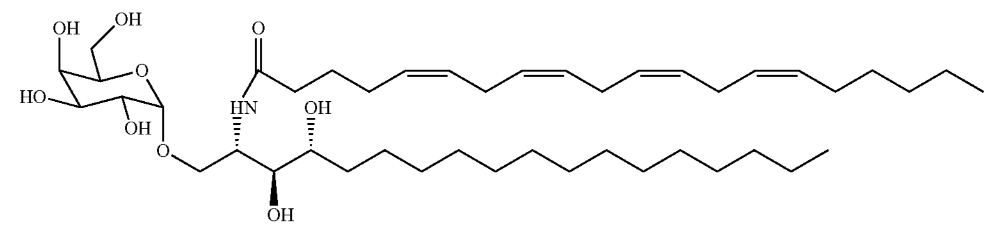 [SMILES: CCCCC/C=C\C/C=C\C/C=C\C/C=C\CCCC(=O)N[C@@H](COC1OC(CO)C(O)C(O)C1O)[C@H](O)[C@H](O)CCCCCCCCCCCCCC] |

TABLE 1-continued

| Compound | CHO group | Structure |
|---|---|---|
| DB03-6 | α-D-Gal | 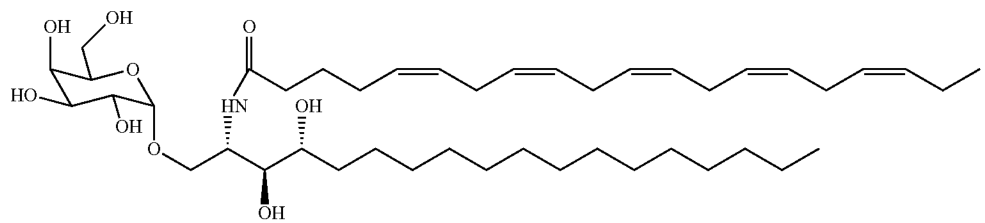 [SMILES: CC/C=C\C/C=C\C/C=C\C/C=C\C/C=C\CCCC(=O)N[C@@H](COC1OC(CO)C(O)C(O)C1O)[C@H](O)[C@H](O)CCCCCCCCCCCCCC] |
| DB04-11 | α-D-Gal | 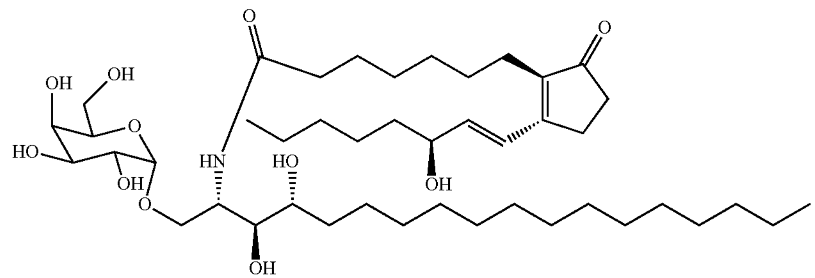 |
| DB06-9 | D-Gal (α1→2)D-Gal | 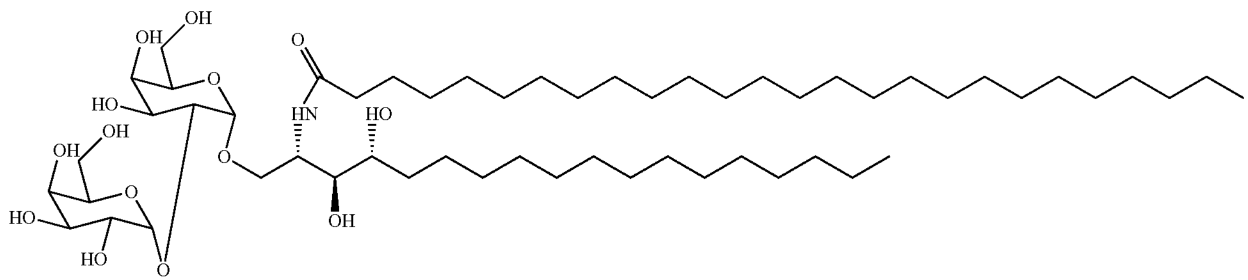 [SMILES: CCCCCCCCCCCCCCCCCCCCCCCCCC(=O)N[C@@H](COC1OC(CO)C(O)C(O)C1OC1OC(CO)C(O)C(O)C1O)[C@H](O)[C@H](O)CCCCCCCCCCCCCC] |
| DB08-1 | α-D-Gal | 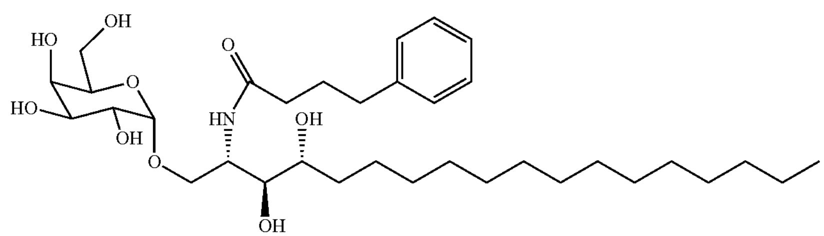 [SMILES: CCCCCCCCCCCCCC[C@@H](O)[C@@H](O)[C@H](COC1OC(CO)C(O)C(O)C1O)NC(=O)CCCc1ccccc1] |

TABLE 1-continued

| Compound | CHO group | Structure |
|---|---|---|
| DB08-2 | α-D-Gal | 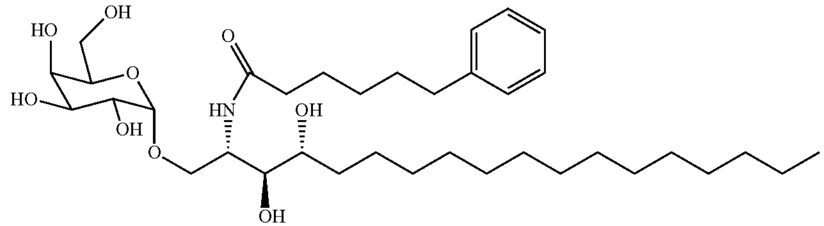 [SMILES: CCCCCCCCCCCCCC[C@@H](O)[C@@H](O)[C@H](COC1OC(CO)C(O)C(O)C1O)NC(=O)CCCCCc1ccccc1] |
| DB08-3 | α-D-Gal | 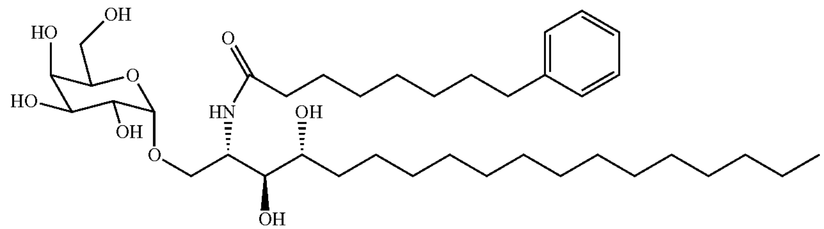 [SMILES: CCCCCCCCCCCCCC[C@@H](O)[C@@H](O)[C@H](COC1OC(CO)C(O)C(O)C1O)NC(=O)CCCCCCCc1ccccc1] |
| DB09-1 | α-D-Gal | 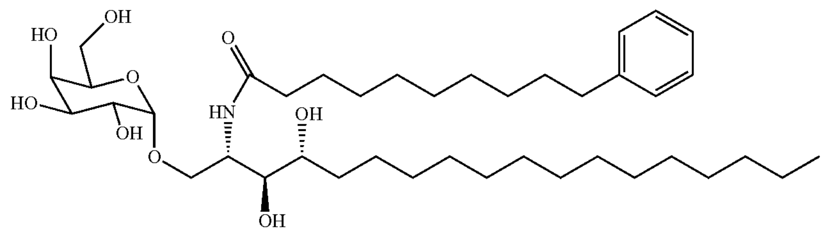 [SMILES: CCCCCCCCCCCCCC[C@@H](O)[C@@H](O)[C@H](COC1OC(CO)C(O)C(O)C1O)NC(=O)CCCCCCCCCc1ccccc1] |
| DB09-2 | α-D-Gal | 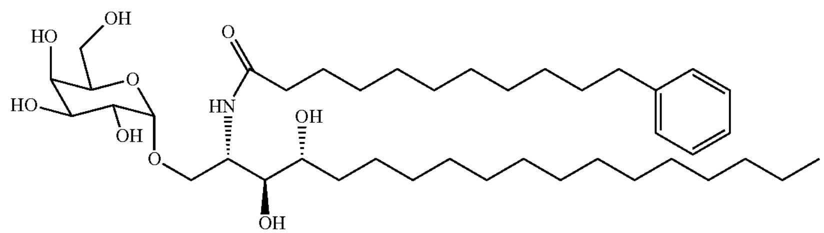 [SMILES: CCCCCCCCCCCCCC[C@@H](O)[C@@H](O)[C@H](COC1OC(CO)C(O)C(O)C1O)NC(=O)CCCCCCCCCCc1ccccc1] |

TABLE 1-continued

| Compound | CHO group | Structure |
|---|---|---|
| AH04-1 (OCH) | α-D-Gal | 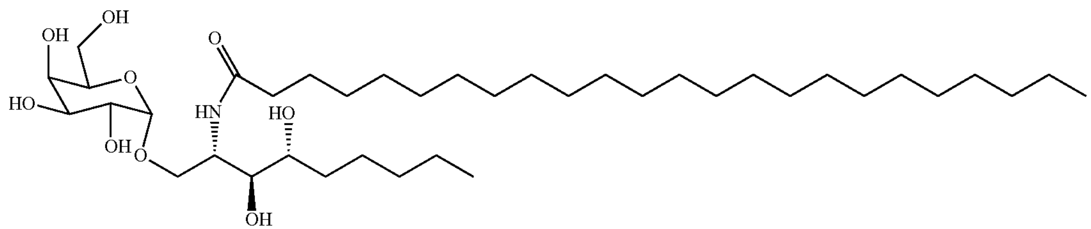 [SMILES: CCCCCCCCCCCCCCCCCCCCCCCC(=O)N[C@@H](COC1OC(CO)C(O)C(O)C1O)[C@H](O)[C@H](O)CCCCC] |
| YTC03-00 | α-D-Gal | 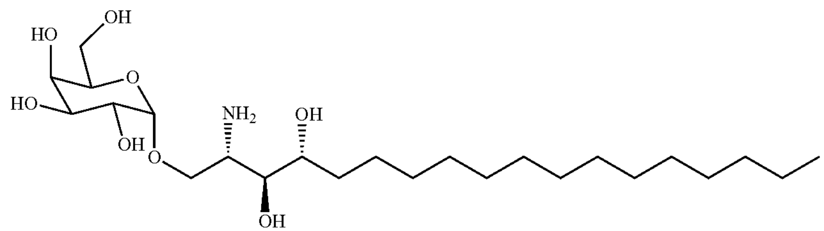 [SMILES: CCCCCCCCCCCCCC[C@@H](O)[C@@H](O)[C@@H](N)COC1OC(CO)C(O)C(O)C1O] |
| YTC03-4 | α-D-Gal | 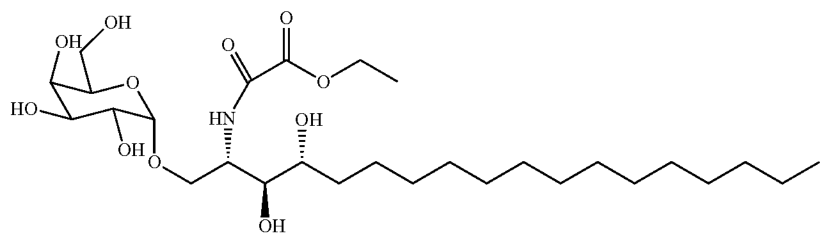 [SMILES: CCCCCCCCCCCCCC[C@@H](O)[C@@H](O)[C@H](COC1OC(CO)C(O)C(O)C1O)NC(=O)C(=O)OCC] |
| YTC03-6 | α-D-Gal | 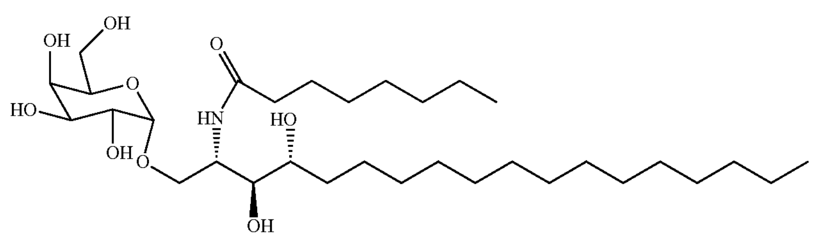 [SMILES: CCCCCCCCCCCCCC[C@@H](O)[C@@H](O)[C@H](COC1OC(CO)C(O)C(O)C1O)NC(=O)CCCCCCC] |

TABLE 1-continued

| Compound | CHO group | Structure |
|---|---|---|
| YTC03-07 | α-D-Gal | 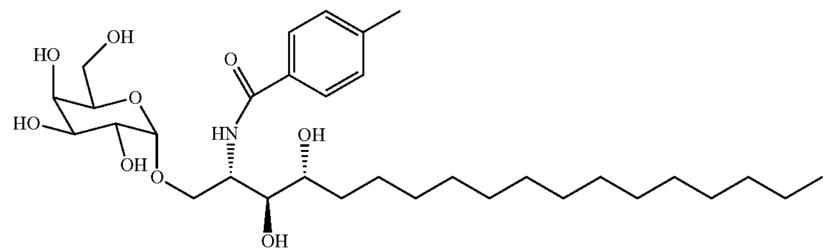 [SMILES: CCCCCCCCCCCCCC[C@@H](O)[C@@H](O)[C@H](COC1OC(CO)C(O)C(O)C1O)NC(=O)c1ccc(C)cc1] |
| YTC03-15 | α-D-Gal | 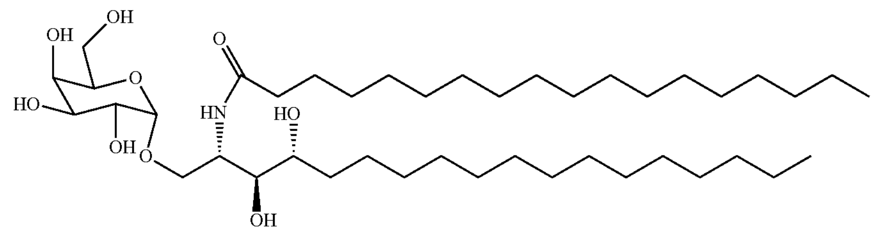 [SMILES: CCCCCCCCCCCCCCCCCC(=O)N[C@@H](COC1OC(CO)C(O)C(O)C1O)[C@H](O)[C@H](O)CCCCCCCCCCCCCC] |
| YTC03-16 | α-D-Gal | 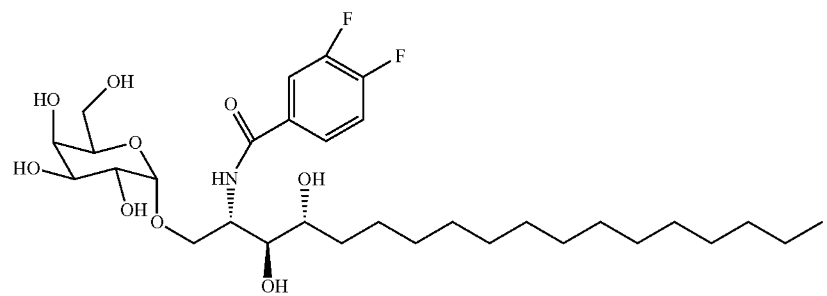 [SMILES: CCCCCCCCCCCCCC[C@@H](O)[C@@H](O)[C@H](COC1OC(CO)C(O)C(O)C1O)NC(=O)c1ccc(F)c(F)c1] |

TABLE 1-continued

| Compound | CHO group | Structure |
|---|---|---|
| YTC03-17 | α-D-Gal | (diphenylacetyl amide, phytosphingosine, α-D-Gal) |
| YTC03-22 | α-D-Gal | (3-bromobenzoyl amide, phytosphingosine, α-D-Gal) |
| YTC03-24 | α-D-Gal | (3,4-dimethoxyphenylacetyl amide, phytosphingosine, α-D-Gal) |

TABLE 1-continued

| Compound | CHO group | Structure |
|---|---|---|
| YTC03-25 | α-D-Gal | 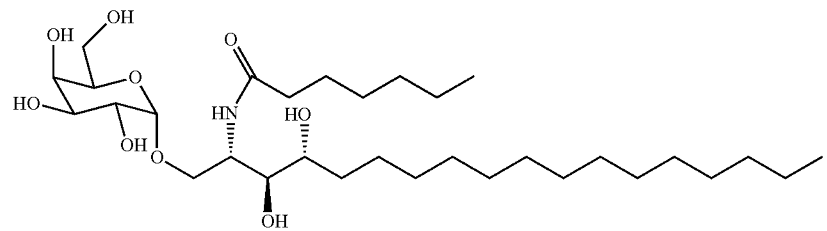 [SMILES: CCCCCCCCCCCCCC[C@@H](O)[C@@H](O)[C@H](COC1OC(CO)C(O)C(O)C1O)NC(=O)CCCCCC] |
| YTC03-30 | α-D-Gal | 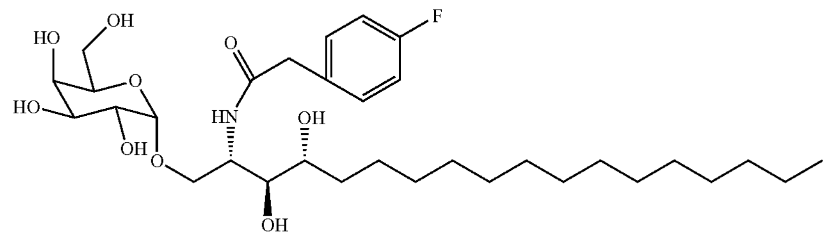 |
| YTC03-33 | α-D-Gal | 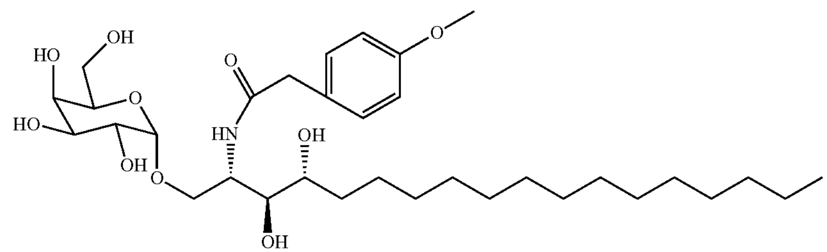 [SMILES: CCCCCCCCCCCCCC[C@@H](O)[C@@H](O)[C@H](COC1OC(CO)C(O)C(O)C1O)NC(=O)Cc1ccc(OC)cc1] |
| YTC03-34 | α-D-Gal | 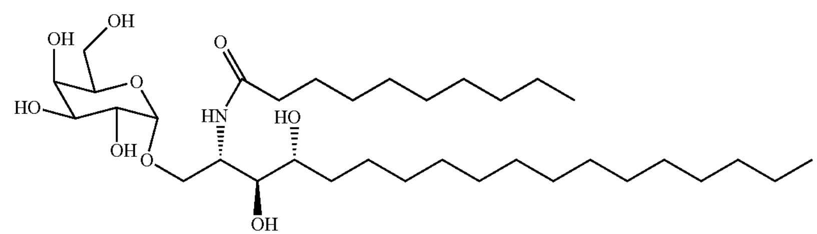 [SMILES: CCCCCCCCCCCCCC[C@@H](O)[C@@H](O)[C@H](COC1OC(CO)C(O)C(O)C1O)NC(=O)CCCCCCCCC] |

TABLE 1-continued

| Compound | CHO group | Structure |
|---|---|---|
| YTC03-35 | α-D-Gal | 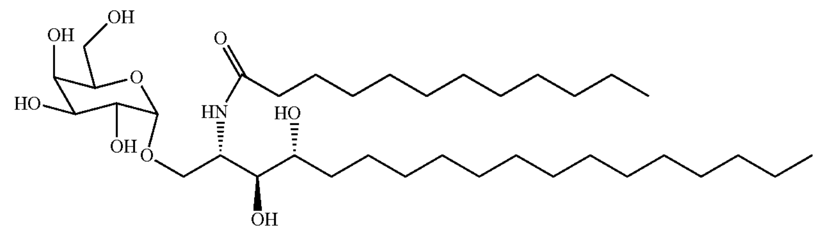 [SMILES: CCCCCCCCCCCCCC[C@@H](O)[C@@H](O)[C@H](COC1OC(CO)C(O)C(O)C1O)NC(=O)CCCCCCCCCCC] |
| YTC03-39 | α-D-Gal | 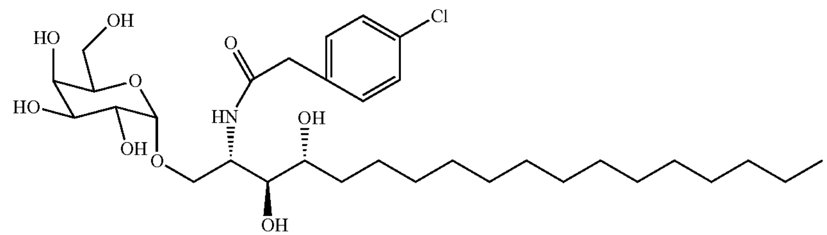 [SMILES: CCCCCCCCCCCCCC[C@@H](O)[C@@H](O)[C@H](COC1OC(CO)C(O)C(O)C1O)NC(=O)Cc1ccc(Cl)cc1] |
| YTC03-41 | α-D-Gal | 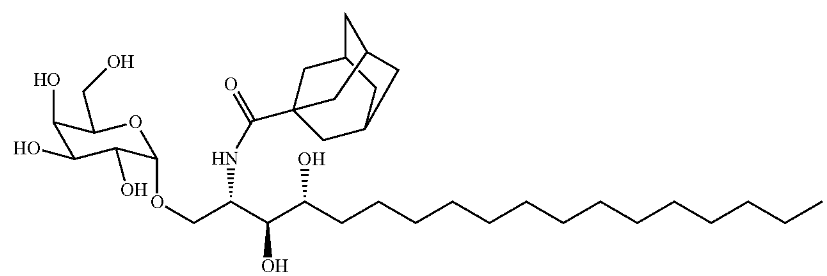 [SMILES: CCCCCCCCCCCCCC[C@@H](O)[C@@H](O)[C@H](COC1OC(CO)C(O)C(O)C1O)NC(=O)C12CC3CC(CC(C3)C1)C2] |
| BF1508-84 | α-D-Gal | 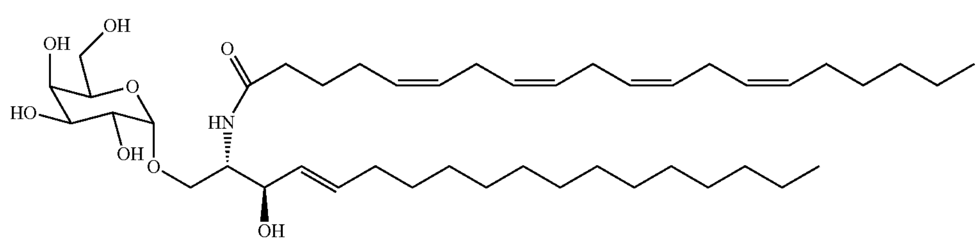 [SMILES: CCCCC/C=C\C/C=C\C/C=C\C/C=C\CCCC(=O)N[C@@H](COC1OC(CO)C(O)C(O)C1O)[C@H](O)/C=C/CCCCCCCCCCCCC] |

TABLE 1-continued
| Compound | CHO group | Structure |
|---|---|---|
| RF03-1 (C-glycoside) | α-D-Gal | 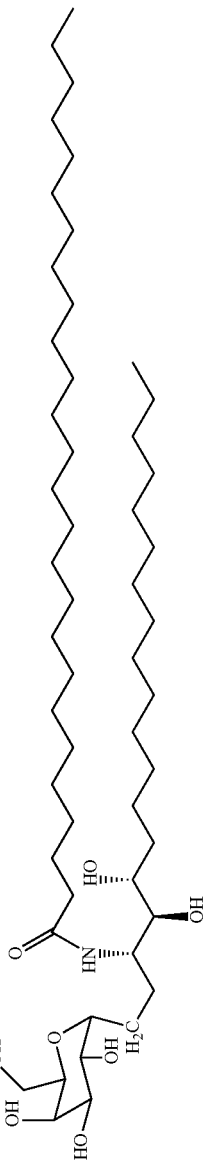 |

In a modified bacterium of the invention, a ceramide-like glycolipid antigen is "physically associated" with a bacterial cell to produce a "modified bacterium." By "physically associated" is meant a direct interaction with the bacterial cell, e.g., intercalation of the ceramide-like glycolipid into the plasma membrane or lipid-rich surface of a bacterial cell wall, e.g., a mycobacterial cell wall, by standard methods known to those of ordinary skill in the art. In certain embodiments, the ceramide-like glycolipid is physically associated with a bacterial cell wall through non-covalent means. For example, bacterial cells grown in the presence of ceramide-like glycolipid will incorporate the ceramide-like glycolipid into their cell walls. In one aspect of the invention, a ceramide-like glycolipid that is physically associated through non-covalent interactions to a bacterial cell remains extractable from the bacterial cell wall and ceramide-like glycolipid retains its chemical structure and biological activity after extraction. Detection of the ceramide-like glycolipid physically associated with the cell wall can be accomplished by methods known to one of skill in the art. By stably binding a ceramide-like glycolipid antigen to a bacterial cell wall, a ceramide-like glycolipid/bacterial complex can be made. In certain embodiments, the compositions of the invention allow for simultaneous administration of a ceramide-like glycolipid antigen and a bacterial cell, e.g., presentation of a glycolipid modified mycobacterial cell to an antigen presenting cell. In certain embodiments, ceramide-like glycolipids are incorporated into a mycobacterial cell wall. The bacterial cell, e.g., mycobacterial cell, can be a killed, live and/or attenuated bacterial cell. In another embodiment, the bacterial cell can be recombinant.

A modified bacterium of the present invention can comprise a single ceramide-like glycolipid antigen, or can comprise heterogeneous mixtures of ceramide-like glycolipid antigens. That is, populations of bacterial cells can be physically associated with a single ceramide-like glycolipid antigen or can be physically associated with to a mixture of ceramide-like glycolipid antigens.

A modified bacterium of the invention, e.g., a ceramide-like glycolipid/bacterial complex of the present invention, or a composition or a vaccine composition comprising the same can be labeled, so as to be directly detectable, or can be used in conjunction with secondary labeled immunoreagents which will specifically bind the compound, e.g., for detection or diagnostic purposes. Labels of interest can include dyes, enzymes, chemiluminescers, particles, radioisotopes, or other directly or indirectly detectable agent. Alternatively, a second stage label can be used, e.g. labeled antibody directed to one of the constituents of the compound of the invention.

Examples of suitable enzyme labels include, but are not limited to malate dehydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, and acetylcholine esterase.

Examples of suitable radioisotopic labels include $^3$H, $^{111}$In, $^{125}$I, $^{131}$I, $^{32}$P, $^{35}$S, $^{14}$C, $^{51}$Cr, $^{57}$To, $^{58}$Co, $^{59}$Fe, $^{75}$Se, $^{152}$Eu, $^{90}$Y, $^{67}$Cu, $^{217}$Ci, $^{211}$At, $^{212}$Pb, $^{47}$Sc, $^{109}$Pd, etc. Examples of suitable non-radioactive isotopic labels include $^{157}$Gd, $^{55}$Mn, $^{162}$Dy, $^{52}$Tr, and $^{56}$Fe.

Examples of suitable fluorescent labels include an $^{152}$Eu label, a fluorescein label, an isothiocyanate label, a rhodamine label, a phycoerythrin label, a phycocyanin label, an allophycocyanin label, an o-phthaldehyde label, and a fluorescamine label.

Examples of chemiluminescent labels include a luminal label, an isoluminal label, an aromatic acridinium ester label, an imidazole label, an acridinium salt label, an oxalate ester label, a luciferin label, a luciferase label, and an aequorin label.

Examples of nuclear magnetic resonance contrasting agents include heavy metal nuclei such as Gd, Mn, and Fe.

Typical techniques for binding the above-described labels to ceramide-like glycolipids or polypeptides of the invention are provided by Kennedy et al., *Clin. Chinn. Acta* 70:1-31 (1976), and Schurs et al., *Clin. Chien. Acta* 81:1-40 (1977). Coupling techniques mentioned in the latter are the glutaraldehyde method, the periodate method, the dimaleimide method, the m-maleimidobenzyl-N-hydroxy-succinimide ester method, all of which methods are incorporated by reference herein.

In certain embodiments, a ceramide-like glycolipid comprises a glycosylceramide or analog thereof or an α-galactosylceramide or analog thereof.

In further embodiments, the glycosylceramide or analog thereof comprises Formula I:

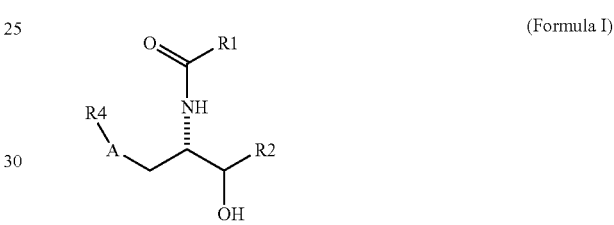

(Formula I)

wherein R1 is a linear or branched $C_1$-$C_{27}$ alkane or $C_2$-$C_{27}$ alkene; or R1 is —C(OH)—R3 wherein R3 is a linear or branched $C_1$-$C_{76}$ alkane or $C_2$-$C_{76}$ alkene; or R1 is a $C_6$-$C_{27}$ alkane or alkene wherein (i) the $C_6$-$C_{27}$ alkane or alkene is substituted with a $C_5$-$C_{15}$ cycloalkane, $C_5$-$C_{15}$ cycloalkene, heterocycle, or aromatic ring or (ii) the $C_6$-$C_{27}$ alkane or alkene includes, within the $C_6$-$C_{27}$ alkyl or alkenyl chain, a $C_5$-$C_{15}$ cycloalkane, $C_5$-$C_{15}$ cycloalkene, heterocycle, or aromatic ring;

R2 is one of the following (a)-(e):
 (a) —$CH_2(CH_2)_xCH_3$,
 (b) —$CH(OH)(CH_2)_xCH_3$,
 (c) —$CH(OH)(CH_2)_xCH(CH_3)_2$,
 (d) —CH=$CH(CH_2)_xCH_3$,
 (e) —$CH(OH)(CH_2)_xCH(CH_3)CH_2CH_3$,
 wherein X is an integer ranging from 4-17;

R4 is an α-linked or a β-linked monosaccharide, or when R1 is a linear or branched $C_1$-$C_{27}$ alkane, R4 is:

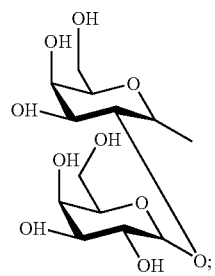

and
A is O or —$CH_2$.

In another embodiment, the α-galactosylceramide or analog thereof comprises Formula II:

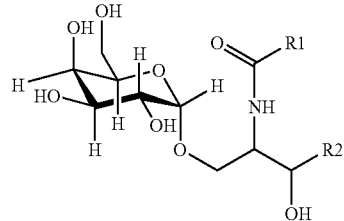

(Formula II)

wherein

R1 is a linear or branched $C_1$-$C_{27}$ alkane or $C_7$-$C_{27}$ alkene; or R1 is —C(OH)—R3 wherein R3 is linear or branched $C_1$-$C_{26}$ alkane or $C_2$-$C_{26}$ alkene; and R2 is one of the following (a)-(e):
(a) —$CH_2(CH_2)_xCH_3$,
(b) —$CH(OH)(CH_2)_xCH_3$,
(c) —$CH(OH)(CH_2)_xCH(CH_3)_2$,
(d) —$CH=CH(CH_2)_xCH_3$,
(e) —$CH(OH)(CH_2)_xCH(CH_3)CH_2CH_3$, wherein X is an integer ranging from 4-17.

In another embodiment, the α-galactosylceramide or analog thereof comprises Formula III:

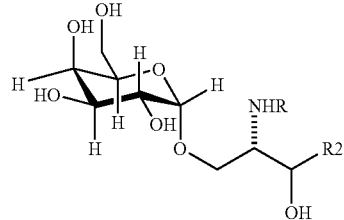

(Formula III)

wherein R is H or —C(O)R1, wherein R1 is a linear or branched $C_1$-$C_{27}$ alkane or $C_2$-$C_{27}$ alkene; or R1 is —C(OH)—R3 wherein R3 is a linear or branched $C_1$-$C_{26}$ alkane or $C_2$-$C_{26}$ alkene; or R1 is a $C_6$-$C_{27}$ alkane or alkene wherein (i) the $C_6$-$C_{27}$ alkane or alkene is substituted with a $C_5$-$C_{15}$ cycloalkane, $C_5$-$C_{15}$ cycloalkene, heterocycle, or aromatic ring or (ii) the $C_6$-$C_{27}$ alkane or alkene includes, within the $C_6$-$C_{27}$ alkyl or alkenyl chain, a $C_5$-$C_{15}$ cycloalkane, $C_5$-$C_{15}$ cycloalkene, heterocycle, or aromatic ring; or R1 is a —$(CH_2)_nR5$, wherein n is an integer ranging from 0-5, and R5 is —$C(O)OC_2H_5$, an optionally substituted $C_5$-$C_{15}$ cycloalkane, an optionally substituted aromatic ring, or an aralkyl, and R2 is one of the following (a)-(e):
(a) —$CH_2(CH_2)_xCH_3$,
(b) —$CH(OH)(CH_2)_xCH_3$,
(c) —$CH(OH)(CH_2)_xCH(CH_3)_2$,
(d) —$CH=CH(CH_2)_xCH_3$,
(e) —$CH(OH)(CH_2)_xCH(CH_3)CH_2CH_3$, wherein X is an integer ranging from 4-17.

In a further embodiment, R1 is selected from the group consisting of

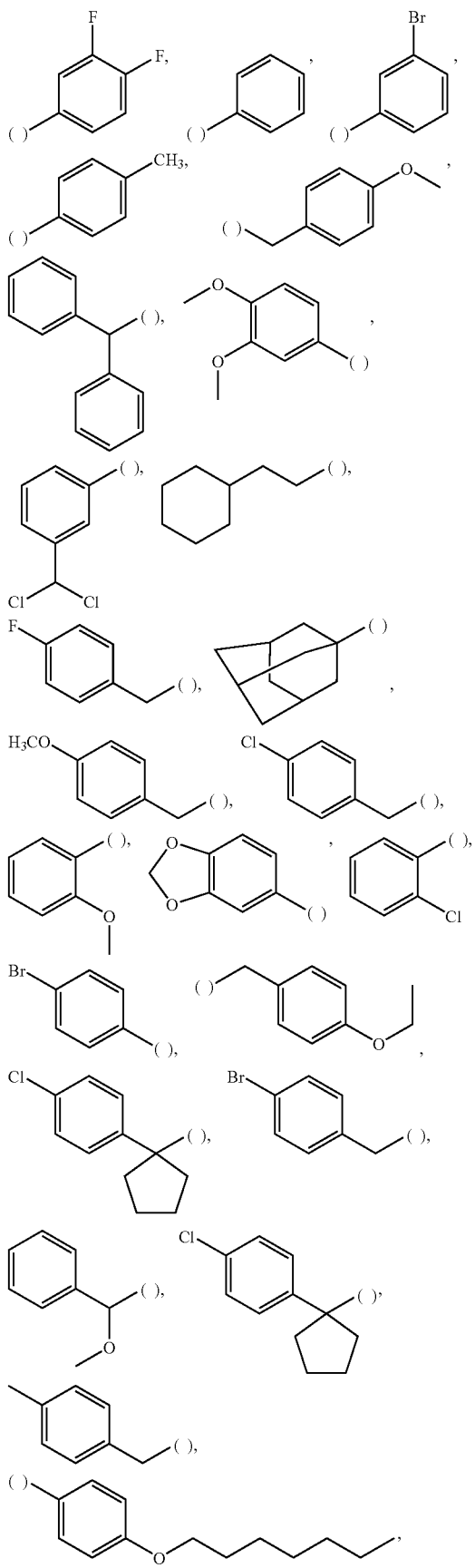

-continued

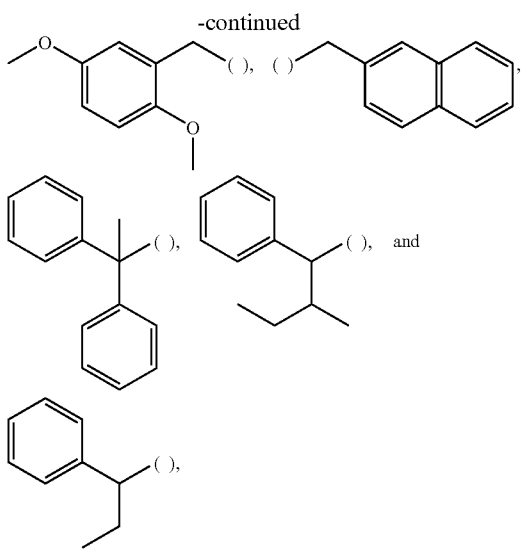

where ( ) represent the point of attachment of R1 to the compound of Formula III.

In another embodiment, the α-galactosylceramide or analog thereof comprises (2S,3S,4R)-1-O-(α-D-galactopyranosyl)-N-hexacosanoyl-2-amino-1,3,4-octadecanetriol (KRN7000) or (2S,3S)-1-O-(α-D-galactopyranosyl)-N-hexacosanoyl-2-amino-1,3-octadecanediol).

In another embodiment, the α-galactosylceramide or analog thereof comprises (2S,3S,4R)-1-CH$_2$-(α-galactopyranosyl)-N-hexacosanoyl-2-amino-1,3,4-octadecanetriol (α-C-GalCer).

Other non-limiting examples of ceramide-like glycolipids are described in Tsuji et al., U.S. Pat. No. 7,273,852; Taniguchi et al., U.S. Pat. No. 6,531,453; and Higa et al., U.S. Pat. No. 5,936,076, all of which are incorporated herein by reference in their entirety.

Natural Killer T (NKT) Cells

The natural immune system strikes a complex balance between highly aggressive, protective immune responses to foreign pathogens and the need to maintain tolerance to normal tissues. In recent years there has been increasing recognition that interactions among many different cell types contribute to maintaining this balance. Such interactions can, for example, result in polarized responses with either production of pro-inflammatory cytokines (e.g., interferon-gamma) by TH1 type T cells or production of interleukin-4 (IL-4) by TH2 type T cells that suppress TH1 activity. In a number of different animal models, T cell polarization to TH1 has been shown to favor protective immunity to tumors or infectious pathogens whereas T cell polarization to TH2 can be a critical factor in preventing development of cell-mediated autoimmune disease. The conditions that determine whether immune stimulation will result in aggressive cell-mediated immunity or in down regulation of such responses are highly localized in the sense that each tissue is comprised of a distinctive set of antigen presenting cells (APC) and lymphocyte lineages that interact to favor different immune responses. For example, under optimal conditions, the dendritic cells (DC) localized in a normal tissue can represent predominantly a lineage and stage of maturation that favors tolerogenic interactions and serves as a barrier to cell-mediated autoimmunity whereas a tumor or site of infection will attract mature myeloid dendritic cells that stimulate potent cell-mediated immune responses.

CD1d-restricted NKT cells are a unique class of non-conventional T cells that appear to play an important role in defining the outcome of immune stimulation in the local environment. They share with the larger class of NKT cells the expression of markers of both the T cell and natural killer (NK) cell lineages. As such, NKT cells are considered as part of innate immunity like NK cells and in humans their frequency in normal individuals can be as high as 2.0% of total T lymphocytes (Gumperz et al., J Exp Med 195:625 (2002); Lee et al., J Exp Med 195:637 (2002)).

CD1d-restricted NKT cells are distinguished from other NKT cells by their specificity for lipid and glycolipid antigens presented by the monomorphic MHC class Ib molecule, CD1d (Kawano et al., Science 278:1626-1629 (1997)). CD1d is a non-MHC encoded molecule that associates with β2-microglobulin and is structurally related to classical MHC class I molecules. CD1d has a hydrophobic antigen-binding pocket that is specialized for binding the hydrocarbon chains of lipid tails or hydrophobic peptides. Zeng et al., Science 277: 339-345, (1997). CD1d is known to bind a marine sponge derived α-glycosylated sphingolipid, α-galactosylceramide (α-GalCer), and related molecules such as ceramide-like glycolipid antigens with α-linked galactose or glucose but not mannose. Kawano et al., Science 278:1626-1629 (1997); and Zeng et al., Science 277: 339-345 (1997). As discussed herein, the ability to activate CD1d-restricted NKT cells by stimulation with α-GalCer or related molecules bound to CD1d of antigen presenting cells has greatly facilitated functional analysis of this non-conventional T cell subset. In the absence of inflammation, CD1d-restricted NKT cells have been shown to localize preferentially in certain tissues like thymus, liver and bone marrow (Wilson et al., Trends Mol Med 8:225 (2002)) and antitumor activity of NKT cells has been mainly investigated in mouse liver metastasis.

NKT cells have an unusual ability of secreting both TH1 and TH2 cytokines and potent cytotoxic as well as regulatory functions have been documented in inflammation, autoimmunity and tumor immunity (Bendelac et al., Science 268:863 (1995); Chen and Paul, J Immunol 159:2240 (1997); and Exley et al., J Exp Med 186:109 (1997)).

Among the CD1d-restricted NKT cells is a subset, referred to herein as "iNKT cells," that express a highly conserved αβT cell receptor (TCR). In humans this invariant TCR is comprised of Vα24Jα15 in association with Vβ11 whereas in mice the receptor comprises the highly homologous Vα14Jα18 and Vβ8.2. Other CD1d-restricted NKT cells express more variable TCR. Both TCR invariant and TCR variant classes of CD1d-restricted T cells can be detected by binding of CD1d-tetramers loaded with α-GalCer (Benlagha et al., J Exp Med 191:1895-1903 (2000); Matsuda et al., J Exp Med 192:741-754 (2000); and Karadimitris et al., Proc Natl Acad Sci USA 98:3294-3298 (2001)). CD1d-restricted NKT cells, as defined in this application (CD1d-restricted NKT), include cells that express either invariant or variant TCR and that bind or are activated by CD1d loaded with either α-GalCer or with related ceramide-like glycolipid antigens. CD1d-restricted NKT cells, as defined in this application (CD1d-NKT), include cells that express either invariant or variant TCR and that bind or are activated by CD1d loaded with either α-GalCer or with related sphingolipids that have α-linked galactose or glucose including molecules such as OCH, which differs from α-GalCer by having a shortened long-chain sphingosine base (C5 vs. C14) and acyl chain (C24 vs. C26) (Miyamoto et al., Nature 413:531-4 (2001)).

CD1d-restricted NKT have been shown to have direct cytotoxic activity against targets that express CD1d. It is likely, however, that the effect of CD1d-restricted NKT on immune responses is amplified through recruitment of other lymphocytes either by direct interaction or, perhaps even more importantly, by indirect recruitment through interaction with DC. CD1d-restricted NKT have the unique ability to secrete large quantities of IL-4 and IFN-γ early in an immune response. Secretion of IFN-γ induces activation of DC which produce interleukin-12 (IL-12). IL-12 stimulates further IFN-γ secretion by NKT cells and also leads to activation of NK cells which secrete more IFN-γ.

Since CD1d-restricted NKT are able to rapidly secrete large amounts of both IL-4 and IFN-γ, the polarization of immune responses will depend on whether the effect of pro-inflammatory IFN-γ or anti-inflammatory IL-4 cytokines predominate. This has been reported to be, in part, a function of the relative frequency of different subsets of CD1d-restricted NKT. These subsets include (i) an invariant CD1d-restricted NKT population that is negative for both CD4 and CD8 and that gives rise to predominantly a TH1 type response including secretion of pro-inflammatory IFN-γ and TNF-α and (ii) a separate population of CD1d-restricted NKT that is CD4+ and that gives rise to both a TH1 type and TH2 type response including secretion of the anti-inflammatory Th2-type cytokines IL-4, IL-5, IL-10 and IL-13 (Lee et al., *J Exp Med* 195:637-41 (2002); and Gumperz et al., *J Exp Med* 195:625-36 (2002)). In addition, NKT cell activity is differentially modulated by depending on the particular ceramide-like glycolipid bound to CD1d (see, e.g., US Patent Application Publication No. 2006/0052316). Local factors that influence activation of CD1d-restricted NKT subsets include the cytokine environment and, importantly, the DC that are recruited to that environment.

A family of ceramide-like glycolipids (i.e., α-galactosyl-ceramide (α-GalCer) and related α-glycosyl ceramides), have been shown stimulate strong CD1d-restricted responses by murine NKT cells (Kawano et al., 1997). These compounds contain an α-anomeric hexose sugar (galactose or glucose being active for NKT cell recognition), distinguishing them from the ceramides that commonly occur in mammalian tissues which contain only β-anomeric sugars. These compounds are known to occur naturally in marine sponges, the source from which they were originally isolated, and became of interest to immunologists when it was demonstrated that α-GalCer induced dramatic tumor rejection as a result of immune activation when injected into tumor bearing mice (Kobayashi et al., *Oncol. Res.* 7:529-534 (1995)). Subsequently, this activity was linked to the ability of α-GalCer to rapidly activate NKT cells through a CD dependent mechanism. It has now been shown that α-GalCer binds to CD1d, thus creating a molecular complex that has a measurable affinity for the TCRs of NKT cells (Naidenko et al., *J Exp. Med.* 190:1069-1080 (1999); Matsuda et al., *J. Exp. Med.* 192:741 (2000); Benlagha et al., *J. Exp. Med.* 191:1895-1903 (2000)). Thus, α-GalCer provides a potent agent that can enable activation of the majority of NKT cells both in vitro and in vivo.

The most extensively studied NKT activating α-GalCer, called KRN7000 in the literature, is a synthetic molecule that has a structure similar to natural forms of α-GalCer that were originally isolated from a marine sponge on the basis of their anti-cancer activity in rodents (Kawano et al., *Science* 278: 1626-1629 (1997); Kobayashi et al., 1995; Iijima et al., *Bioorg. Med. Chem.* 6:1905-1910 (1998); Inoue et al., *Exp. Hematol.* 25:935-944 (1997); Kobayashi et al., *Bioorg. Med. Chem.* 4:615-619 (1996a) and *Biol. Pharm. Bull.* 19:350-353 (1996b); Uchimura et al., *Bioorg. Med. Chem.* 5:2245-2249 (1997a); Uchimura et al., *Bioorg. Med. Chem.* 5:1447-1452 (1997b); Motoki et al., *Biol. Pharm. Bull.* 19:952-955 (1996a); Nakagawa et al., *Oncol. Res.* 10:561-568 (1998); Yamaguchi et al., *Oncol. Res.* 8:399-407 (1996)). One synthetic analogue of KRN7000 with a truncated sphingosine base showed an enhanced ability to suppress autoimmunity in a mouse model of experimental allergic encephalomyelitis (EAE) (Miyamoyo et al., *Nature* 413:531-534 (2001)). Other variants altered in the α-GalCer sphingosine base are identified in U.S. Pat. No. 5,936,076.

A large body of literature dating from November 1997 to the present time has studied the mechanism by which KRN7000 activates the immune system of mammals (Kawano et al., *Science* 278:1626-1629 (1997); Benlagha et al., *J. Exp. Med.* 191:1895-1903 (2000); Burdin et al., *Eur. J. Immunol.* 29:2014-2025 (1999); Crowe et al., *J. Immunol.* 171:4020-4027 (2003); Naidenko et al., *J Exp. Med.* 190: 1069-1080 (1999); Sidobre et al., *J. Immunol.* 169:1340-1348 (2002); Godfrey et al., *Immunol. Today* 21:573-583 (2000); Smyth and Godfrey, *Nat. Immunol.* 1:459-460 (2000)). These studies uniformly show that the proximal mechanism for the effect of KRN7000 is the binding of this compound to a CD1d protein, which is expressed on most hematopoietic cells, as well as some epithelial and other cell lineages. The binding of KRN7000 to CD1d creates a molecular complex that is recognized with high affinity by the T cell antigen receptors (TCRs) of a subset of T lymphocytes called natural killer T cells (NKT cells). Recognition of the KRN7000/CD1d complex leads to rapid activation of the NKT cells, which reside in the liver, spleen and other lymphoid organs and have the potential to traffic to potentially any tissue. Activated NKT cells rapidly secrete a wide range of chemokines and other cytokines, and also have the capability of activating other cell types such as dendritic cells and natural killer (NK) cells. The chain of events that follows the activation of NKT cells by KRN7000/CD1d complexes has been shown to have many potential downstream effects on the immune system. For example, in the setting of certain types of infections this can lead to an adjuvant effect that boosts the adaptive immunity to the infection and promotes healing. Or, in the setting of certain types of autoimmune diseases, the activation of NKT cells by KRN7000 can alter the course of the autoimmune response in a way that suppresses tissue destruction and ameliorates the disease.

The functions of NKT lymphocytes remain incompletely resolved, but a variety of studies point to an important role for these T cells in the regulation of immune responses. A hallmark of NKT cells is their rapid production of large quantities of both IL-4 and IFN-γ upon stimulation through their α-βTCRs (Exley et al., *J. Exp. Med.* 186:109 (1997). In fact, their identification as perhaps the major cell responsible for the early production of IL-4 during immune activation suggested that they may play a critical role in polarizing type 2 (Th2) T cell responses. In this regard, it is not surprising that NKT cells have been identified to play a significant role in determining the outcome of infections with a variety of different pathogens in mice.

A number of indirect mechanisms contribute to the protective effect of CD1d-restricted NKT cells. Activation of NKT cells by administration of α-GalCer in vivo results in concomitant activation of NK cells (Eberl and MacDonald, *Eur. J. Immunol.* 30:985-992 (2000); and Carnaud et al., *J. Immunol.* 163:4647-4650 (1999)). In mice deficient in NKT cells, α-GalCer is unable to induce cytotoxic activity by NK cells. NKT cells also enhance the induction of classical MHC class I restricted cytotoxic T cells (Nishimura et al., *Int Immunol* 12:987-94 (2000); and Stober et al., *J Immunol* 170:2540-8 (2003)).

The availability of a defined antigen, e.g., α-GalCer and related antigens, that can be employed to specifically activate CD1d-restricted NKT cells has made it possible to examine the role of these non-conventional T cells in a variety of immune responses.

Alpha-GalCer administration has an effect on a number of different microbial infections, including protective effects in murine malaria, fungal and hepatitis B virus infections. Kakimi et al., *J Exp Med* 192:921-930 (2000); Gonzalez-Aseguinolaza et al., *Proc Natl Acad Sci USA* 97:8461-8466 (2000); and Kawakami et al., *Infect Immun* 69:213-220 (2001). Dramatic effects of administration of α-GalCer have also been observed in animal models of tumor immunity. For example, stimulation with α-GalCer suppresses lung and liver metastases in an NKT dependent manner (Smyth et al., *Blood* 99:1259 (2002)). In addition, α-GalCer has been shown to have a protective effect against certain autoimmune diseases, including type 1 diabetes and experimental autoimmune encephalomyelitis (EAE, a well-known murine model system for multiple sclerosis). Hong S et al. *Nat. Med.* 7:1052-1056 (2001) and Miyamoto K. et al., *Nature* 413:531-534 (2001).

NKT Activity Assays

The ability of a composition of the present invention to modulate an immune response can be readily determined by an in vitro assay. NKT cells for use in the assays include transformed NKT cell lines, or NKT cells which are isolated from a mammal, e.g., from a human or from a rodent such as a mouse. NKT cells can be isolated from a mammal by sorting cells that bind CD1d:α-GalCer tetramers. See, for example, Benlagha et al., *J Exp Med* 191:1895-1903 (2000); Matsuda et al., *J Exp Med* 192:741-754 (2000); and Karadimitris et al., *Proc Natl Acad Sci USA* 98:3294-3298 (2001). A suitable assay to determine if a compound or composition of the present invention is capable of modulating the activity of NKT cells is conducted by co-culturing NKT cells and antigen presenting cells, adding the particular compound or composition of interest to the culture medium that targets either the antigen presenting cells or the NKT cells directly, and measuring IL-4 or IFN-γ production. A significant increase or decrease in IL-4 or IFN-γ production over the same co-culture of cells in the absence of the compound or composition of the invention or in the presence of a compound or composition of the invention with a non-targeting antibody indicates stimulation or inhibition of NKT cells.

The NKT cells employed in the assays are incubated under conditions suitable for proliferation. For example, an NKT cell hybridoma is suitably incubated at about 37° C. and 5% CO2 in complete culture medium (RPMI 1640 supplemented with 10% FBS, penicillin/streptomycin, L-glutamine and $5 \times 10^{-5}$ M 2-mercaptoethanol). Serial dilutions of the compound can be added to the NKT cell culture medium. Suitable concentrations of the compound added to the NKT cells typically will be in the range of from $10^{-12}$ to $10^{-6}$ M. Use of antigen dose and APC numbers giving slightly submaximal NKT cell activation can be used to detect stimulation or inhibition of NKT cell responses by the compounds of the invention.

Alternatively, rather than measurement of an expressed protein such as IL-4 or IFN-γ, modulation of NKT cell activation can be determined by changes in antigen-dependent T cell proliferation as measured by radiolabelling techniques as are recognized in the art. For example, a labeled (e.g., tritiated) nucleotide can be introduced to an assay culture medium. Incorporation of such a tagged nucleotide into DNA serves as a measure of T cell proliferation. This assay is not suitable for NKT cells that do not require antigen presentation for growth, e.g., NKT cell hybridomas. A difference in the level of T cell proliferation following contact with the compound or composition of the invention indicates the complex modulates activity of the T cells. For example, a decrease in NKT cell proliferation indicates the compound or composition can suppress an immune response. An increase in NKT cell proliferation indicates the compound or composition can stimulate an immune response.

Additionally, the $^{51}$Cr release assay can be used to determine cytotoxic activity.

These in vitro assays can be employed to select and identify ceramide-like glycolipid/bacterial cell complexes and compositions comprising same that are capable of appropriately modulating an immune response. Assays described above, e.g., measurement of IL-4 or IFN-γ production or NKT cell proliferation, are employed to determine if contact with the compound modulates T cell activation.

In addition or alternatively, immunization challenge experiments in animals, e.g., mice, rabbits, non-human primates, can be used to identify ceramide-like glycolipid/bacterial cell complexes and compositions comprising same that are capable of appropriately modulating an immune response and that may be efficacious for treatment and/or prevention of bacterial diseases, e.g., tuberculosis, in humans. For example, mice can be vaccinated with ceramide-like glycolipid/bacterial cell complex, e.g., BCG/αGalCer or BCG/α-C-GalCer (e.g., $5 \times 10^6$ CFU/mouse) and challenged with an infectious bacteria, e.g., virulent strain *M. tuberculosis* H37Rv.

Methods Of Treatment

A modified bacterium, composition, or vaccine composition of the present invention can be used both to prevent a disease, and also to therapeutically treat a disease, e.g., a viral disease, a bacterial disease, a fungal disease, a parasitic disease, an allergic disease, or a proliferative diseases, e.g., cancer. In individuals already suffering from a disease, the present invention is used to further stimulate or modulate the immune system of the animal, thus reducing or eliminating the symptoms associated with that disease or disorder. As defined herein, "treatment" refers to the use of one or more modified bacteria, compositions, or vaccine compositions of the present invention to prevent, cure, retard, or reduce the severity of given disease symptoms in an animal, and/or result in no worsening of the disease over a specified period of time in an animal which has already contracted the disease and is thus in need of therapy.

The term "prevention" or "prevent" refers to the use of one or more modified bacteria, compositions, or vaccine compositions of the present invention to generate immunity in an animal which has not yet contracted a disease, thereby preventing or reducing disease symptoms if the animal is later disposed to develop that disease. The methods of the present invention therefore can be referred to as therapeutic methods or preventative or prophylactic methods. It is not required that any modified bacterium, composition, or vaccine composition of the present invention provide total immunity to a disease agent or totally cure or eliminate all disease symptoms.

As used herein, an "animal in need of therapeutic and/or preventative immunity" refers to an individual for whom it is desirable to treat, i.e., to prevent, cure, retard, or reduce the severity of certain disease symptoms, and/or result in no worsening of disease over a specified period of time.

An "effective amount" is that amount the administration of which to an individual, either in a single dose or as part of a series, is effective for treatment and/or prevention. An amount is effective, for example, when its administration results in a reduced incidence or severity of disease symptoms associated with *M. tuberculosis* relative to an untreated individual, as determined about two weeks after challenge with infectious *M. tuberculosis*. This amount varies depending upon the health and physical condition of the individual to be treated, the taxonomic group of individual to be treated (e.g. human, nonhuman primate, primate, etc.), the responsive capacity of the individual's immune system, the degree of protection desired, the formulation of the vaccine, a professional assessment of the medical situation, and other relevant factors. It is expected that the effective amount will fall in a relatively broad range that can be determined through routine trials.

The term "vertebrate" is intended to encompass a singular "vertebrate" as well as plural "vertebrates" and comprises mammals and birds, as well as fish, reptiles, and amphibians.

The term "mammal" is intended to encompass a singular "mammal" and plural "mammals," and includes, but is not limited to humans; primates such as apes, monkeys (e.g., owl, squirrel, cebus, rhesus, African green, patas, cynomolgus, and cercopithecus), orangutans, baboons, gibbons, and chimpanzees; canids such as dogs and wolves; felids such as cats, lions, and tigers; equines such as horses, donkeys, and zebras, food animals such as cows, pigs, and sheep; ungulates such as deer and giraffes; ursids such as bears; and others such as rabbits, mice, ferrets, seals, whales. In particular, the mammal can be a human subject, a food animal or a companion animal.

The term "bird" is intended to encompass a singular "bird" and plural "birds," and includes, but is not limited to feral water birds such as ducks, geese, terns, shearwaters, and gulls; as well as domestic avian species such as turkeys, chickens, quail, pheasants, geese, and ducks. The term "bird" also encompasses passerine birds such as starlings and budgerigars.

The invention provides methods of preventing or treating a disease in an animal in need of such treatment or prevention, comprising administering to an animal with that disease, or prone to contract that disease, a composition comprising a bacterial cell, e.g., a mycobacterial cell, and a ceramide-like glycolipid antigen wherein said ceramide-like glycolipid is incorporated into the cell wall of the bacterial cell as described herein. In further embodiments, the bacterial cell can be used as as a carrier for delivery of antigens from another pathogen or a tumor specific antigen.

The present invention also includes a method of modulating, i.e., either stimulating or inhibiting an immune response, comprising administering to an animal an effective amount of a composition comprising a bacterial cell, e.g., a mycobacterial cell, and a ceramide-like glycolipid, wherein said ceramide-like glycolipid is incorporated into the cell wall of the bacterial cell as described herein.

In certain embodiments, the methods of the invention include treating a disease, e.g., a mycobacterial disease, in an animal with the disease by administering to the animal with the disease a composition of the invention, e.g., a bacterium, e.g., a modified mycobacterium, e.g., a BCG cell physically associated with a ceramide-like glycolipid, e.g., incorporated into its cell wall in a non-covalent manner, in an amount sufficient to alter the progression of said disease.

In other embodiments, the methods of the invention include preventing a disease, e.g., a mycobacterial disease, in an animal in need of prevention of the disease by administering to the animal in need thereof a composition of the invention, e.g., a modified mycobacterium, e.g., a BCG cell physically associated with a ceramide-like glycolipid, e.g., incorporated into its cell wall in a non-covalent manner, in an amount sufficient to enhance an immune response against the bacterium or antigen encoded by the bacterium relative to administration of an unmodified bacterial cell lacking the ceramide-like glycolipid.

In further embodiments, the disease being treated or prevented can be, without limitation a viral, bacterial, fungal, or parasitic infectious disease, an allergy or a proliferative disease such as cancer. More specifically, the disease can be, e.g., tuberculosis, Hansen's disease, pulmonary disease resembling tuberculosis, lymphadenitis, skin disease, disseminated disease, bubonic plague, pneumonic plague, tularemia, Legionnaire's disease, anthrax, typhoid fever, paratyphoid fever, foodborne illness, listeriosis, malaria, HIV, SIV, HPV, RSV, influenza, hepatitis (HAV, HBV, and HCV).

In another embodiment the methods of the invention include enhancing an immune response to a bacterial cell, e.g., a mycobacterial cell, in an animal, comprising administering to the animal a modified bacterium of the invention, e.g., ceramide-like glycolipid incorporated into the cell wall of a bacterial cell; and wherein the modified bacterium is administered in an amount sufficient to enhance antigen specific CD8 T-cell responses against an antigen and enhance the activity of Natural Killer T (NKT) cells in said animal.

In another embodiment the methods of the invention include simultaneous administration of a ceramide-like glycolipid adjuvant and a bacterial cell, e.g., mycobacterial cell, to an antigen presenting cell by stably binding a ceramide-like glycolipid adjuvant to the cell wall of the bacterial cell to make a ceramide-like glycolipid/bacterial complex; and then administering the ceramide-like glycolipid/bacterial complex to the antigen presenting cell.

As used herein, an "subject in need thereof" refers to an individual for whom it is desirable to treat, i.e., to prevent, cure, retard, or reduce the severity of the symptoms of a disease, e.g., a bacterial infection, and/or result in no worsening of a disease over a specified period of time.

According to these methods, a modified bacterium, composition, or vaccine composition if the present invention can be administered in an amount sufficient to alter the progression of a disease.

"Immunization" (administration of a vaccine) is a common and widespread procedure and the vaccines of the invention used can be essentially any preparation intended for active immunological prophylaxis, including without limitation preparations of killed microbes of virulent strains and living microbes of attenuated strains. Stedman's Illustrated Medical Dictionary (24th edition), Williams & Wilkins, Baltimore, p. 1526 (1982). In some cases, vaccines must be administered more than once in order to induce effective protection; for example, known anti-toxin vaccines must be given in multiple doses.

The terms "priming" or "primary" and "boost" or "boosting" as used herein to refer to the initial and subsequent immunizations, respectively, i.e., in accordance with the definitions these terms normally have in immunology. However, in certain embodiments, e.g., where the priming component and boosting component are in a single formulation, initial and subsequent immunizations may not be necessary as both the "prime" and the "boost" compositions are administered simultaneously. See also, McShane H, *Cure Opin Mol Ther* 4(1):13-4 (2002) and Xing Z and Charters T J, *Expert Rev Vaccines* 6(4):539-46 (2007), both incorporated herein by reference.

In other embodiments, one or more compositions of the present invention are utilized in a "prime boost" regimen. In these embodiments, one or more vaccine compositions of the present invention are delivered to a vertebrate, thereby priming the immune response of the vertebrate to a bacterial antigen, e.g., a mycobacterial antigen, and then a second immunogenic composition is utilized as a boost vaccination. One or more vaccine compositions of the present invention are used to prime immunity, and then a second immunogenic composition, e.g., a recombinant bacterial vaccine, is used to boost the anti-bacterial immune response. The vaccine compositions can comprise one or more vectors for expression of one or more genes that encode immunogenic polypeptides as described herein.

The present invention further provides a method for generating, enhancing, or modulating a protective and/or therapeutic immune response to a pathogen, e.g., a bacterial, fungal, viral, or parasitic pathogen, or a tumor antigen, in a vertebrate, comprising administering to a vertebrate in need of therapeutic and/or preventative immunity one or more of the modified bacterium, compositions, or vaccine compositions described herein. In this method, the composition includes a modified bacterium, e.g., a mycobacterium comprising a ceramide-like glycolipid incorporated into its cell wall.

In certain embodiments, the modified bacterium, composition, or vaccine composition of the invention, e.g., BCG/αGalCer or BCG/α-C-GalCer can be used to reduce the dose required to obtain a favorable response to the vaccine. This would have the potential benefits of reducing local and systemic toxicity, thus increasing the safety profile of the vaccine. In addition, this could have the benefit of allowing for reduced cost of production.

Certain embodiments of the present invention include a method of reducing or eliminating the anergic response of NKT cells to multiple administrations of ceramide-like glycolipid antigens administered by themselves, which are therefore presented to NKT cells in the context of a bacterial cell wall. It has been shown that multiple administrations of α-GalCer, administered by itself, causes NKT cells to become non-responsive for an extended period of time. The present invention, in which glycolipids such as α-GalCer are administered as part of a ceramide-like glycolipid/bacterial cell complex, may protect NKT cells from anergy in response to antigen, and allow for a prolonged response upon multiple administrations. Accordingly, NKT cells are activated in response to stimulation with ceramide-like glycolipid/bacterial cell complexes loaded with a ceramide-like glycolipid antigen of the present invention and furthermore, NKT cells can be reactivated in response to restimulation by ceramide-like glycolipid/bacterial cell complexes loaded with a ceramide-like glycolipid antigen of the present invention.

According to the methods of the present invention, a composition comprising a bacterial cell and a ceramide-like glycolipid antigen as described herein is administered to modulate an immune response in an animal, e.g., a vertebrate, e.g., a mammal, e.g., a human. In certain embodiments, the methods of the present invention result in the enhancement of an immune response, e.g., to an immunogen delivered before, after, or concurrently with a ceramide-like glycolipid/bacterial cell complex. Administration of ceramide-like glycolipid/bacterial cell complexes of the invention, e.g., with an immunogen, may typically result in the release of a cytokines from immune cells, e.g., NKT cells or NK cells. Cytokines released in response to administration of a modified bacterium, composition, or vaccine composition of the invention may be those associated with a TH1-type immune response, e.g., interferon gamma and TNF-alpha. Alternatively, or in addition, administration of a modified bacterium, composition, or vaccine composition of the present invention may result in the release of cytokines associated with a TH2-type immune response, e.g., IL-4, IL-5, IL-10, or IL-13. Alternatively, or in addition, administration of a modified bacterium, composition, or vaccine composition of the present invention may result in the release of other cytokines, e.g., IL-2, IL-1β, IL-12, IL-17, IL-23, TNF-β/LT, MCP-2, oncostatin-M, and RANTES. Methods to modulate the type of cytokines released include varying the ceramide-like glycolipid antigen of the ceramide-like glycolipid/bacterial cell complex. Choosing and testing various ceramide-like glycolipid antigens for their effect on cytokine release from NKT or other immune cells can be performed using in vitro assays described elsewhere herein and in Porcelli, U.S. Patent Appl. Publ. No. 2006/0052316, as well as by additional methods well-known by those of ordinary skill in the art. Administration of ceramide-like glycolipid/bacterial cell complexes of the present invention and vaccine compositions comprising same may further modulate an immune response by inducing proliferation of NKT cells, and also by inducing recruitment and or activation of other immune cells including, but not limited to NK cells, CTLs, other T lymphocytes, e.g., CD8+ or CD4+ T lymphocytes, dendritic cells, B lymphocytes, and others.

In certain embodiments, administration of ceramide-like glycolipid/bacterial cell complexes of the present invention and compositions comprising same affects one or more NKT cell activities such as, but not limited to cell proliferation, the production of one or more cytokines, or recruitment and/or activation of non-NKT immune system cells including, but not limited to NK cells, CTLs, other T lymphocytes, e.g., CD8+ or CD4+ T lymphocytes, dendritic cells, B lymphocytes, and others.

Certain embodiments of the present invention involve the use of ceramide-like glycolipid/bacterial cell complexes of the invention as recombinant vaccines used to modulate an immune response to an immunogen, e.g., a pathogen antigen or tumor antigen, that is expressed by the bacterial cell/ceramide-like glycolipid complex. Accordingly, the present invention provides a method of inducing an immune response to an immunogen in an animal, where the method comprises administering to an animal in need thereof a composition comprising an immunogen, which is present in a ceramide-like glycolipid/bacterial cell complex. According to this embodiment, the ceramide-like glycolipid/bacterial cell complex is administered in an amount sufficient to induce the immune response against the immunogen, e.g., bacterial pathogen or immunogen expressed by the recombinant bacteria, relative to administration of the immunogen without the ceramide-like glycolipid/bacterial cell complex. A ceramide-like glycolipid/bacterial cell complex for use as an vaccine can in certain embodiments be a recombinant bacterial cell that presents a recombinant antigen. In other embodiments, the immune response is to the bacterial cell of the ceramide-like glycolipid/bacterial cell complex. In other embodiments, a ceramide-like glycolipid/bacterial cell complex for use as an vaccine can be targeted to a particular organ, tissue, cell or cell surface marker as described, e.g., in Bruno et al. U.S. Patent Appl. Publ. No. 2006/0269540.

In certain embodiments, ceramide-like glycolipid/bacterial cell complexes of the present invention and compositions comprising same are administered as a therapeutic vaccine, e.g., to an animal already suffering from a disease such as tuberculosis. According to these methods, the immune response elicited by a modified bacterium of the invention is effective in treating, e.g., affecting the outcome of the disease by reducing symptoms or lessening the severity of the disease, and the ceramide-like glycolipid/bacterial cell complex is administered in an amount sufficient to modulate the immune response against the immunogen relative to administration of the immunogen in the absence of the ceramide-like glycolipid/bacterial cell complex. Alternatively, ceramide-like glycolipid/bacterial cell complexes of the present invention and compositions comprising same are administered as a prophylactic vaccine, i.e., to prevent, or reduce symptoms to a disease, such as an infectious disease that might be contracted by that animal in the future. According to these methods, the immune response elicited by the ceramide-like glycolipid/bacterial cell complexes is effective in preventing, e.g., affecting the outcome of the disease by reducing symptoms or lessening the severity of the disease, and the ceramide-like glycolipid/bacterial cell complex is administered in an amount sufficient to modulate the immune response against the immunogen relative to administration of the immunogen in the absence of the ceramide-like glycolipid/bacterial cell complex.

The present invention also provides ceramide-like glycolipid/bacterial cell complex compositions for use in the methods described herein. Such compositions comprise a bacterial cell and a ceramide-like glycolipid as described elsewhere herein. For example, ceramide-like glycolipid/bacterial cell complex compositions of the present invention can include ceramide-like glycolipid/mycobacterial cell complex, e.g., αGalCer/BCG and α-C-GalCer/BCG.

The methods, modified bacteria, compositions, or vaccine compositions as described herein are also useful for raising an immune response against infectious agents, e.g., a ceramide-like glycolipid/bacterial cell complex wherein the bacterial cell of the complex expresses a heterologous antigen, e.g., a viral antigen, a bacterial antigen, a fungal antigen, or a parasitic antigen. Infectious agents that can cause disease or symptoms that can be treated by the methods, modified bacteria, compositions, or vaccine compositions of the invention include, but are not limited to viral, bacterial, fungal, and parasitic agents. Examples of viruses, include, but are not limited to the following DNA and RNA viral families: Arbovirus, Adenoviridae, Arenaviridae, Arterivirus, Birnaviridae, Bunyaviridae, Caliciviridae, Circoviridae, Coronaviridae, Flaviviridae, Hepadnaviridae (hepatitis), Herpesviridae (such as, Cytomegalovirus, Herpes Simplex, Herpes Zoster), Mononegavirus (e.g., Paramyxoviridae, Morbillivirus, Rhabdoviridae), Orthomyxoviridae (e.g., Influenza), Papovaviridae, Parvoviridae, Picornaviridae, Poxyiridae (such as Smallpox or Vaccinia), Reoviridae (e.g., Rotavirus), Retroviridae (HTLV-I, HTLV-II, Lentivirus), and Togaviridae (e.g., Rubivirus). Viruses falling within these families can cause a variety of diseases or symptoms, including, but not limited to: arthritis, bronchiollitis, encephalitis, eye infections (e.g., conjunctivitis, keratitis), chronic fatigue syndrome, hepatitis (A, B, C, E, Chronic Active, Delta), meningitis, opportunistic infections (e.g., AIDS), pneumonia, Burkitt's Lymphoma, chickenpox, hemorrhagic fever, measles, mumps, parainfluenza, rabies, the common cold, Polio, leukemia, Rubella, sexually transmitted diseases, skin diseases (e.g., Kaposi's, warts), and viremia.

Similarly, bacterial or fungal agents that can cause disease or symptoms can be treated or prevented by the methods, modified bacterium, compositions, or vaccine compositions of the invention. These include, but are not limited to, the following Gram-Negative and Gram-positive bacterial families and fungi: Actinomycetales (e.g., *Corynebacterium, Mycobacterium, Norcardia*), Aspergillosis, Bacillaceae (e.g., Anthrax, *Clostridium*), Bacteroidaceae, Blastomycosis, *Bordetella, Borrelia*, Brucellosis, Candidiasis, *Campylobacter*, Coccidioidomycosis, Cryptococcosis, *Dennatocycoses*, Enterobacteriaceae (*Klebsiella, Salmonella, Serratia, Yersinia*), *Erysipelothrix, Helicobacter*, Legionellosis, Leptospirosis, *Listeria, Mycoplasmatales*, Neisseriaceae (e.g., *Acinetobacter*, Gonorrhea, Menigococcal), Pasteurellacea Infections (e.g., *Actinobacillus, Heamophilus, Pasteurella*), *Pseudomonas, Rickettsiaceae, Chlamydiaceae, Syphilis*, and *Staphylococcal*. These bacterial or fungal families can cause the following diseases or symptoms, including, but not limited to: bacteremia, endocarditis, eye infections (conjunctivitis, tuberculosis, uveitis), gingivitis, opportunistic infections (e.g., AIDS related infections), paronychia, prosthesis-related infections, Reiter's Disease, respiratory tract infections, such as Whooping Cough or Empyema, sepsis, Lyme Disease, Cat-Scratch Disease, Dysentery, Paratyphoid Fever, food poisoning, Typhoid, pneumonia, Gonorrhea, meningitis, Chlamydia, Syphilis, Diphtheria, Leprosy, Paratuberculosis, Tuberculosis, Hansen's disease, pulmonary disease resembling tuberculosis, Lymphadenitis, skin disease, disseminated disease, Lupus, Botulism, gangrene, tetanus, impetigo, Rheumatic Fever, Scarlet Fever, sexually transmitted diseases, skin diseases (e.g., cellulitis, *dermatocycoses*), toxemia, urinary tract infections, wound infections.

Moreover, the methods, modified bacteria, compositions, or vaccine compositions of the present invention can be used to treat or prevent diseases caused by parasitic agents. Those that can be treated by the compounds of the invention include, but are not limited to, the following families: amebiasis, babesiosis, coccidiosis, cryptosporidiosis, dientamoebiasis, dourine, ectoparasitic, giardiasis, helminthiasis, leishmaniasis, theileriasis, toxoplasmosis, trypanosomiasis, and trichomonas.

According to the disclosed methods, modified bacteria, compositions, or vaccine compositions for use in the methods of the present invention can be administered, for example, by intramuscular (i.m.), intravenous (i.v.), subcutaneous (s.c.), or intrapulmonary routes. Other suitable routes of administration include, but are not limited to intratracheal, transdermal, intraocular, intranasal, inhalation, intracavity, intraductal (e.g., into the pancreas), and intraparenchymal (i.e., into any tissue) administration. Transdermal delivery includes, but not limited to intradermal (e.g., into the dermis or epidermis), transdermal (e.g., percutaneous) and transmucosal administration (i.e., into or through skin or mucosal tissue). Intracavity administration includes, but not limited to administration into oral, vaginal, rectal, nasal, peritoneal, or intestinal cavities as well as, intrathecal (i.e., into spinal canal), intraventricular (i.e., into the brain ventricles or the heart ventricles), intraatri al (i.e., into the heart atrium) and sub arachnoid (i.e., into the sub arachnoid spaces of the brain) administration.

Compositions of the present invention further comprise a suitable carrier. Such compositions comprise a therapeutically effective amount of the ceramide-like glycolipid/mycobacteria complex and a pharmaceutically acceptable carrier or excipient. Such a carrier includes but is not limited to saline, buffered saline, dextrose, water, glycerol, ethanol, and combinations thereof. The formulation should suit the mode of administration.

Pharmaceutical Compositions

The term "pharmaceutically acceptable" refers to compositions that are, within the scope of sound medical judgment, suitable for contact with the tissues of human beings and animals without excessive toxicity or other complications commensurate with a reasonable benefit/risk ratio. In some embodiments, the compositions and vaccines of the present invention are pharmaceutically acceptable.

Ceramide-like glycolipid/bacterial cell complexes of the present invention can be administered in pharmaceutical compositions, e.g., vaccine compositions, in combination with one or more pharmaceutically acceptable excipients, carriers, or diluents. It will be understood that, when administered to a human patient, the total single or daily usage of the pharmaceutical compositions of the present invention will be decided by the attending physician within the scope of sound medical judgment. The specific therapeutically effective dose level for any particular patient will depend upon a variety of factors including the type and degree of the response to be achieved; the specific composition of another agent, if any, employed; the age, body weight, general health, sex and diet of the patient; the time of administration, route of administration, and rate of excretion of the composition; the duration of the treatment; drugs (such as a chemotherapeutic agent) used in combination or coincidental with the specific composition; and like factors well known in the medical arts. Suitable formulations, known in the art, can be found in Remington's Pharmaceutical Sciences (latest edition), Mack Publishing Company, Easton, Pa.

A composition to be used in a given preventative or therapeutic treatment will be formulated and dosed in a fashion consistent with good medical practice, taking into account the clinical condition of the individual patient (especially the side effects of prevention or treatment with the compounds alone), the site of delivery of the compound, the method of administration, the scheduling of administration, and other factors known to practitioners. The "effective amount" of the compounds of the invention for purposes herein is thus determined by such considerations.

Appropriate dosage of the compositions, e.g., vaccine compositions, of the invention to be administered to a patient will be determined by a clinician. However, as a guide, a suitable amount of a composition of the invention can be between about $10^1$ to $10^{12}$ CFU per dose, e.g., $10^1$, $10^2$, $10^3$, $10^4$, $10^5$, $10^6$, $10^7$, $10^8$, $10^9$, $10^{10}$, $10^{11}$, or $10^{12}$ CFU, suspended in 0.05 to 0.1 ml of an immunologically inert carrier, e.g., a pharmaceutical carrier. In one embodiment, an effective amount of a vaccine of the invention to induce immunity sufficient to prevent or treat, i.e., cure, ameliorate, lessen the severity of, or prevent or reduce a diseases described herein is about $10^3$ to about $10^7$ colony forming units (CFU)/kg body weight. A composition of the invention can be administered as a single dose or multiple doses. The vaccine formulations of the present invention can be employed in dosage forms such as capsules, liquid solutions, suspensions, or elixirs, for oral administration, or sterile liquid for formulations such as solutions or suspensions for, e.g., parenteral, intranasal or topical administration.

Compositions of the invention can be administered orally, intravenously, rectally, parenterally, intracisternally, intradermally, intravaginally, intraperitoneally, topically (as by powders, ointments, gels, creams, drops or transdermal patch), bucally, or as an oral or nasal spray. The term "parenteral" as used herein refers to modes of administration which include intravenous, intramuscular, intraperitoneal, intrasternal, subcutaneous and intraarticular injection and infusion.

Compositions, e.g., vaccine compositions, of the invention can be formulated according to known methods. Suitable preparation methods are described, for example, in *Remington's Pharmaceutical Sciences,* 16th Edition, A. Osol, ed., Mack Publishing Co., Easton, Pa. (1980), and *Remington's Pharmaceutical Sciences,* 19th Edition, A. R. Gennaro, ed., Mack Publishing Co., Easton, Pa. (1995), both of which are incorporated herein by reference in their entireties. Although the composition can be administered as an aqueous solution, it can also be formulated as an emulsion, gel, solution, suspension, lyophilized form, or any other form known in the art. In addition, the composition can contain pharmaceutically acceptable additives including, for example, diluents, binders, stabilizers, and preservatives. Once formulated, the compositions of the invention can be administered directly to the subject. The subjects to be treated can be animals; in particular, human subjects can be treated.

In certain embodiments, a host cell, e.g., a bacterial cell, having a vector expressing a polypeptide, e.g., an immunogenic polypeptide, of the present invention is incorporated in a composition. The concentration of polypeptides of the invention in the compositions of the invention can vary widely, i.e., from less than about 0.1%, usually at or at least about 2% to as much as 20% to 50% or more by weight, and will be selected primarily by fluid volumes, viscosities, etc., in accordance with the particular mode of administration selected.

Compositions of the invention ordinarily will be stored in unit or multi-dose containers, for example, sealed ampules or vials, as an aqueous solution or as a lyophilized formulation for reconstitution. Mycobacterial compositions with directly incorporated glycolipid adjuvant can be lypohilized and the adjuvant activity will be recovered intact when the composition is rehydrated and suspended for injection. As an example of a lyophilized formulation, 10-ml vials are filled with 5 ml of sterile-filtered 1% (w/v) aqueous solution, and the resulting mixture is lyophilized. An infusion solution is prepared by reconstituting the lyophilized composition using water, e.g., bacteriostatic Water-for-Injection.

Compositions of the invention are useful for administration to any animal, for example a mammal (such as apes, cows, horses, pigs, boars, sheep, rodents, goats, dogs, cats, chickens, monkeys, rabbits, ferrets, whales, and dolphins), and a human.

Animal models that have been shown to be good correlates for human disease include, but are not limited to guinea pigs and non-human primates (See e.g., Balasubramanian V et al., *Immunobiology* 191(4-5):395-401 (1994) and Barclay W R et al., *Infect. Immun.* 2(5):574-582 (1970), both incorporated herein by reference in their entirety).

The invention also provides a pharmaceutical pack or kit comprising one or more containers filled with one or more of the ingredients of the pharmaceutical compositions of the invention. Associated with such containers can be a notice in the form prescribed by a governmental agency regulating the manufacture, use or sale of pharmaceuticals or biological products, which notice reflects approval by the agency of manufacture, use or sale for human administration. In addition, the compositions of the present invention can be employed in conjunction with other therapeutic compositions.

Suitable preparations of such vaccines include, but are not limited to injectables, either as liquid solutions or suspensions; solid forms suitable for solution in, or suspension in liquid prior to injection, can also be prepared. The preparation can also be emulsified, or the polypeptides encapsulated in liposomes. The active immunogenic ingredients are often mixed with excipients which are pharmaceutically acceptable and compatible with the active ingredient. Suitable excipients are, for example, water, saline, dextrose, glycerol, or the like and combinations thereof. In addition, if desired, the vaccine preparation can also include minor amounts of auxiliary substances such as wetting or emulsifying agents, pH buffering agents, and/or adjuvants which enhance the effectiveness of the vaccine.

Compositions of the present invention which comprise a ceramide-like glycolipid/bacterial cell complex can further comprise additional adjuvants. Examples of adjuvants which can be effective are described above and can include, but are not limited to: aluminum hydroxide, N-acetyl-muramyl-L-threonyl-D-isoglutamine (thr-MDP), N-acetyl-nor-muramyl-L-alanyl-D-isoglutamine, N-acetylmuramyl-L-alanyl-D-isoglutaminyl-L-alanine-2-(1'-2'-dipalmitoyl-sn-glycero-3-hydroxyphosphoryloxy)-ethylamine, GM-CSF, QS-21 (investigational drug, Progenies Pharmaceuticals, Inc.), DETOX™ (investigational drug, Ribi Pharmaceuticals), BCG, and CpG rich oligonucleotides.

Compositions of the present invention which comprise a ceramide-like glycolipid/bacterial cell complex can further comprise additional adjuvants which are also Toll-like receptor (TLR) agonists. Examples of TLR agonist adjuvants which can be effective, include, but are not limited to: N-acetylmuramyl-L-alanine-D-isoglutamine (MDP), lipopolysaccharides (LPS), genetically modified and/or degraded LPS, alum, glucan, colony stimulating factors (e.g., EPO, GM-CSF, G-CSF, M-CSF, PEGylated G-CSF, SCF, IL-3, IL6, PIXY 321), interferons (e.g., γ-interferon, α-interferon), interleukins (e.g., IL-2, IL-7, IL-12, IL-15, IL-18), saponins (e.g., QS21), monophosphoryl lipid A (MPL), 3 De-O-acylated monophosphoryl lipid A (3D-MPL), unmethylated CpG sequences, 1-methyl tryptophan, arginase inhibitors, cyclophosphamide, antibodies that block immunosuppressive functions (e.g., anti-CTLA4 antibodies), lipids (such as palmitic acid residues), tripalmitoyl-S-glycerylcystein lyseryl-serine ($P_3$ CSS), and Freund's adjuvant. Other adjuvant examples include compounds such as isatoribin and it derivatives (Anadys Pharmaceuticals) or imidazoquinolinamines, such as imiquimod and resiquimod (Dockrell & Kinghom, *J. Antimicrob. Chemother.*, 48:751-755 (2001) and Hemmi et al., *Nat. Immunol.*, 3:196-200 (2002), guanine ribonucleosides, such as C8-substituted or N7, C-8-disubstituted guanine ribonucleosides (Lee et al., *Proc. Natl. Acad. Sci. USA*, 100:6646-6651 (2003) and the compounds that are disclosed in Pat. Pub. Nos. JP-2005-089,334; WO99/32122; WO98/01448 WO05/092893; and WO05/092892, and TLR-7 agonist SM360320 (9-benzyl-8-hydroxy-2-(2-methoxy-ethoxy)adenine) disclosed in Lee et al., *Proc Natl Acad Sci USA*, 103(6):1828-1833 (2006).

In addition to isatoribin, other TLR agonist adjuvants include 9-benzyl-8-hydroxy-2-(2-methoxyethoxy)adenine (SM360320), Actilon™ (Coley Pharmaceutical Group, Inc.), and the following compounds by Sumitmo Pharmaceutical Co, Ltd.:

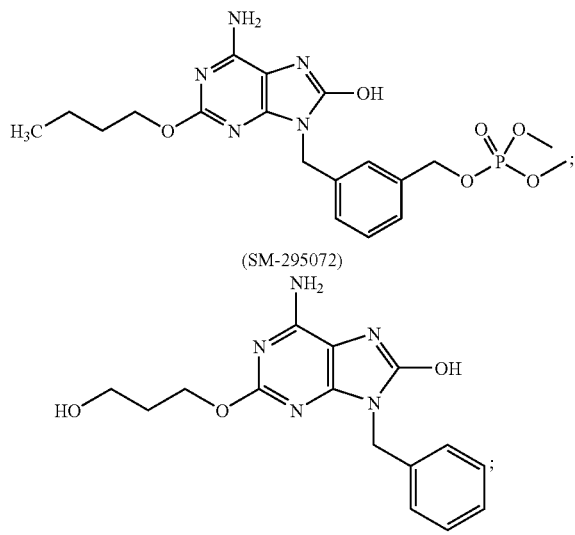

(SM-295072)

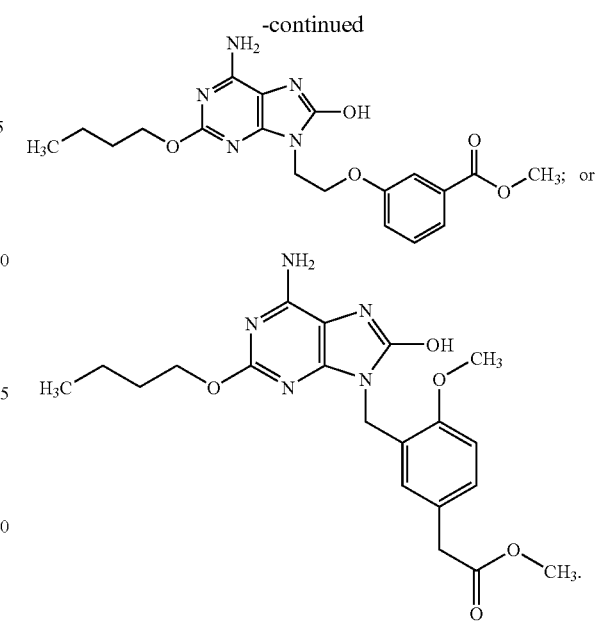

Other adjuvants which can be used in conjunction with the composition of the present invention are disclosed in PCT Pub. No. WO 2005/000348, U.S. Pat. Pub. No. 2007/0292418, and U.S. Pat. Pub. No. 2007/0287664.

The composition, if desired, can also contain minor amounts of wetting or emulsifying agents, or pH buffering agents. The composition can be a liquid solution, suspension, emulsion, tablet, pill, capsule, sustained release formulation, or powder. Oral formulation can include standard carriers such as pharmaceutical grades of mannitol, lactose, starch, magnesium stearate, sodium saccharine, cellulose, magnesium carbonate, etc.

The compositions of the present invention can further comprise other compounds which modulate an immune response, for example, cytokines. The term "cytokine" refers to polypeptides, including, but not limited to, interleukins (e.g., IL-1, IL-2, IL-3, IL-4, IL-5, IL-6, IL-7, IL-8, IL-9, IL-10, IL-11, IL-12, IL-13, IL-14, IL-15, IL-16, IL-17, and IL-18), a interferons (e.g., IFN-α), β interferon (IFN-β), γ interferons (e.g., IFN-γ), colony stimulating factors (CSFs, e.g., CSF-1, CSF-2, and CSF-3), granulocyte-macrophage colony stimulating factor (GMCSF), transforming growth factor (TGF, e.g., TGFα and TGFβ), and insulin-like growth factors (IGFs, e.g., IGF-I and IGF-II).

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2nd Ed., Sambrook et al., ed., Cold Spring Harbor Laboratory Press: (1989); Molecular Cloning: A Laboratory Manual, Sambrook et al., ed., Cold Springs Harbor Laboratory, New York (1992), DNA Cloning, D. N. Glover ed., Volumes I and II (1985); Oligonucleotide Synthesis, M. J. Gait ed., (1984); Mullis et al. U.S. Pat. No. 4,683,195; Nucleic Acid Hybridization, B. D. Hames & S. J. Higgins eds. (1984); Transcription And Translation, B. D. Hames & S. J. Higgins eds. (1984); Culture Of Animal Cells, R. I. Freshney, Alan R. Liss, Inc., (1987); Immobilized Cells And Enzymes, IRL Press, (1986); B. Perbal, A Practical Guide To Molecular Cloning (1984); the treatise, Methods In Enzymology, Academic Press, Inc., N.Y.; Gene Transfer Vectors For Mammalian Cells, J. H. Miller and M. P. Calos eds., Cold Spring Harbor Laboratory (1987); Methods In Enzymology, Vols. 154 and 155 (Wu et al. eds.); Immunochemical Methods In Cell And Molecular Biology, Mayer and Walker, eds., Academic Press, London (1987); Handbook Of Experimental Immunology, Volumes I-IV, D. M. Weir and C. C. Blackwell, eds., (1986); Manipulating the Mouse Embryo, Cold Spring Harbor Laboratory Press, Cold Spring Harbor, N.Y., (1986); and in Ausubel et al., Current Protocols in Molecular Biology, John Wiley and Sons, Baltimore, Md. (1989).

General principles of antibody engineering are set forth in Antibody Engineering, 2nd edition, C. A. K. Borrebaeck, Ed., Oxford Univ. Press (1995). General principles of protein engineering are set forth in Protein Engineering, A Practical Approach, Rickwood, D., et al., Eds., IRL Press at Oxford Univ. Press, Oxford, Eng. (1995). General principles of antibodies and antibody-hapten binding are set forth in: Nisonoff, A., Molecular Immunology, 2nd ed., Sinauer Associates, Sunderland, Mass. (1984); and Steward, M. W., Antibodies, Their Structure and Function, Chapman and Hall, New York, N.Y. (1984). Additionally, standard methods in immunology known in the art and not specifically described are generally followed as in Current Protocols in immunology, John Wiley & Sons, New York; Stites et al. (eds), Basic and Clinical-Immunology (8th ed.), Appleton & Lange, Norwalk, Conn. (1994) and Mishell and Shiigi (eds), Selected Methods in Cellular Immunology, W.H. Freeman and Co., New York (1980).

Standard reference works setting forth general principles of immunology include Current Protocols in Immunology, John Wiley & Sons, New York; Klein, J., Immunology: The Science of Self-Nonself Discrimination, John Wiley & Sons, New York (1982); Kennett, R., et al., eds., Monoclonal Antibodies, Hybridoma: A New Dimension in Biological Analyses, Plenum Press, New York (1980); Campbell, A., "Monoclonal Antibody Technology" in Burden, R., et al., eds., Laboratory Techniques in Biochemistry and Molecular Biology, Vol. 13, Elsevere, Amsterdam (1984), Kuby Immunnology 4th ed. Ed. Richard A. Goldsby, Thomas J. Kindt and Barbara A. Osborne, H. Freemand & Co. (2000); Roitt, I., Brostoff, J. and Male D., Immunology 6th ed. London: Mosby (2001); Abbas A., Abul, A. and Lichtman, A., Cellular and Molecular Immunology Ed. 5, Elsevier Health Sciences Division (2005); Kontermann and Dubel, Antibody Engineering, Springer Verlan (2001); Sambrook and Russell, Molecular Cloning: A Laboratory Manual. Cold Spring Harbor Press (2001); Lewin, Genes VIII, Prentice Hall (2003); Harlow and Lane, Antibodies: A Laboratory Manual, Cold Spring Harbor Press (1988); Dieffenbach and Dveksler, PCR Primer Cold Spring Harbor Press (2003).

All of the references cited above, as well as all references cited herein, are incorporated herein by reference in their entireties.

EXAMPLES

Materials and Methods

Mice.

Six (6) to 8 week old female wild-type C57BL/6 and BALB/c mice were obtained from Jackson Laboratories (Bar Harbor, Me.). CD1d$^{-/-}$ mice were provided by M. Exley and S. Balk (Beth IsraelDeaconess Medical Center, Harvard Medical School, Boston). V14i NKT cell-deficient Jα18$^{-/-}$ mice were a gift from M. Taniguchi and T. Nakayama (Chiba University, Chiba, Japan). All mice were housed in a biosafety level 3 facility under specific-pathogen-free conditions and used in a protocol approved by the institution.

Cells and Cell Lines.

Bone marrow derived dendritic cells (BMDC) from C57BL/6 and BALB/c mice were prepared based on a published protocol. Lutz M B, et al, *J Immunol Methods* 223: 77-92 (1999). Briefly, marrow cells were obtained from the femur and tibia and plated at $2 \times 10^6$ cells/plate in a bacteriological petri dish. The cells were incubated in GM-CSF culture medium for 10 days before harvesting the non-adherent dendritic cells, as described in Lutz et al. The Vα14i NKT hybridoma DN3A4-1.2 was provided by M. Kronenberg (La Jolla Institute for Allergy and Immunology, La Jolla, Calif.). Cells were cultured in RPMI-1640 medium (GIBCO) supplemented with 10% heat-inactivated FCS (Gemini Biological Products, Calabasas, Calif.), 10 mM HEPES, 2 mM L-glutamine, 0.1 mM nonessential amino acids, 55 μM 2-mercaptoethanol, 100 units/ml penicillin and 100 μg/ml streptomycin (GIBCO) in a 37° C. humidified incubator with 5% $CO_2$. Spleen cells were prepared by mashing with a syringe plunger and passing through a 70 μM cell strainer. Red blood cell lysis was carried out with red blood cell lysing buffer (SIGMA). Liver mononuclear cells were isolated using the following procedure. The liver was treated with 0.014 Wunsch units/ml of Liberase (Roche) for 30 minutes. The homogenate was passed through a 70 μM cell strainer, and the mononuclear cells were isolated from the pellet using a 45%, 67.5% Percoll gradient.

Glycolipids.

αGalCer was synthesized according to published methods (Yu, K. O. A. et al., Proc Natl. Acad. Sci. USA 102:3383 (2005)), and α-C-GalCer was obtained from the NIH Tetramer Core Facility (www.niaid.nih.gov/reposit/tetramer/genguide.html). Glycolipids were stored dry at −20° C. Aliquots from the stock were reconstituted to either 100 μM in DMSO for in vitro work or to 500 μM in 0.5% Tween-20 in PBS for in vivo studies.

Bacterial Strains.

*M. bovis* BCG (Danish) was obtained from Statens Serum Institute, Denmark and the recombinant BCG-Ova (Pasteur strain) was a kind gift from Subash Sad, National Research Council-Institute for Biological Sciences, Ottawa, Ontario, Canada (See Dudani R et al., *J. Immunol.* 168(11): 5737-45 (2002)). These strains were grown in protein-free Middlebrook 7H9 medium (Difco) with 0.05% tyloxapol and 20 μg/ml of either αGalCer or α-C-GalCer. Virulent *M. tuberculosis* strain H37Rv (obtained from Trudeau Institute), was grown in Middlebrook 7H9 medium supplemented with the oleic acid-albumin-dextrose complex (Difco).

Incorporation of $^{14}$C-Labeled αGalCer into Live BCG.

*M. bovis* BCG was grown in protein-free Middlebrook 7H9 medium containing 0.05% tyloxapol and 20 μg/ml of $^{14}$C-labeled αGalCer to OD of 0.5 to 1.0. The bacteria were washed thoroughly, dried and lipid incorporation was assessed by β-scintillation counting. The dried bacteria were used for cell wall lipid extraction which was used for the TLC assay.

In Vitro Activity of αGalCer and α-C-GalCer Incorporated into BCG (αGalCer-BCG and α-C-GalCer-BCG, Respectively).

For NKT hybridoma assay, BMDC were infected with BCG, αGalCer-BCG or α-C-GalCer-BCG at an MOI of 10:1 and Vα14i NKT hybridoma cells (50,000 cells) were added for 12 h. Supernatant IL-2 was assayed by ELISA. For splenocyte or hepatic cell stimulations, bulk splenocytes were plated at 500,000 cells or liver mononuclear cells were plated at 400,000 cells per well in 96-well flat-bottom tissue culture plates with C57BL/6 BMDCs infected with BCG, αGalCer-BCG or α-C-GalCer-BCG. For splenocyte activation, the infected BMDCs were used at cell numbers starting from 25,000 cells/well diluted 4-fold up to 3,125 cells/well. The hepatic cells were stimulated with $10^5$ infected BMDCs per well. After 48 h at 37° C., 150 µl of supernatant was removed for cytokine measurements. Supernatant levels of IL-4 and IFNγ were measured by ELISA using capture and biotinylated detection antibody pairs (BD PharMingen) and streptavidin-horseradish peroxidase (Zymed) with TMB-Turbo substrate (Pierce).

Human NKT Cell Clone Activation.

Human monocyte-derived dendritic cells were infected at an MOI of 5:1, incubated with a NKT cell clone (50,000 cells) for 24 hours and supernatant was assayed for IFNγ and IL-13.

In Vivo Activity αGalCer Incorporated into BCG.

Mice were given intraperitoneal (i.p.) injections of αGalCer-BCG in 0.2 ml of PBS plus 0.05% Tyloxapol or vehicle alone. Sera were collected and tested for IL-4, IL-12p70, and IFNγ by capture ELISA as described in Yu K O et al, *Proc Natl Aced Sci USA* 102: 3383-3388 (2005).

In Vivo Dendritic Cell Maturation Assay Following Intraperitoneal Injection of αGalCer-BCG.

C57BL/6 mice or $CD1d^{-/-}$ mice were i.p. injected with αGalCer-BCG, splenocytes and hepatic mononuclear cells were harvested 20 h and 40 h later. The cells were stained with fluorochrome-labeled antibodies to CD11c, CD80, CD86, MHC-II (IA/IE), CD70, 41BB and OX40. The samples were analyzed on a LSR II flow cytometer.

T Cell IFN-γ ELISPOT Assay.

ELISPOT was used to detect IFNγ secretion by individual $CD8^+$ T cells from infected mice after stimulation with OVA 257-264 peptide (SIINFEKL (SEQ ID NO: 1)), the TB10.3/4 MHC-I ($H-2K^d$) restricted peptide (GYAGTLQSL (SEQ ID NO: 2)) or the TB10.3/4 MHC-I ($H-2K^b$) restricted peptide (QIMYNPAM (SEQ ID NO: 3)) in vitro. ELISPOT plates (Millipore) were coated with IFNγ capture antibody (BD Biosciences) for 16 hours at room temperature (RT). Plates were washed and blocked with 1% BSA for 2 hours at RT. After treatment with RBC lysis buffer (Sigma-Aldrich), T cells were separated using the Dynal Mouse T Cell Negative Isolation Kit (Invitrogen). The separated T cells were cultured with splenocytes from a naïve mouse and the peptides (5 µg/ml) for 24 hours at 37° C. After cells were removed, plates were washed with PBS followed by PBS with 0.05% Tween-20 (PBST). Biotinylated anti-IFNγ detection antibody (BD Biosciences) was added for 2 hours at 37° C., followed by washing with PBST. Streptavidin-alkaline phosphatase (Sigma-Aldrich) was added to the plates for 1 hour (37° C.), followed by washing and addition of BCIP/NBT substrate (Sigma-Aldrich). The reaction was stopped by washing the wells with water and spots were counted using an ELISPOT reader (Autoimmun Diagnostika). $CD4^+$ T cell responses were also evaluated to peptide-25 (FQDAYNAAGGHNAVF (SEQ ID NO: 4)) (5 ug/ml) amino acids 240 to 254 of *M. tuberculosis* Ag85B.

In Vivo Antigen Presentation Assay.

Donor splenocytes were isolated from Rag1 deficient OT-1 TCR-transgenic mice (Taconic/National Institute of Allergy and Infectious Diseases [NIAID]). After RBC lysis, cells were labeled with 10 µM carboxyfluorescein succinimidyl ester (CFSE) for 5 minutes at RT at a concentration of $5 \times 10^7$ cells/ml in PBS plus 0.1% BSA. Cells were washed once with PBS plus 0.1% BSA and twice with PBS before injection into B6.PL ($Thy1.1^+$) recipient mice (The Jackson Laboratory). Mice received either $5 \times 10^6$ or $1 \times 10^7$ labeled cells via the lateral tail vein and were then vaccinated subcutaneously with $5 \times 10^6$ CFU of BCG-OVA/αGalCer, BCG-OVA or BCG. Splenocytes were harvested 5-7 days later, stained with anti-Thy1.2, anti-CD8 and anti-B220 antibodies (BD Biosciences), and analyzed by flow cytometry. Expansion was quantified by gating on the transferred population ($Thy1.2^+$) and measuring the percentage of undivided ($CFSE^{high}$) cells within this population.

Vaccination and Challenge Studies.

All animal studies were approved by the institutional animal care and use committees of the Albert Einstein College of Medicine. C57BL/6 mice were vaccinated intradermally with either BCG alone or the BCG grown with one of the glycolipids ($5 \times 10^6$ CFU/mouse). Aerogenic challenge was done 2 months later using a Glas-Col inhalation chamber to deliver 50-100 CFU per animal of virulent strain *M. tuberculosis* H37Rv. Mice were sacrificed at 3 and 6 weeks after challenge. Lungs and spleens of individual mice were aseptically removed and homogenized separately in 5 ml normal saline plus 0.05% Tween-80 using a Seward Stomacher 80 blender (Tekmar). The homogenates were diluted serially and plated on Middlebrook 7H10 agar with hygromycin (50 µg/ml). Lung tissues were processed for histopathology using standard paraffin fixation, sectioning and H&E staining.

Example 1

Stable Incorporation of αGalCer into the Cell Wall of Live Mycobacteria

This Example demonstrates the stable incorporation of an exemplary ceramide-like glycolipid, αGalCer, into the cell wall of a mycobacterium. The mycobacterial cell, *M. bovis* BCG, is a live attenuated bacterial vaccine which is actively ingested by APCs and processed for antigen presentation. The solubility of $^{14}C$-labeled αGalCer in (1) polysorbate Tween-80 (0.05%) and (2) tyloxapol (0.05%) was tested. Solubility with tyloxapol for $^{14}$-labeled αGalCer was greater than the solubility in tween-80 (FIG. 1A). BCG cells were grown in the presence of $^{14}C$-labeled αGalCer with tyloxapol (0.05%) in protein-free Middlebrook 7H9 medium. The cells were then washed thoroughly with PBS-tyloxapol (0.05%) and scintillation counts showed that the radio-labeled αGalCer was associated with the BCG cell wall (FIG. 1B).

Cell wall lipids were extracted from BCG grown in presence of $^{14}C$-labeled αGalCer, and subjected to thin-layer chromatography. The radio-labeled lipid from the lipid extract had mobility similar to that of the free $^{14}C$-labeled αGalCer showing that this ceramide-like glycolipid was stably bound to the cell wall and was chemically intact (FIG. 1C). Quantitation of the TLC bands showed that about 21.4% of the radio-labeled ceramide-like glycolipid was incorporated into the bacterial cell wall. Thus, a ceramide-like glycolipid, αGalCer, was stably incorporated into a mycobacterial cell wall allowing for simultaneous administration of both the glycolipid adjuvant and the BCG vaccine.

Figure 2:
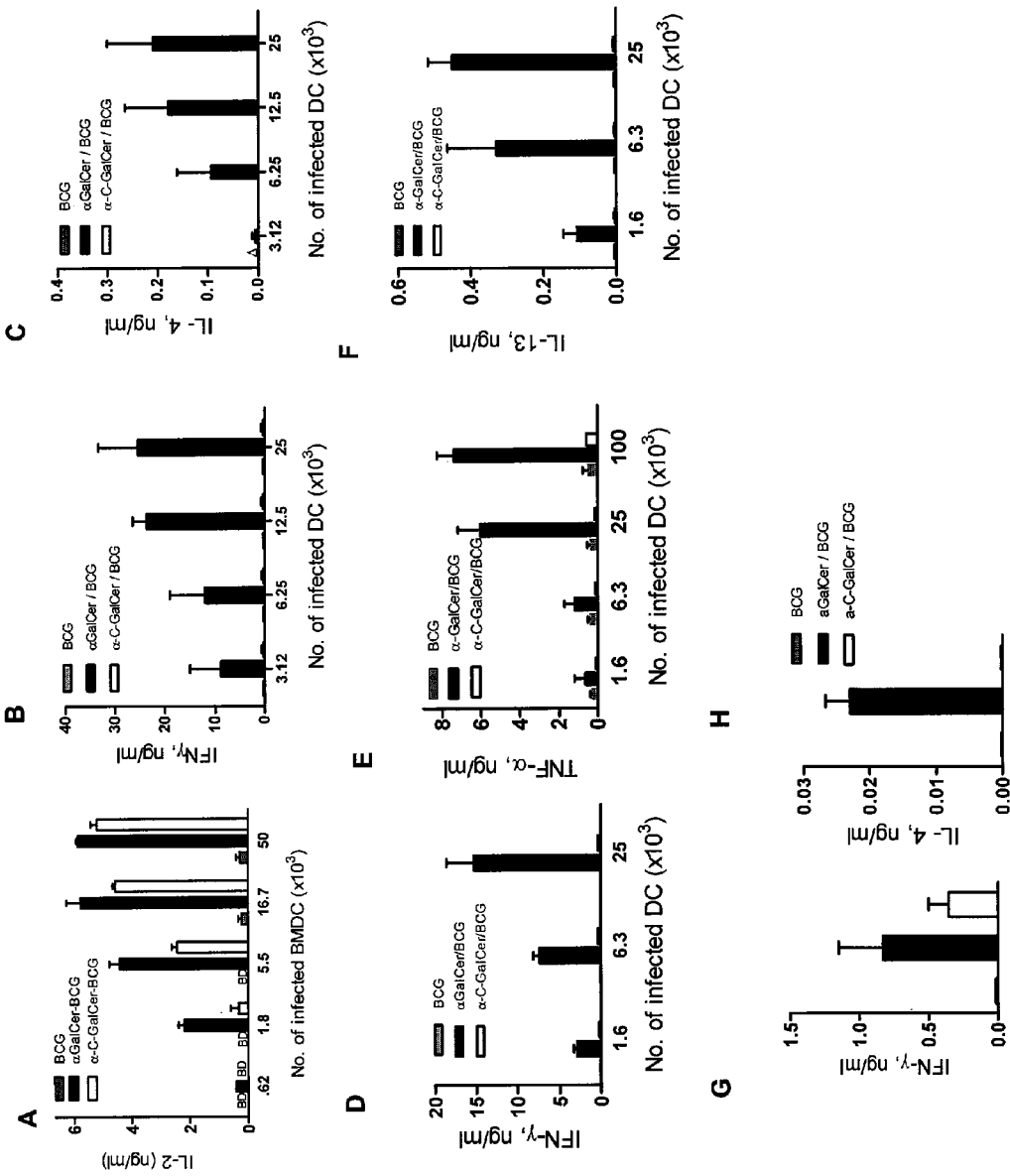
FIG. 2: αGalCer bound to *M. bovis* BCG is biologically active in vitro. (A) Dose-response curves showing 24 h IL-2 production upon activation of NKT cell hybridoma DN3A4-1.2 when incubated with bone marrow derived dendritic cells (BMDC) infected with BCG, αGalCer/BCG or α-C-GalCer/BCG. (B) and (C) Dose response curves showing 24 hour (B) IFNγ and (C) IL-4 production upon activation of mouse splenocytes with BCG, αGalCer/BCG or α-C-GalCer/BCG infected BMDC. (D), (E) and (F) Dose-response curves showing (D) IFNγ, (E) TNFα, and (F) IL-13 production upon activation of a human iNKT cell clone with monocyte-derived human dendritic cells infected with BCG, αGalCer/BCG or α-C-GalCer/BCG. (G) and (H) Dose-response curves showing (G) IFNγ and (H) IL-4 production upon activation of hepatic mononuclear cells from a naïve C57BL/6 mouse when incubated with BCG, αGalCer/BCG or α-C-GalCer/BCG infected BMDC.

Example 2

αGalCer or α-C-GalCer Bound to the BCG Cell Wall are Biologically Active In Vitro in Mouse and Human Assays This Example demonstrates that a ceramide-like glycolipid incorporated to a mycobacterial cell wall (a ceramide-like glycolipid/mycobacterial complex) is biologically active. αGalCer and its analogues are known to activate NKT cells in vitro. This biological activity was tested to determine whether ceramide-like glycolipids incorporated into a mycobacterial cell wall retained the ability to activate NKT cells in vitro. Mouse BMDC infected with α-GalCer-BCG or α-C-GalCer-BCG were incubated with an NKT cell hybridoma. IL-2 was easily detectable in the supernatant in a dose-dependant manner indicating very efficient activation of NKT cells in vitro by each of the ceramide-like glycolipids which were bound to the BCG cell wall (FIG. 2A). All FIG. 2 values are shown as means of triplicate cultures.

Activation of mouse splenocytes with αGalCer-BCG infected BMDCs induced IFNγ and IL-4 production, as shown in FIG. 2B and FIG. 2C. Hepatic mononuclear cell stimulation with αGalCer-BCG infected BMDCs induced IFNγ and IL-4 (FIGS. 2G and 2H, respectively) whereas α-C-GalCer-BCG infected BMDC induced IFNγ but no detectable IL-4 from hepatic mononuclear cells (FIGS. 2G and 2H). Activity of α-GalCer-BCG or α-C-GalCer-BCG was also tested in a human system by stimulating a NKT cell clone with infected monocyte-derived human dendritic cells. The α-GalCer-BCG complex strongly induced IFNγ, TNFα and IL-13 in a dose dependent manner indicating that the strategy of incorporating a ceramide-like glycolipid adjuvant into the cell wall of vaccine cells can be applicable to humans (FIGS. 2D, 2E and 2F, respectively).

The ability of the αGalCer-BCG infected human monocyte-derived dendritic cells to activate an human NKT cell clone shows that this vaccine strategy applicable to vaccination of humans against tuberculosis.

Example 3

αGalCer-BCG Induces a Detectable Cytokine Response In Vivo

Figure 3:
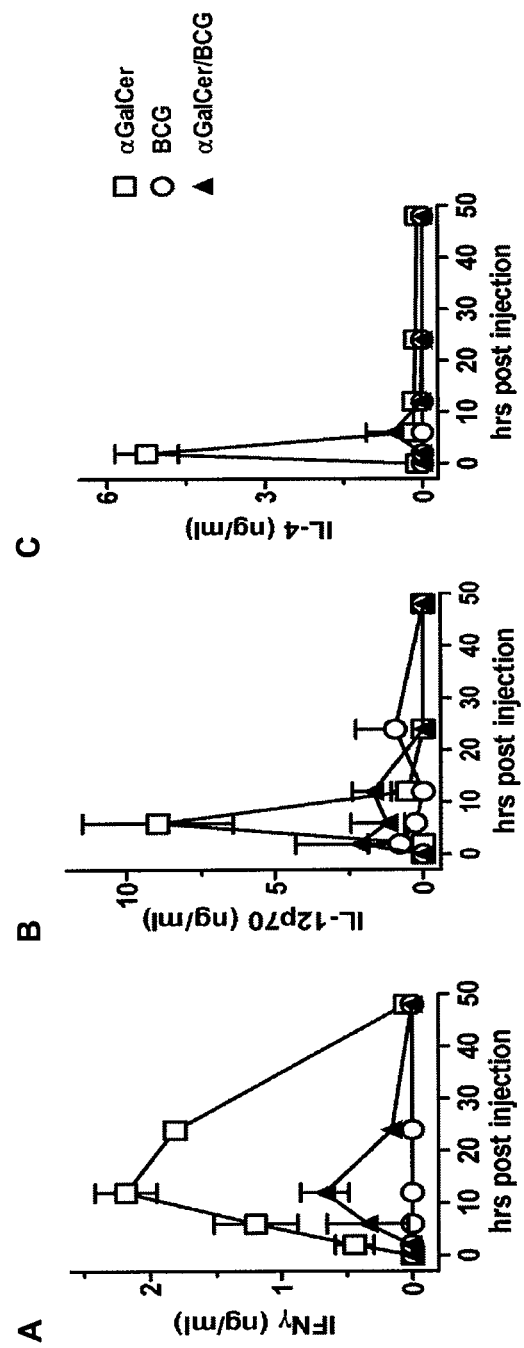
FIG. 3: αGalCer bound to *M. bovis* BCG is biologically active in vivo. (A), (B), and (C) Graphs showing the serum levels (ng/ml) of (A) IFN-γ, (B) IL-12p70, and (C) IL-4 at various time points 1 to 50 hours post-injection in mice given 4.8 nmol of vehicle (Veh), BCG, αGalCer or αGalCer/BCG ($5\times10^6$ CFU).

This example demonstrates that a ceramide-like glycolipid/mycobacterial complex retains in vivo activity. Administration of αGalCer to mice induces a serum cytokine response. The in vivo activity of BCG cells bound to ceramide-like glycolipids was tested. αGalCer-BCG cells (5×10$^6$) were injected intraperitoneally into C57BL/6 mice, and the serum was examined for cytokines at various time points. αGalCer/BCG complexes induced significant serum levels of IFNγ, IL-12 and IL-4 (FIGS. 3A, 3B and 3C), with kinetics that were similar to those seen with free glycolipid. Thus, αGalCer/BCG complexes were shown to be active in vivo. The serum cytokines were not detected in CD1d KO or Jα18 KO mice (both NKT deficient) which were injected with αGalCer/BCG (data not shown), showing that the cytokine induction by the αGalCer/BCG complex is through association with CD1d and involves NKT cell activation.

Figure 4:
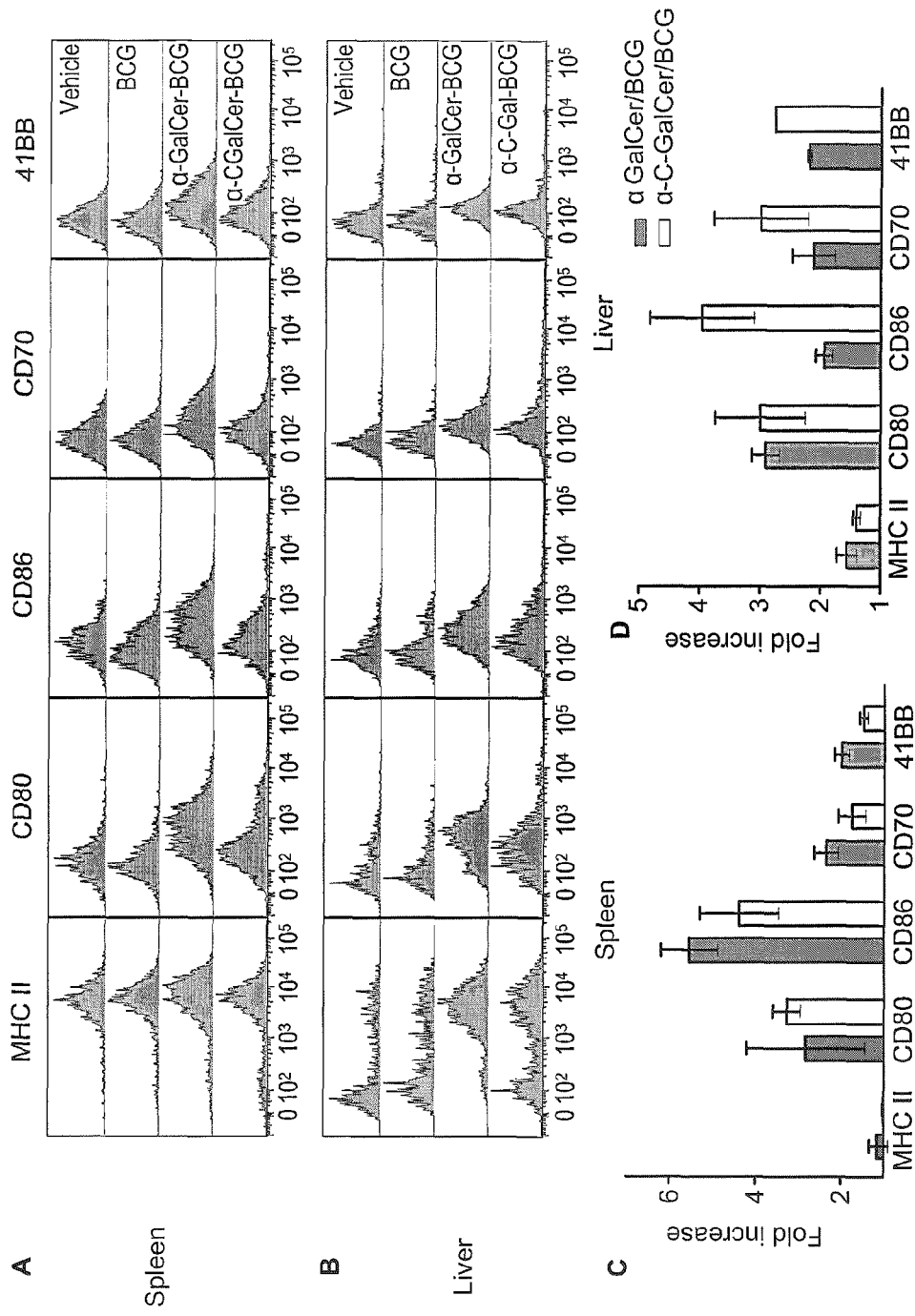
FIG. 4: αGalCer and α-C-GalCer induce rapid upregulation of DC maturation and co-stimulatory markers when co-administered with *M. bovis* BCG. (A) and (B) Histogram profiles for DC maturation markers 20 hours after IP injection of Vehicle, BCG, αGalCer/BCG and α-C-GalCer/BCG on (A) splenic and (B) liver CD11c+ Dendritic cells. Upregulation of MHC II and co-stimulatory molecules: CD80, CD86, CD70, and 41BB. (C) and (D) Graphs showing fold increase of MHC II, CD80, CD86, CD70, and 41BB levels in (C) spleen and (D) liver cells are shown for αGalCer/BCG and α-C-GalCer/BCG.

Example 4

α-GalCer Actively Induces Costimulatory Molecules on Dendritic Cells In Vivo This example demonstrates that ceramide-like glycolipid/mycobacterium complexes retain the ability to induce expression of costimulatory molecules on CD11c$^+$ dendritic cells (DCs). It is known that αGalCer and α-C-GalCer alone can induce expression of costimulatory molecules on CD11c$^+$ dendritic cells. C57BL/6 mice were i.p injected with αGalCer-BCG or α-C-GalCer-BCG. Expression levels of MHC-II and costimulatory molecules on the CD11c$^+$ DCs in spleens and livers were tested. Both ceramide-like glycolipid/mycobacteria complexes induced up-regulation of the co-stimulatory molecules CD80, CD86, CD70 and 4-1BB in spleen and liver relative to BCG alone (FIGS. 4A and 4B). Fold increase with MHC-II and co-stimulatory molecules is shown in FIGS. 4C and 4D. The incorporated α-C-GalCer adjuvant induced a more pronounced upregulation of CD86, CD70 and 41BB molecules in the liver (FIG. 4D). The MHC II upregulation was similar to that induced by BCG in the spleen or the liver. It was also verified that these effects depended on invariant NKT cell activation by testing mice genetically lacking CD1d (data not shown).

These results show that the biological activity of the ceramide-like glycolipids is intact after incorporation into the BCG cell wall. In particular, αGalCer-BCG and α-C-GalCer-BCG induce full maturation of DCs, as determined by an increased expression of co-stimulatory molecules, which include CD80 and CD86, as well as MHC class II molecules on DCs. The upregulation of maturation and co-stimulatory markers was delayed in mice given the BCG vaccine alone compared to the ceramide-like glycolipid-complexed BCG, which likely contributes to improved T cell responses against mycobacterial antigens. Thus, mice injected with ceramide-like glycolipid-incorporated BCG cells had an improved vaccine affect as compared to BCG cells alone.

Example 5

Figure 5:
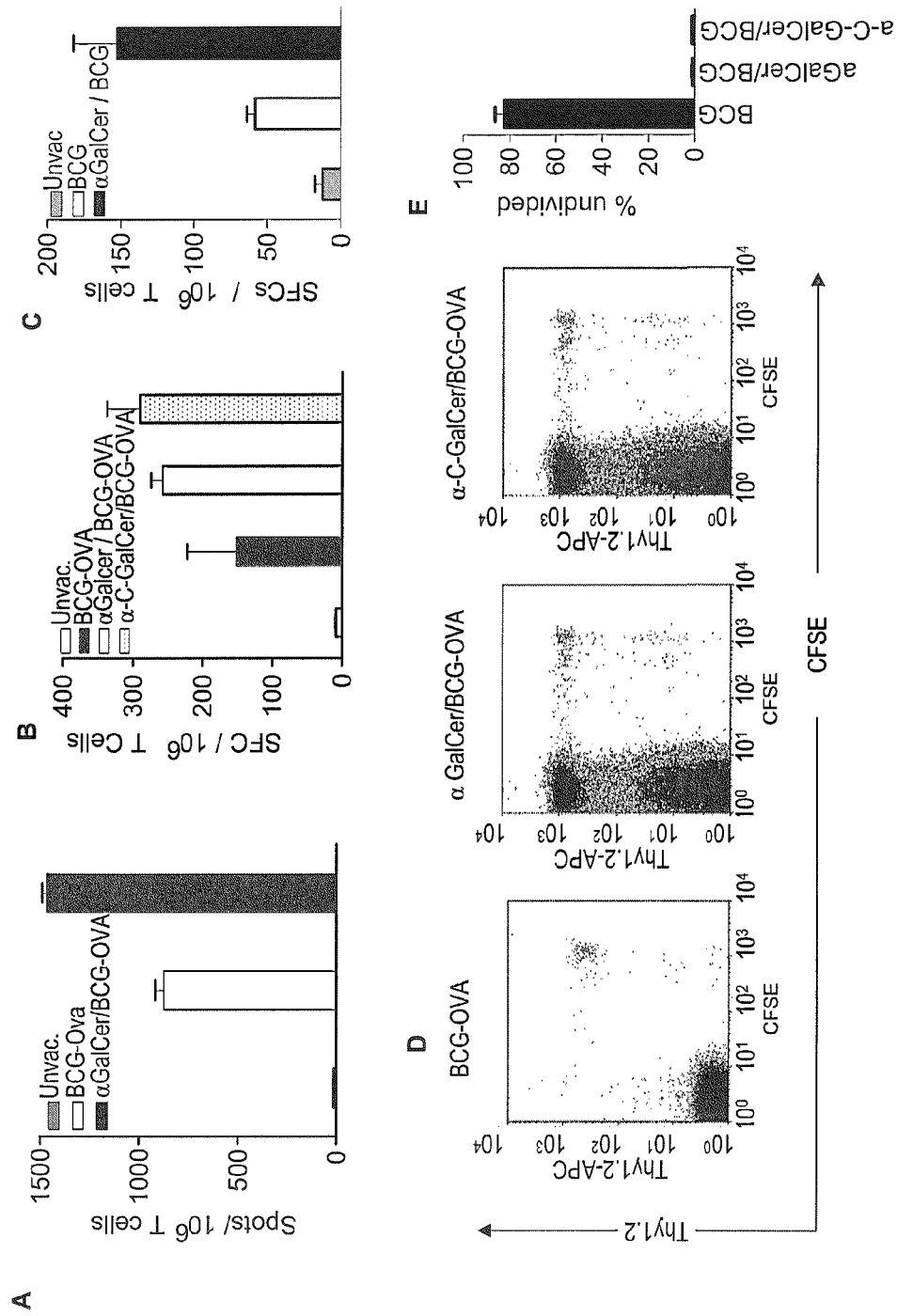
FIG. 5: Vaccination with BCG-OVA and αGalCer as adjuvant enhances CD8 T cell responses to mycobacterial antigens. (A) Graph showing results from an ELISPOT Assay for IFNγ producing CD8 T cells specific to the OVA peptide, SIINFEKL (SEQ ID NO: 1), at 3 weeks in spleen of mice following immunization with αGalCer/BCG-Ova, BCG-Ova, or unvaccincated (Unvac.). (B) Graph showing results from ELISPOT Assay for IFNγ producing CD8 T cells specific to SIINFEKL at 2 months in spleen of mice following immunization with αGalCer/BCG-Ova, α-C-GalCer/BCG-Ova, BCG-Ova, or unvaccinated. (C) Graph showing results from ELISPOT Assay for IFNγ producing CD8 T cells specific to the Mtb peptide, TB10.3/4 MHC-I (H-2K$^d$) epitope GYAGTLQSL (SEQ ID NO: 2), at 2 weeks in BALB/c mice following immunization with αGalCer/BCG, BCG alone, or unvaccinated. (D) Dot plots showing representative Thy1.1$^+$ B6.PL mice injected with CFSE-labeled Thy1.2$^+$ OT-I splenocytes, and infected with αGalCer/BCG-Ova, α-C-GalCer/BCG-Ova, or BCG-Ova. (E) Graph showing percent undivided cells for cells described in (D).
Figure 6:
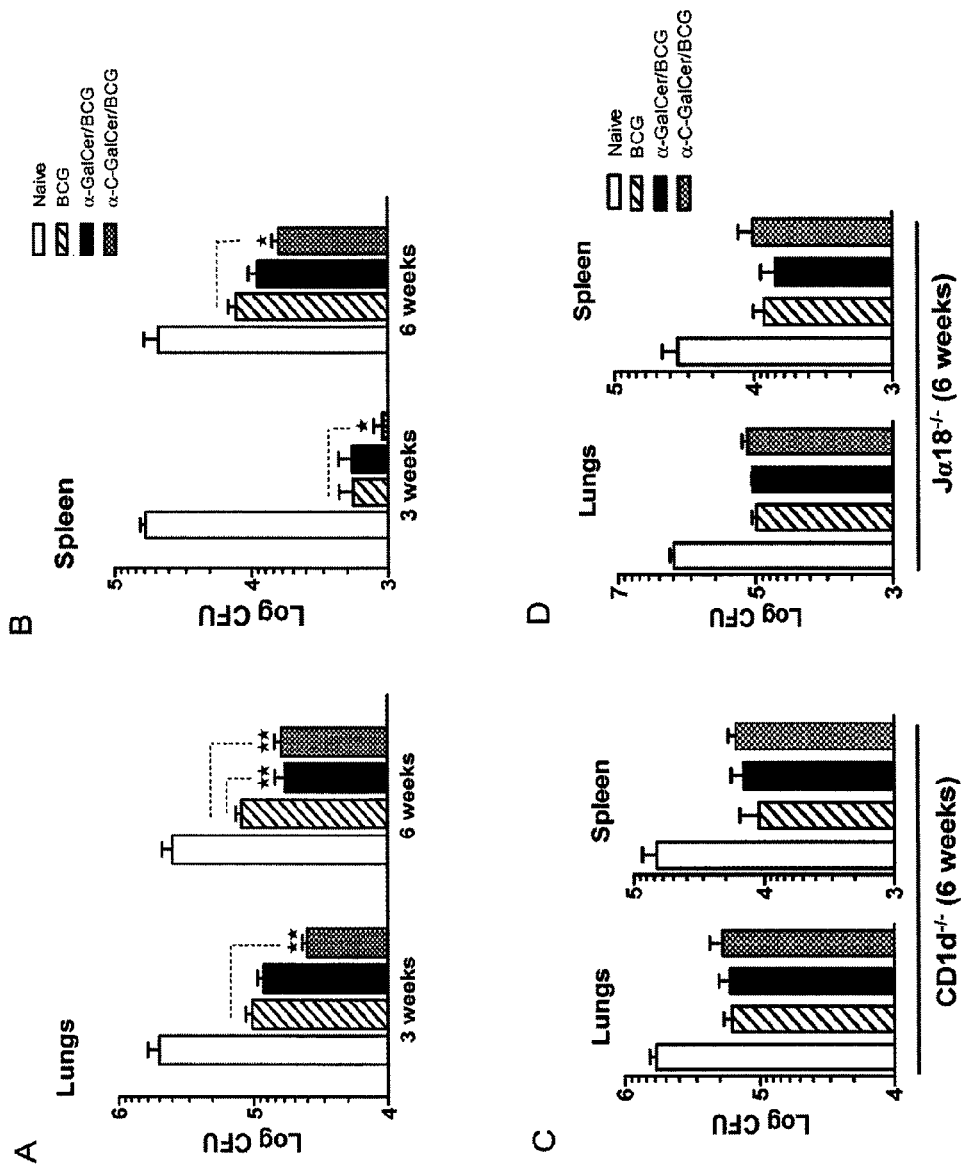
FIG. 6: Protective immunity against virulent *M. tuberculosis* challenge in mice following vaccination with BCG, αGalCer/BCG or α-C-GalCer/BCG. (A) and (B) Graphs showing mean CFU (and standard deviation) of *M. tuberculosis* in lung (A) and spleen (B) of C57BL/6 mice at 3 and 6 weeks after challenge with virulent *M. tuberculosis* H37Rv strain for groups of 7 mice that were either naïve (Unvac.) or vaccinated (BCG, αGalCer/BCG or α-C-GalCer/BCG). (C) Graph showing mean CFU of *M. tuberculosis* in lung and spleen of CD1d-KO mice at 6 weeks after challenge with virulent *M. tuberculosis* H37Rv strain for groups of 4 mice that were either naïve (Unvac.) or vaccinated (BCG, αGalCer/BCG or α-C-GalCer/BCG). (D) Graph showing mean CFU of *M. tuberculosis* in lung and spleen of Jalpha-18KO mice at 6 weeks after challenge for groups of 4 mice that were either naïve (Unvac.) or vaccinated (BCG, αGalCer/BCG or α-C-GalCer/BCG. *$p<0.05$; **$p<0.007$ (one way ANOVA, Turkey post-hoc test).
Figure 7:
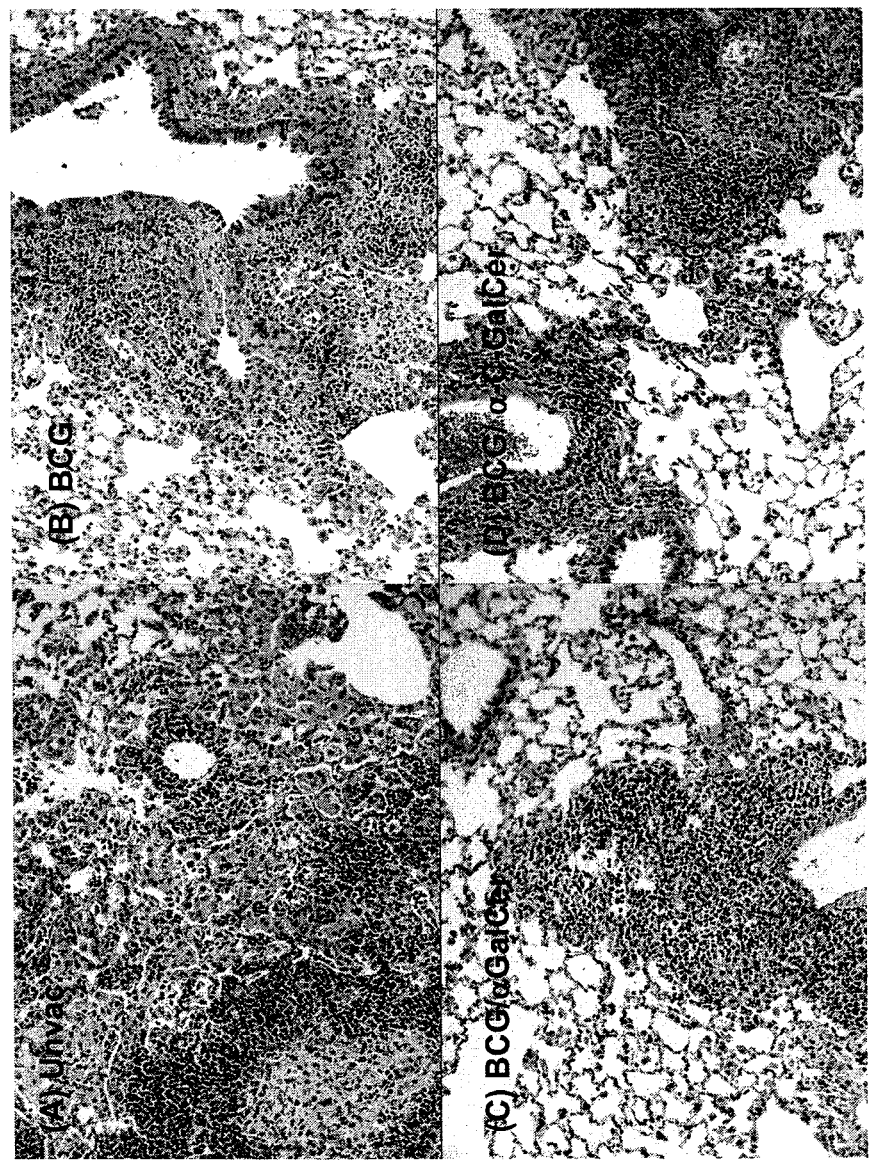
FIG. 7: Lungs of mice vaccinated and challenged with virulent *M. tuberculosis* were examined histologically at 6 weeks after challenge. (A) Image of more severe, spreading lung lesions with extensive granulomatous pneumonia and consolidation in unvaccinated mice as compared with mice vaccinated with either (B)BCG, (C)αGalCer/BCG, or (D) α-C-GalCer/BCG. Original magnification, 20×.
Figure 8:
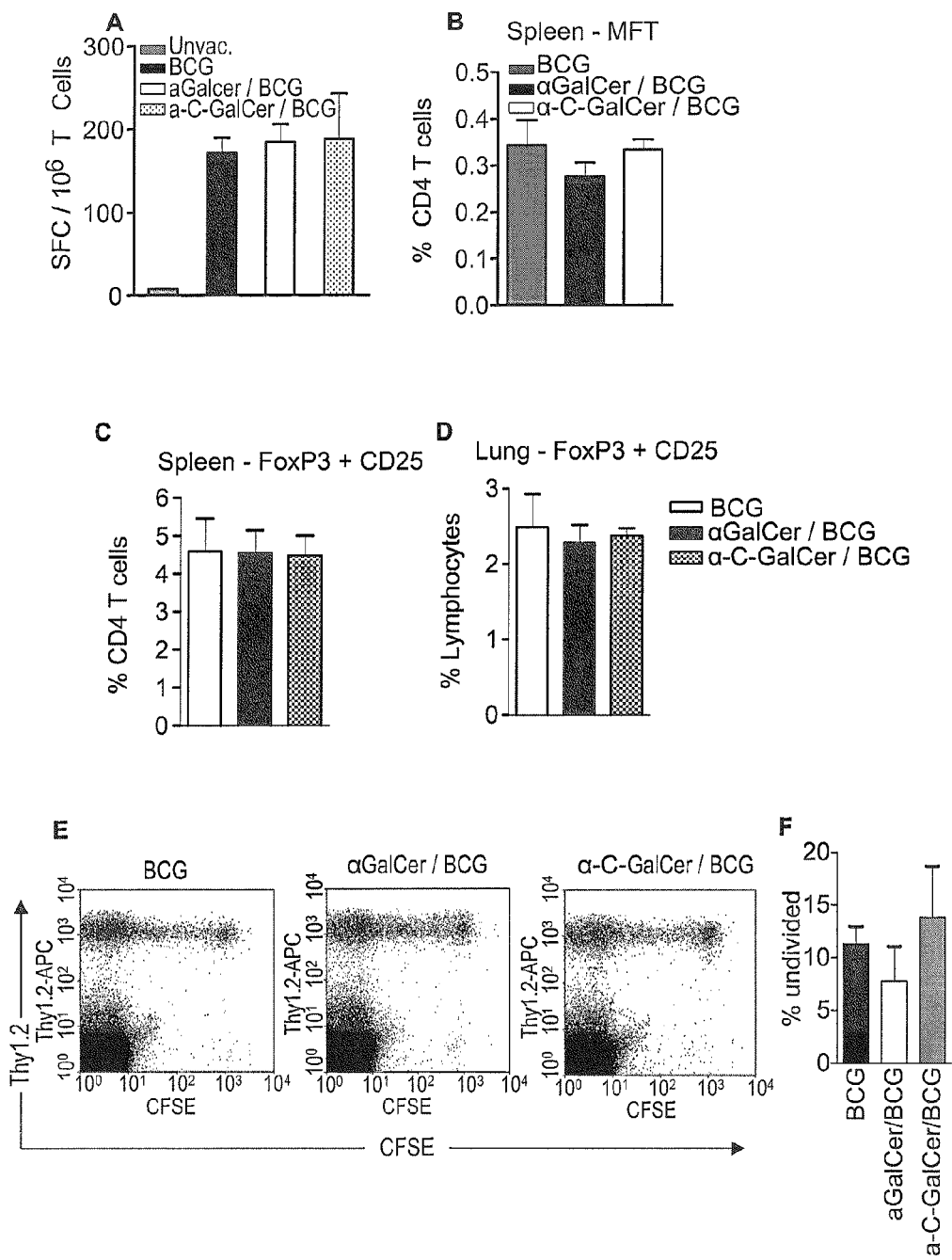
FIG. 8: Vaccination with αGalCer/BCG or α-C-GalCer/BCG does not siginifically enhance CD4 T cell responses to mycobacterial antigens compared to BCG. (A) Graph showing ELISPOT assay for IFN-γ producing splenic CD4 T cells specific to p25 of Ag85B at 2 months in C57BL/6 mice following immunization with BCG, αGalCer/BCG, α-C-GalCer/BCG, or unvaccinated. (B) Graph showing frequency of multifunctional CD4 T cells producing IFNγ, IL-2 and TNFα in spleen at 2 months following immunization with BCG, αGalCer/BCG or α-C-GalCer/BCG. (C) and (D) Graphs showing frequency of regulatory T cells in (C) spleen and (D) lung in C57BL/6 mice at 2 months following vaccination with BCG, αGalCer/BCG or α-C-GalCer/BCG. (E) Dot plots show representative Thy1.1$^+$ B6.PL mice injected with CFSE-labeled Thy1.2$^+$ P25TCR-Tg splenocytes, and infected with the BCG, αGalCer/BCG or α-C-GalCer/BCG. (F) Graph showing percent undivided cells for cells described in (E).

Enhancement of Antigen-Specific CD8 T Cell Priming by Simultaneous Administration of Ceramide-Like Glycolipid Adjuvants This example demonstrates that mycobacteria with αGalCer and α-C-GalCer stably incorporated into their cell walls exhibit improved CD8 T cell responses to mycobacterial antigens expressed by BCG. C57BL/6 mice were vaccinated with α-GalCer complexed with BCG-OVA or α-C-GalCer complexed with BCG-OVA and analyzed for SIINFEKL (SEQ ID NO: 1) OVA peptide responsive CD8 T cells in the spleen by IFNγ ELISPOT. Significantly enhanced priming of SIINFEKL-specific CD8 T cells was observed in mice administered the glycolipids complexed with the BCG-OVA vaccine as compared to mice that were vaccinated with the BCG-OVA alone for either 3 weeks or 2 months (FIGS. 5A and 5B, respectively). The adjuvant effect of αGalCer complexed with BCG to enhance CD8 T cell priming to the MHC-I epitope GYAGTLQSL (SEQ ID NO: 2) of the endogenous mycobacterial antigen TB10.4 was analyzed in vaccinated BALB/c mice by IFNγ ELISPOT. CD8$^+$ T cell activation was assessed 5-7 days after infection by carboxyfluorescein succinimidyl ester (CFSE) dilution. Mice that were administered the αGalCer-complexed BCG vaccine showed increased GYAGTLQSL (SEQ ID NO: 2) specific CD8 T cell response relative to unvaccinated or vaccinated with BCG alone (FIG. 5C). These results demonstrate that mycobacterial antigen-specific CD8 T cell responses are enhanced by activating NKT cells during immunization with a ceramide-like glycolipid and BCG-OVA.

Adoptive transfer of CFSE-labeled naive T cells from SIINFEKL/H-2K$^b$-reactive TCR-transgenic OT-I mice was used to show the priming of MHC class I-restricted CD8$^+$ T cells reactive with SIINFEKL in the context of vaccination. Hinchey J, et al., *J Clin Invest* 117: 2279-2288 (2007). Thy1.1$^+$ B6.PL mice were injected with CFSE-labeled Thy1.2$^+$ splenocytes from OT-I mice, followed by vaccination either with BCG-OVA alone, αGalCer/BCG-OVA complex or α-C-GalCer/BCG-OVA complex. CD8$^+$ T cell activation and proliferation were assessed by dilution of CFSE in the transferred population at 5-7 days after infection (FIG. 5D). Partial proliferation of transferred OT-I T cells was observed in mice infected with BCG-OVA (shown as a percentage of undivided cells). In contrast, αGalCer/BCG-OVA or α-C-GalCer/BCG-OVA infection induced a significant increase in proliferation of transferred T cells (FIG. 5E).

Example 6

Figure 9:
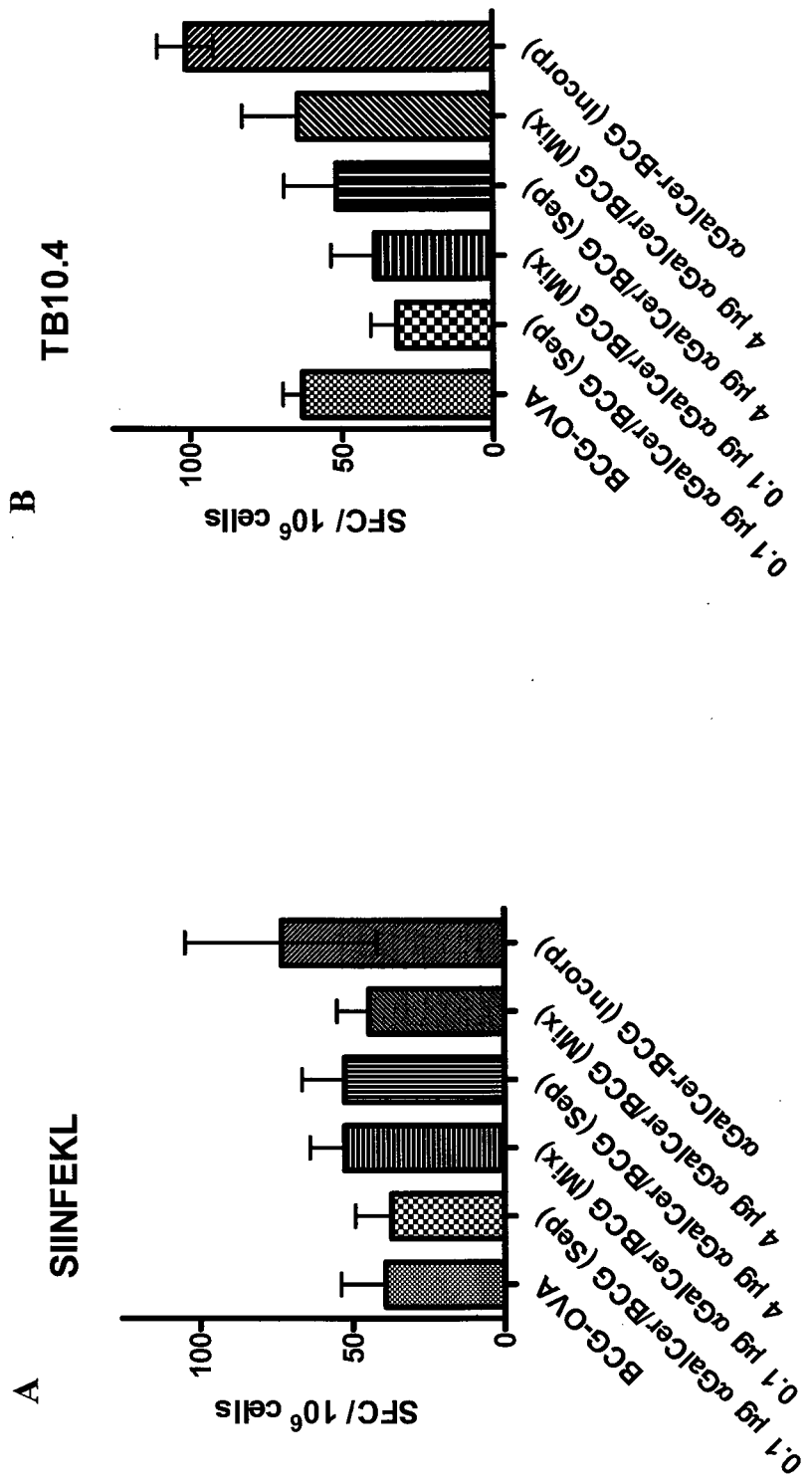
FIG. 9: Vaccination with αGalCer incorporated into BCG (Incorp) enhances CD8 T cell responses to mycobacterial antigens compared to separate administration (Sep=BCG-OVA and αGalCer injected separately at different sites) or mixing (Mix=BCG-OVA and αGalCer mixed together in the same syringe immediately before injection). (A) and (B) Graphs showing results from ELISPOT Assay for IFNγ producing CD8 T cells specific to (A) STINFEKL (SEQ ID NO: 1) or (B) TB10.4 MHC class I (H-2K$^b$) restricted epitope QIMYNYPAM (SEQ ID NO: 3) at 17 days in mice (pooled spleen and inguinal lymph node cells) following immunization by intradermal injections with BCG-OVA ($5\times10^6$ BCG-OVA per mouse), 0.1 μg αGalCer+BCG-OVA (Sep), 0.1 μg αGalCer+BCG-OVA (Mix), 4 μg αGalCer+BCG-OVA (Sep), 4 μg αGalCer+BCG-OVA (Mix), and αGalCer/BCG (Incorp).
Figure 10:
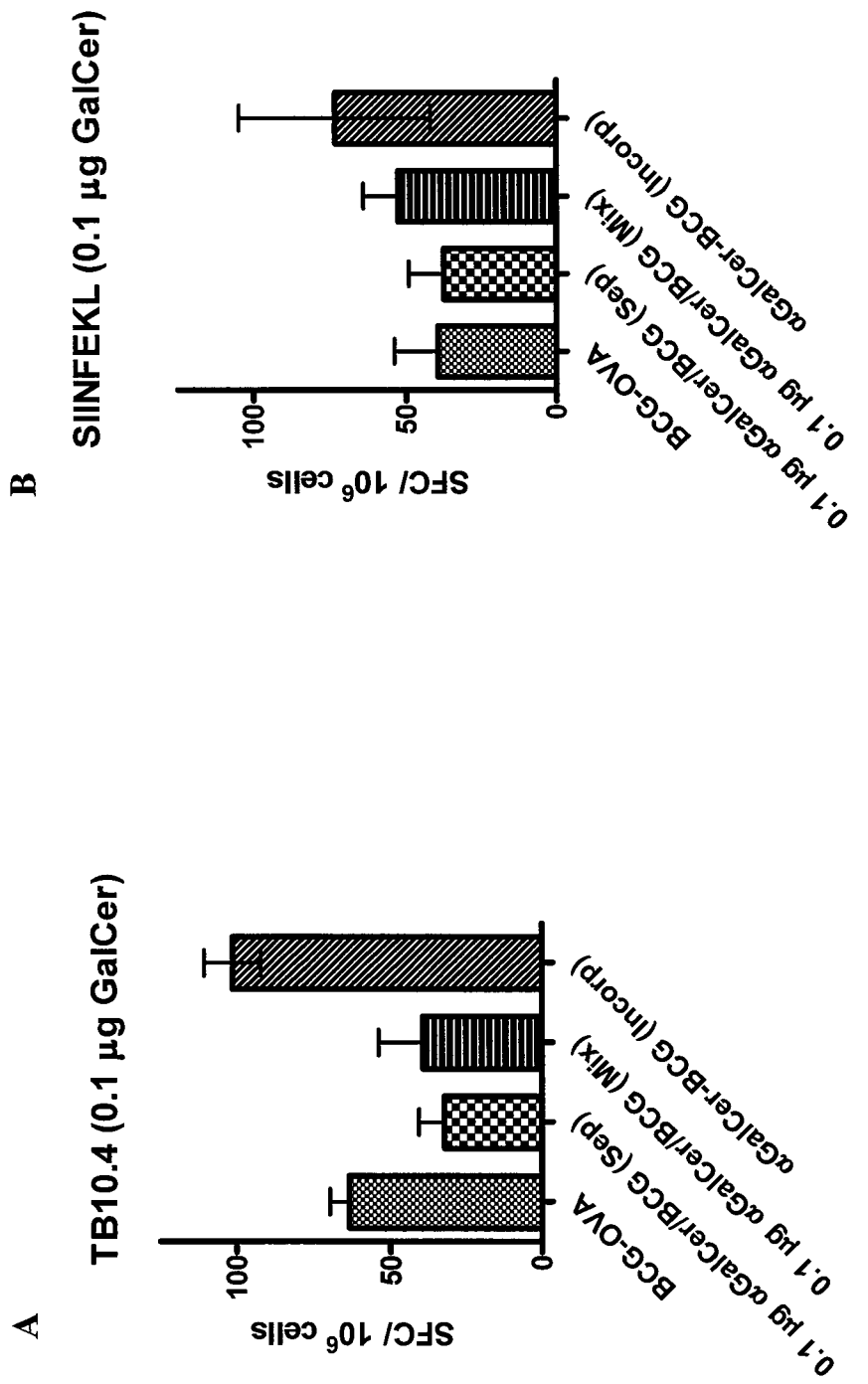
FIG. 10: Vaccination with αGalCer incorporated into BCG (Incorp) enhances CD8 T cell responses to mycobacterial antigens compared to separate administration (Sep=BCG-OVA and αGalCer injected separately at different sites) or mixing (Mix=BCG-OVA and αGalCer mixed together in the same syringe immediately before injection). (A) and (B) Graphs showing results of ELISPOT Assay for IFNγ producing CD8 T cells specific specific to (A) TB10.4 MHC class I (H-2K$^b$) restricted epitope QIMYNYPAM (SEQ ID NO: 3) or (B) SIINFEKL (SEQ ID NO: 1) in mice following immunization with BCG-OVA ($5\times10^6$ BCG-OVA per mouse), 0.1 μg αGalCer+BCG-OVA (Sep), 0.1 μg αGalCer+BCG-OVA (Mix), and αGalCer/BCG-OVA (Incorp).
Figure 11:
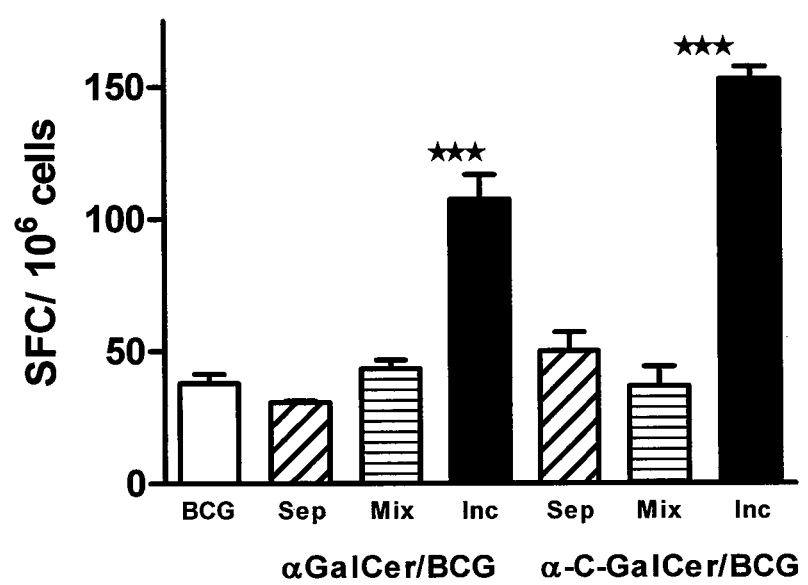
FIG. 11: iNKT cell activating glycolipids are incorporated directly into live mycobacteria to obtain optimal enhancement of CD8 T cell priming. Vaccination with αGalCer or α-C-GalCer incorporated into BCG (Inc) significantly enhanced CD8 T cell responses to mycobacterial antigens, compared to vaccination with unmodified (BCG), unmodified BCG plus 0.1 μg of glycolipid (αGalCer or α-C-GalCer as indicated) injected at a separate site (Sep), or unmodified BCG mixed with 0.1 μg of glycolipid (αGalCer or α-C-GalCer as indicated) immediately prior to injection and injected into the same site. Graphs showing results of ELISPOT Assay for IFNγ producing CD8 T cells specific specific to the MHC class I presented peptide of mycobacterial antigen TB10.4 MHC class I (H-2K$^6$) restricted epitope QIMYNYPAM (SEQ ID NO: 3) in spleen cell suspensions from mice at 3 weeks following immunization ***, $p<0.01$ (ANOVA).

Cell Wall Incorporation of NKT Cell Activating Ceramide-Like Glycolipids Enhances Protective Immunity Induced by the *M. bovis* BCG Vaccine Using immunization and challenge studies, this example demonstrates that the enhanced T cell priming observed when mice were vaccinated with either αGalCer-BCG or α-C-GalCer-BCG also improved the protective efficacy of the BCG vaccine.

C57BL/6 mice that were either naïve (saline) or immunized 2 months earlier by the intradermal route with $5\times10^6$ live BCG (Danish), αGalCer-BCG or α-C-GalCer-BCG were challenged by low-dose (50-100 CFU) aerosol infection with virulent *M. tuberculosis* H37Rv. In naïve mice, substantial growth in the lungs and dissemination to spleens were detected at 3 and 6 weeks after challenge. However, vaccination with BCG (Danish), α-GalCer-BCG or α-C-GalCer-BCG considerably reduced *M. tuberculosis* bacterial loads in both lungs and spleens of aerosol-challenged mice as compared with naive controls (FIGS. 6A and 6B). α-C-GalCer-BCG vaccination protected significantly better than BCG at the 3 week time point in both lungs and spleen. Immunization with α-C-GalCer-BCG also showed a more prolonged effect on control of *M. tuberculosis* infection compared with BCG immunization, as indicated by reductions in CFU in both the organs at 6 weeks after challenge. The C-glycoside was superior to αGalCer, as it improved the protective efficacy of BCG both in the lungs and spleen, probably because this analogue induces a pronounced Th1 cytokine response. The protection evoked by αGalCer-BCG and α-C-GalCer-BCG immunization was significantly greater than that obtained with BCG vaccination at the 6 week time point in lung and spleen.

Histopathological examination of the lungs from mice immunized with either BCG, αGalCer-BCG or the α-C-GalCer-BCG showed relatively mild inflammation with small and compact lymphocyte-rich granulomas, compared with naive mice, which had extensive, poorly organized granulomatous lesions (FIGS. 7A, 7B, 7C, and 7D). Predominantly lymphocytic infiltration was observed in mice vaccinated with αGalCer/BCG as compared to a mixed histiocytic and lymphocytic infiltration seen in BCG vaccinated mice.

Thus, a single intradermal immunization with αGalCer or α-C-GalCer incorporated BCG, led to a significant enhancement of protective immunity against an aerosol challenge with *M. tuberculosis* strain H37Rv.

Example 7

Adjuvant Activity of Incorporated Ceramide-Like Glycolipids Requires CD1d and is NKT Cell Activation Specific This example demonstrates that the adjuvant activity provided by incorporated ceramide-like glycolipid is due to specific activation of NKT cells. Immunization and challenge experiments with CD1d knock-out (KO) mice or Jα18 KO mice, which are both deficient in invariant NKT cells that are activated by the glycolipids were used. No difference in protection was observed between BCG immunized and the glycolipid-complexed BCG immunized CD1d KO mice (FIG. 6C) and Jα18 KO mice (FIG. 6D). Thus, the presence of invariant NKT cells is important for enhanced protection afforded in wild-type mice by a ceramide-like glycolipid incorporated into a mycobacterial cell wall.

Example 8

Antigen-Specific CD4 T Cell Priming by the Ceramide-Like Glycolipid Adjuvants

This example demonstrates that αGalCer-BCG and α-C-GalCer-BCG do not enhance CD4 T cell responses to p25 of Ag85B mycobacterial antigen. C57BL/6 mice were vaccinated with αGalCer-BCG or α-C-GalCer-BCG and analyzed for CD4 T cell responses to the P25 peptide of mycobacterial antigen-85B in the spleen by IFNγ ELISPOT. No differences were observed in priming of these CD4 T cells in mice which received the glycolipid-complexed BCG vaccines as compared to mice that were vaccinated with BCG alone (FIGS. 8A, 8B and 8C). $CD4^+$ T cell activation was assessed 7 days after infection by CFSE dilution. The percentage of lymphocytes in the lung in C57BL/6 mice at 2 months following vaccination with BCG, αGalCer/BCG or α-C-GalCer/BCG showed no significant enhancement with αGalCer/BCG or α-C-GalCer/BCG (FIG. 8D).

Priming of MHC class II-restricted CD4 T cells reactive to p25 of antigen85B in the context of vaccination was observed. Adoptive transfer of CFSE-labeled naive T cells from p25-reactive TCR-transgenic mice was used. Wolf A J et al., *J. Immunol.* 179(4):2509-19 (2007). $Thy1.1^+$ B6.PL mice were injected with CFSE-labeled $Thy1.2^+$ splenocytes from p25 mice, followed by vaccination with either with BCG alone, αGalCer-BCG or α-C-GalCer-ECG. $CD4^+$ T cell activation and proliferation were assessed by dilution of CFSE in the transferred population at 7 days after infection (FIG. 8E). No significant proliferation of transferred p25 T cells was observed in mice infected with BCG, αGalCer/BCG or α-C-GalCer/BCG (FIG. 8F). The activation and proliferation of p25 CD4 T cells between mice immunized with either BCG alone or BCG with the ceramide-like glycolipid adjuvants were similar.

Thus, the glycolipid adjuvants did not appear to have an impact on CD4 T cell responses.

Example 9

Enhancement of Antigen-Specific CD8 T Cell Priming by Administration of Ceramide-Like Glycolipid Incorporated into BCG Compared to Separate Administration or BCG Alone This example demonstrates that vaccination with ceramide-like glycolipid incorporated into BCG cell walls results in enhanced CD8 T cell responses to mycobacterial antigens compared to separate administration of BCG-OVA+αGalCer (injected separately at different sites), mixed administration of BCG-OVA+αGalCer (mixed together in the same syringe immediately before injection) or BCG-OVA alone. Administration was by intradermal injections. Three (3) mice were immunized per group. ELISPOT Assay for IFNγ producing CD8 T cells specific for the SIINFEKL (SEQ ID NO: 1) residues of OVA peptide at 17 days in mice following immunization with separate, mixed or cell wall-incorporation αGalCer and BCG showed enhanced T cell priming with αGalCer incorporated into the BCG cell wall (FIG. 9A). ELISPOT Assay for IFNγ producing CD8 T cells specific for the GYAGTLQSL (SEQ ID NO: 2) residues of TB10.3/4 Mtb peptide in mice following immunization with αGalCer-BCG also showed enhanced activity compared to separate or mixed administration (FIG. 9B). ELISPOT Assay for IFNγ producing CD8 T cells specific to TB10.4 in mice following immunization with αGalCer/BCG and ELISPOT Assay for IFNγ producing CD8 T cells specific to SIINFEKL in mice following immunization with αGalCer+BCG-OVA (administered separately or mixed) show that incorporated ceramide-like glycolipids enhanced activity compared to separate or mixed administration (FIGS. 10A and 10B). Similar results were obtained using α-C-GalCer instead of αGalCer (FIG. 11). Thus, the physically associated ceramide-like glycolipid adjuvant and mycobacterial cells show an improved enhancement of CD8 T cells, which is thought to be a basis for the adjuvant effect of mycobacterial vaccines, such as BCG.

These results indicate that by delivering the adjuvant directly to the same cells that become infected with the mycobacterium, the ceramide-like glycolipid adjuvant has an enhanced affect. Thus, incorporated adjuvant is expected to allow for smaller doses of vaccine to be used, as well as, reducing local and systemic toxicity, and lowering the cost of vaccine production.

The entire disclosure of all publications (including patents, patent applications, journal articles, laboratory manuals, books, or other documents) cited herein are hereby incorporated by reference.

What is claimed is:

1. A modified bacterium comprising: a bacterial cell and a glycosylceramide or analog thereof that is heterologous to said bacterial cell, wherein said glycosylceramide or analog thereof is incorporated into the cell wall of said bacterial cell, and wherein said glycosylceramide or analog thereof stimulates natural killer T (NKT) cells.

2. The modified bacterium of claim 1, wherein said glycosylceramide or analog thereof comprises Formula I:

(Formula I)

wherein R1 is a linear or branched $C_1$-$C_{27}$ alkane or $C_2$-$C_{27}$ alkene; or R1 is —C(OH)—R3 wherein R3 is a linear or branched $C_1$-$C_{26}$ alkane or $C_2$-$C_{26}$ alkene; or R1 is a $C_6$-$C_{27}$ alkane or alkene wherein (i) the $C_6$-$C_{27}$ alkane or alkene is substituted with a $C_5$-$C_{15}$ cycloalkane, $C_5$-$C_{15}$ cycloalkene, heterocycle, or aromatic ring or (ii) the $C_6$-$C_{27}$ alkane or alkene includes, within the $C_6$-$C_{27}$ alkyl or alkenyl chain, a $C_5$-$C_{15}$ cycloalkane, $C_5$-$C_{15}$ cycloalkene, heterocycle, or aromatic ring;

R2 is one of the following (a)-(e):
(a) —$CH_2(CH_2)_xCH_3$,
(b) —$CH(OH)(CH_2)_xCH_3$,
(c) —$CH(OH)(CH_2)_xCH(CH_3)_2$,
(d) —$CH=CH(CH_2)_xCH_3$,
(e) —$CH(OH)(CH_2)_xCH(CH_3)CH_2CH_3$, wherein X is an integer ranging from 4-17;

R4 is an α-linked or a β-linked monosaccharide, or when R1 is a linear or branched $C_1$-$C_{27}$ alkane, R4 is:

and
A is O or —$CH_2$.

3. The modified bacterium of claim 2, wherein R1 is —$(CH_2)_{22}CH_3$ or —$(CH_2)_{24}CH_3$.

4. The modified bacterium of claim 2, wherein R2 is —CH(OH)—$(CH_2)_{13}CH_3$.

5. The modified bacterium of claim 2, wherein R4 is galactosyl, mannosyl, fucosyl or glucosyl.

6. The modified bacterium of claim 1, wherein said glycosylceramide or analog thereof comprises an α-galactosylceramide or an analog thereof.

7. The modified bacterium of claim 6, wherein said α-galactosylceramide or analog thereof comprises Formula II:

(Formula II)

wherein
R1 is a linear or branched $C_1$-$C_{27}$ alkane or $C_2$-$C_{27}$ alkene; or R1 is —C(OH)—R3 wherein R3 is linear or branched $C_1$-$C_{26}$ alkane or $C_2$-$C_{26}$ alkene; and R2 is one of the following (a)-(e):
(a) —$CH_2(CH_2)_xCH_3$,
(b) —$CH(OH)(CH_2)_xCH_3$,
(c) —$CH(OH)(CH_2)_xCH(CH_3)_2$,
(d) —$CH=CH(CH_2)_xCH_3$,
(e) —$CH(OH)(CH_2)_xCH(CH_3)CH_2CH_3$, wherein X is an integer ranging from 4-17.

8. The modified bacterium of claim 7, wherein R2 is —CH(OH)$(CH_2)_xCH_3$, wherein X is an integer ranging from 4-13.

9. The modified bacterium of claim 7, wherein R1 is selected from the group consisting of $(CH_2)_9CH=CH—CH_2—CH=CH(CH_2)_4CH_3$, $(CH_2)_8CH=CH—CH_2—CH=CH(CH_2)_4CH_3$, $(CH_2)_7CH=CH—CH_2—CH=CH(CH_2)_4CH_3$, $(CH_2)_3CH=CH—CH_2—CH=CH—CH_2—CH=CH—CH_2—CH=CH—(CH_2)_4CH_3$, $(CH_2)_3CH=CH—CH_2—CH=CH—CH_2—CH=CH—CH_2—CH=CH—CH_2—CH=CH—CH_2CH_3$, $(CH_2)_7CH=CH—CH_2—CH=CH—(CH_2)_4CH_3$, $(CH_2)_7CH=CH—CH=CH(CH_2)_5CH_3$, $(CH_2)_8CH=CH—CH=CH(CH_2)_4CH_3$, $(CH_2)_9CH=CH—CH=CH(CH_2)_5CH_3$, $(CH_2)_6CH=CH—CH=CH—CH=CH(CH_2)_4CH_3$, $(CH_2)_6CH=CH—CH=CH—CH=CH(CH_2)_4CH_3$ and $(CH_2)_7CH=CH—CH=CH—CH=CH(CH_2)_3CH_3$.

10. The modified bacterium of claim 9, wherein the double bonds are cis or trans.

11. The modified bacterium of claim 6, wherein said α-galactosylceramide or analog thereof comprises Formula III:

(Formula III)

wherein R is H or —C(O)R1, wherein R1 is a linear or branched $C_1$-$C_{27}$ alkane or $C_2$-$C_{27}$ alkene; or R1 is —C(OH)—R3 wherein R3 is a linear or branched $C_1$-$C_{26}$ alkane or $C_2$-$C_{26}$ alkene; or R1 is a $C_6$-$C_{27}$ alkane or alkene wherein (i) the $C_6$-$C_{27}$ alkane or alkene is substituted with a $C_5$-$C_{15}$ cycloalkane, $C_5$-$C_{15}$ cycloalkene, heterocycle, or aromatic ring or (ii) the $C_6$-$C_{27}$ alkane or alkene includes, within the $C_6$-$C_{27}$ alkyl or alkenyl chain, a $C_5$-$C_{15}$ cycloalkane, $C_5$-$C_{15}$ cycloalkene, heterocycle, or aromatic ring; or R1 is a —$(CH_2)_n$R5, wherein n is an integer ranging from 0-5, and R5 is —C(O)OC$_2$H$_5$, an optionally substituted C$_5$-C$_{15}$ cycloalkane, an optionally substituted aromatic ring, or an aralkyl, and R2 is one of the following (a)-(e):

(a) —CH$_2$(CH$_2$)$_x$CH$_3$, (b) —CH(OH)(CH$_2$)$_x$CH$_3$, (c) —CH(OH)(CH$_2$)$_x$CH(CH$_3$)$_2$, (d) —CH=CH(CH$_2$)$_x$CH$_3$, (e) —CH(OH)(CH$_2$)$_x$CH(CH$_3$)CH$_2$CH$_3$, wherein X is an integer ranging from 4-17.

12. The modified bacterium of claim 11, wherein R1 is substituted with oxo; hydroxy; halogen; phenyl; —OC(O)R6; —OR6; —C(O)R6; or N(R6)$_2$, wherein each R6 is independently hydrogen, C$_1$-C$_6$ alkyl, or an aromatic ring optionally substituted with halogen; hydroxy; —OC(O)R7; —OR7; —C(O)R7 or N(R7)$_2$, and wherein each R7 is independently hydrogen or C$_1$-C$_6$ alkyl.

13. The modified bacterium of claim 11, wherein R1 is selected from the group consisting of

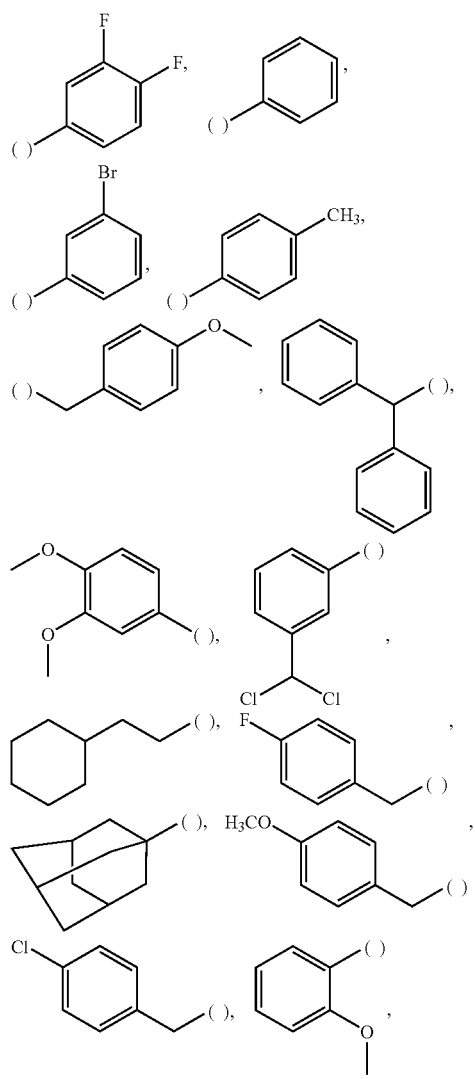

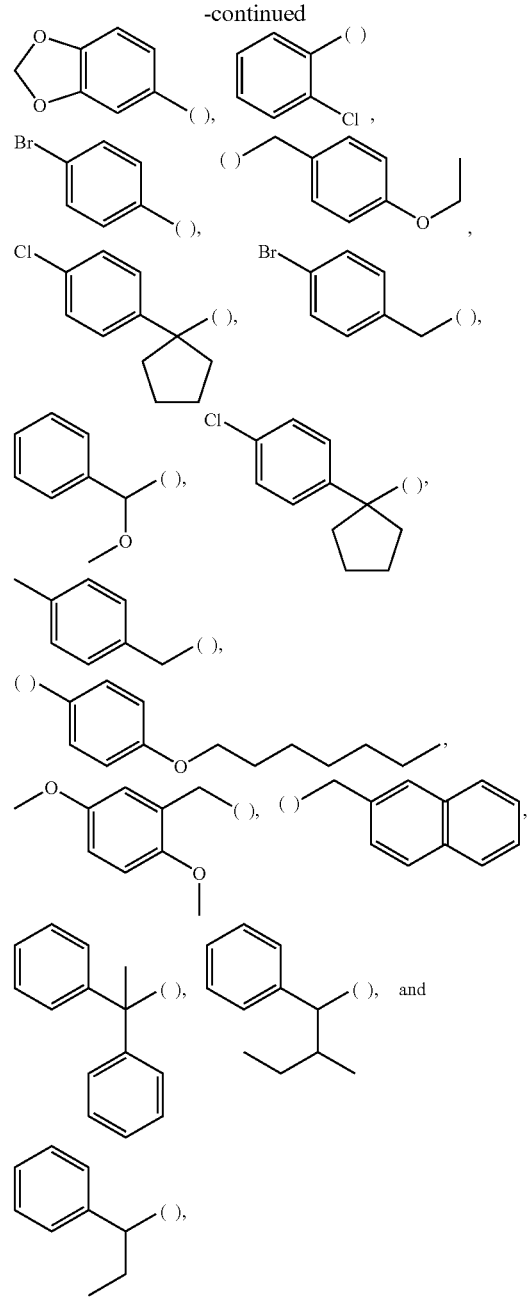

where ( ) represent the point of attachment of R1 to the compound of Formula III.

14. The modified bacterium of claim 6, wherein said α-galactosylceramide or analog thereof comprises (2S,3S,4R)-1-O-(α-D-galactopyranosyl)-N-hexacosanoyl-2-amino-1,3,4-octadecanetriol (KRN7000) or (2S,3S)-1-O-(α-D-galactopyranosyl)-N-hexacosanoyl-2-amino-1,3-octadecanediol).

15. The modified bacterium of claim 6, wherein said α-galactosylceramide or analog thereof comprises (2S,3S,4R)-1-CH$_2$-(α-galactopyranosyl)-N-hexacosanoyl-2-amino-1,3,4-octadecanetriol (α-C-GalCer).

16. The modified bacterium of claim 1, wherein said bacterial cell is selected from the group consisting of a mycobacterial cell, a *Listeria* cell, a *Salmonella* cell, a *Yersinia* cell, a *Francisella* cell, and a *Legionella* cell.

17. The modified bacterium of claim 16, wherein said bacterial cell is a mycobacterial cell.

18. The modified bacterium of claim 17, wherein said mycobacterial cell is selected from the group consisting of a *M. tuberculosis* complex (MTBC) cell and a nontuberculous mycobacterial (NTM) cell.

19. The modified bacterium of claim 18, wherein said MTBC cell is selected from the group consisting of a *M. tuberculosis* cell, a *M. bovis* cell, a *M. bovis* bacille Calmette-Guérin (BCG) cell, a *M. africanum* cell, a *M. canetti* cell, a *M. caprae* cell, and a *M. pinnipedii'* cell.

20. The modified bacterium of claim 1, wherein said bacterial cell is live, killed, or attenuated.

21. The modified bacterium of claim 1, which enhances antigen-specific CD8 T cell responses against an antigen.

22. The modified bacterium of claim 21, wherein said antigen is a mycobacterial antigen.

23. The modified bacterium of claim 1, which expresses a heterologous antigen.

24. The modified bacterium of claim 23, wherein said heterologous antigen is a viral antigen, a bacterial antigen, a fungal antigen, a parasitic antigen, or a tumor specific antigen.

25. The modified bacterium of claim 23, wherein said heterologous antigen is an immunogenic peptide.

26. The modified bacterium of claim 1, wherein said bacterial cell is a recombinant bacterial cell.

27. A composition comprising the modified bacterium of claim 1, and a pharmaceutical carrier.

28. The composition of claim 27, wherein said pharmaceutical carrier is selected from the group consisting of saline, buffered saline, dextrose, water, glycerol, and combinations thereof.

29. The composition of claim 27, further comprising an adjuvant.

30. The composition of claim 29, wherein said adjuvant is selected from the group consisting of a glycolipid, a cytokine, a chemokine, a compound that induces the production of cytokines and chemokines, a growth factor, an interferon, a bacterial component, an aluminum-based salt, a calcium-based salt, a silica, a polynucleotide, a toxoid, a serum protein, a virus, a virally-derived material, a poison, a venom, a imidazoquiniline compound, TLR9 agonists, TLR7/8 agonists, a poloxamer, a cationic lipid, an inert carrier, a pluronic block polymer, a depot former, a surface active material, a macrophage stimulator, an alternate pathway complement activator, a non-ionic surfactant, mLT, SAF, LPS derivatives, trehalose dimycolate (TDM), cell wall skeleton (CWS), QS21, complete Freund's adjuvant, incomplete Freund's adjuvant, macrophage colony stimulating factor (M-CSF), tumor necrosis factor (TNF), 3-O-deacylated MPL, a CpG oligonucleotide, a saponin, a polyoxyethylene ether, a polyoxyethylene ester, and any combination of more than one second adjuvant.

31. A vaccine composition comprising the modified bacterium of claim 1.

32. A method of treating a disease in an animal, comprising administering to an animal in need of said treatment the modified bacterium of claim 1; wherein said modified bacterium is administered in an amount sufficient to alter the progression of said disease.

33. A method of preventing a disease in an animal, comprising administering to an animal in need of said prevention the modified bacterium of claim 1; wherein said modified bacterium is administered in an amount sufficient to induce an immune response in said animal against said disease.

34. A method of inducing an immune response against an antigen in an animal, comprising administering to said animal the modified bacterium of claim 1.

35. A method of modulating a CD8 T-cell response to BCG in an animal comprising administering to said animal an effective amount of the modified bacterium of claim 1, wherein said bacterial cell is a BCG cell.

36. A kit comprising the modified bacterium of claim 1.

37. A method of making a glycosylceramide/mycobacterial complex comprising (a) culturing a mycobacterial cell in culture medium and (b) adding a glycosylceramide or analog thereof that is heterologous to the mycobacterial cell and that stimulates natural killer T (NKT) cells to the culture medium under conditions where said glycosylceramide or analog thereof incorporates into the cell wall of said mycobacterial cell.

38. A method of producing a vaccine against an antigen comprising: (a) isolating the glycosylceramide/mycobacterial complex of claim 37 and (b) adding a pharmaceutical carrier to the isolated complex of (a).

39. The composition of claim 30, wherein said adjuvant is selected from the group consisting of CPG ODNS, imiquimod, and monophosphoryl lipid A, and any combination thereof.

40. The modified bacterium of claim 1, wherein said modified bacterium is a carrier for a heterologous antigen.

* * * * *

```
SEQUENCE LISTING

<160> NUMBER OF SEQ ID NOS: 4

<210> SEQ ID NO 1
<211> LENGTH: 8
<212> TYPE: PRT
<213> ORGANISM: Artificial Sequence
<220> FEATURE:
<223> OTHER INFORMATION: Synthetic OVA peptide

<400> SEQUENCE: 1

Ser Ile Ile Asn Phe Glu Lys Leu
1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic TB10.3/4 MHC-I (H-2Kd) epitope

<400> SEQUENCE: 2

Gly Tyr Ala Gly Thr Leu Gln Ser Leu
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic TB10.4 MHC-I (H-2Kb) epitope

<400> SEQUENCE: 3

Gln Ile Met Tyr Asn Tyr Pro Ala Met
1               5

<210> SEQ ID NO 4
<211> LENGTH: 15
<212> TYPE: PRT
<213> ORGANISM: Artificial Sequence
<220> FEATURE:
<223> OTHER INFORMATION: Synthetic peptide-25

<400> SEQUENCE: 4

Phe Gln Asp Ala Tyr Asn Ala Ala Gly Gly His Asn Ala Val Phe
1               5                   10                  15
```